United States Patent [19]

Sessler et al.

[11] Patent Number: 5,410,045
[45] Date of Patent: Apr. 25, 1995

[54] RUBYRIN AND RELATED EXPANDED PORPHYRINS

[75] Inventors: Jonathan L. Sessler, Austin, Tex.; Takashi Morishima, Yokohama, Japan; Steven J. Weghorn, Austin, Tex.

[73] Assignee: Board of Regents, The University of Texas System, Austin, Tex.

[21] Appl. No.: 15,208

[22] Filed: Feb. 9, 1993

Related U.S. Application Data

[63] Continuation-in-part of Ser. No. 926,357, Aug. 4, 1992, abandoned.

[51] Int. Cl.$^6$ .......................................... C07D 487/22
[52] U.S. Cl. .......................................... 540/472; 540/145
[58] Field of Search ................................ 540/145, 472

[56] References Cited

U.S. PATENT DOCUMENTS

| | | | |
|---|---|---|---|
| 4,883,790 | 11/1989 | Levy et al. | 540/145 |
| 4,935,498 | 6/1990 | Sessler et al. | 534/15 |
| 5,041,078 | 8/1991 | Matthews et al. | 604/4 |

FOREIGN PATENT DOCUMENTS

| | | |
|---|---|---|
| 0196515 | 3/1986 | European Pat. Off. . |
| 0233701 | 1/1987 | European Pat. Off. . |
| WO90/10633 | 9/1990 | European Pat. Off. . |

OTHER PUBLICATIONS

Gossauer, Bull. Soc. Chim. Belg vol. 92 Sep. 1983 pp. 793–795.
Broadhurst et al., J. Chem. Soc., Perkin I., 1972, pp. 2111–2116.
Aoyama, et al., "Multi-Point Interaction of Phosphates with Protonated Pyridylporphyrin, Discrimination of Monoalkyl and Dialkyl Phosphates," *Chemistry Letters*, 1991, 1241–1244.
Bauer et al., "Sapphyrins: Novel Aromatic Pentapyrrolic Macrocycles," *J. Am. Che. Soc.*, 1983, 105:6429–6436.
Broadhurst and Grigg, "18- and 22-π-Electron Macrocycles Containing Furan, Pyrrole, and Thiophen," *Chemical Communications*, 1969, 1480–1482.
Broadhurst and Grigg, "The Synthesis of 22 π-Electron Macrocycles. Sapphyrins and Related Compounds," *J.C.S. Perkin*, 2111–2116, 1972.
Claude et al., "Binding of Nucleosides, Nucleotides and Anionic Planar Substrates by Bis–Intercaland Receptor Molecules," *J. Chem. Soc., Chem. Commun.*, 1991, 17:1182–1185.

(List continued on next page.)

*Primary Examiner*—Mukund J. Shah
*Assistant Examiner*—Pavanaram K. Sripada
*Attorney, Agent, or Firm*—Arnold, White & Durkee

[57] ABSTRACT

The present invention is directed to the synthesis and use of novel macrocyclic compounds, based upon a new class of expanded porphyrins, termed rubyrins. Disclosed herein is the structure and synthesis of a prototypical rubyrin and various substituted rubyrin analogues, conjugates and compositions. Rubyrin itself is characterized by the presence of six pyrrolic subunits contained within a fully aromatic 26 π-electron macrocyclic framework and by UV/VIS absorption bands that are very red-shifted as compared to those of other porphyrins or pentapyrrolic expanded porphyrins. The rubyrin-type class of compounds is further characterized by an ability to undergo facile protonation at the pyrrolic nitrogens and, once protonated, by an ability to form complexes with anions such as nucleotide-containing compounds. Rubyrin-based compounds are useful as, for example, anion chelators and receptors and as transporters for various anionic compounds including antiviral agents. In addition to the 26 π-electron target system, the present invention concerns other oxidation states bearing the same connectivity and the same total number of non-hydrogen atoms, and various analogues in which different substituents are present at the various meso and/or β-pyrrolic positions or in which furan and/or thiophene moieties replace one or more of the six pyrrolic subunits.

19 Claims, 14 Drawing Sheets

OTHER PUBLICATIONS

Cramer et al., "Synthesis and Structure of the Chloride and Nitrate Inclusion Complexes of [16-Pyrimidinium crown-4]," *J. Am. Chem. Soc.*, 1991, 113:7033–7034.

Cuellar and Marks, "Synthesis and Characterization of Metallo and Metal-Free Octaalkylphthalocyanines and Uranyl Decaalkylsuperphthalocyanines," *Inorg. Chem.*, 1981, 20:3766–3770.

Dietrich et al., "Proton Coupled Membrane Transport of Anions Mediated by Cryptate Carriers," *J. Chem. Soc. Chem. Comm.*, 1988, 11:691–692.

Dixon et al., "Molecular Recognition: Bis-Acylguanidiniums Provide a Simple Family of Receptors for Phosphodiesters," *J. Am. Chem. Soc.*, 1992, 114:365–366.

Furuta et al., "Phosphate Anion Binding: Enhanced Transport of Nucleotide Monophosphates Using a Sapphyrin Carrier," *Journal of the American Chemical Society*, 1991, 113:6677–6678.

Furuta et al., "Enhanced Transport of Nucleosides and Nucleoside Analogues with Complementary Base-Pairing Agents," *Journal of the American Chemical Society*, 1991, 113:4706–4707.

Furuta et al., "Protonated Rubyrin and C-Tips: Co-carriers for the Transport of Guanosine 5'-Monophosphate at Neutral pH," *Supramolec. Chem.*, in Press, 1–9 1994.

Galán et al., "A Synthetic Receptor for Dinucleotides," *J. Am. Chem. Soc.*, 1991, 113:9424–9425.

Galán et al., "Selective Complexation of Adenosine Monophosphate Nucleotides By Rigid Bicyclic Guanidinium Abiotic Receptors," *Tetrahedron Letters*, 32(15):1827–1830 1991.

Harriman et al., "Metallotexaphyrins: A New Family of Photosensitisers for Efficient Generation of Singlet Oxygen," *J. Chem. Soc. Chem. Commun.*, 1989, 314–316.

Hisatome et al., "Porphyrins Coupled with Nucleoside Bases. Synthesis and Characterization of Adenine- and Thymine-Porphyrin Derivatives," *Chemistry Letters*, 1990, 2251–2254.

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J. Am. Chem. Soc.*, 1990, 112:3896–3904.

Hosseini et al., "Multiple Molecular Recognition and Catalysis. Nucleotide Binding and ATP Hydrolysis by a Receptor Molecule Bearing an Anion Binding Site, an Intercalator Group, and a Catalytic Site," *J. Chem. Soc. Chem. Commun.*, 1988, 9:596–598.

Kimura et al., "A Study of New Bis(macrocyclic polyamine) Ligands as Inorganic and Organic Anion Receptors," *J. Org. Chem.*, 1990, 55(1):46–48.

Kimura, "Macrocyclic Polyamines as Biological Cation and Anion Complexones–An Application to Calculi Dissolution," 113–141 1991.

Král et al., "Synthetic Sapphyrin-Cytosine Conjugates: Carriers for Selective Nucleotide Transport at Neutral pH," *Journal of American Chemical Society*, 1992, 114:8704–8705.

Li and Diederich, "Carriers for Liquid Membrane Transport of Nucleotide 5'-Triphosphates," *J. Org. Chem.* 1992, 47:3449–3454.

Marks and Stojakowvic, "Large Metal Ion-Centered Template Reactions. Chemical and Spectral Studies of the Superphthalocyanine Dioxocyclopentakis (1-iminoisoindolinato)uranium(VI) and Its Derivatives," *J. Am. Chem. Soc.*, 1978, 1695–1705.

Rexhausen and Gossauer, "The Synthesis of a New 22 π-Electron Macrocyle:Pentaphyrin," *Che. Soc. Che. Commun.*, 1983, 6:275.

Schmidtchen, "A Non-Macrocyclic Host for Binding Organic Phosphates in Protic Solvents," *Tetrahedron Letters*, 1989, 30(34):4493–4496.

Seel and Vogtle, "Molecular Recognition and Transport of Nucleobases–Superiority of Macrobicyclid Host Molecules," *Angew. Chem. Int. Ed. Engl.*, 1991, 30(4):442–444.

Sessler et al., "Anion Binding: A New Direction in Porphyrin-Related Research," *Pure & Applied Chem.*, 65(3):393–398, 1993.

Sessler et al., "Rubyrin: A New Hexapyrrolic Ex- (List continued on next page.)

OTHER PUBLICATIONS panded Porphyrin," *Angew. Chem. Int. Ed. Engl.*, 1991.

Sessler et al., "Cytosine Amine Derivatives," *J. Org. Chem.*, 1992, 47:826–834.

Sessler et al., "Enhanced Transport of Fluoride Anion Effected Using Protonated Sapphyrin as a Carrier," *J. Chem. Soc. Chem. Commun.*, 1991, 1732–1735.

Sessler et al., "In vitro photodynamic activity of diprotonated sapphyrin: a 22-π-electron pentapyrrolic prophyrin-like macrocycle," *Chemical Abstracts*, 1990, 112:348–349, 112:194584t.

Sessler et al., "A water-stable gadolinium (III) complex derived from a new pentadentate expanded porphyrin ligand," *Chemical Abstracts*, 1989, 11:720, 111:125716e.

Sessler et al., "Synthetic and Structural Studies of Sapphyrin, a 22-π-Electron Pentapyrrolic Expanded Porphyrin", *J. Am. Chem. Soc.*, 1990, 112:2810–2813.

Sessler et al., "An Expanded Porphyrin: The Synthesis and Structure of a New Aromatic Pentadentate Ligand," *J. Am. Chem. Soc.*, 1988, 110:5586–5588.

Sessler and Burrell, "Expanded Prophyrins," *Current Chemistry*, 161:66–71 1988.

Shionoya et al., "Diprotonated Sapphyrin: A Fluoride Selective Halide Anion Receptor," *Journal of the American Chemical Society*, 1992, 114:5714–5722.

Tabushi et al., "Lipophilic Diammonium Cation Having a Rigid Structure Complementary to Pyrophosphate Dianions of Nucleotides. Selective Extraction and Transport of Nucleotides," *J. Am. Chem. Soc.*, 1981, 103:6152–6157.

Tohda et al., "Liquid Membrane Electrode for Guanosine Nucleotides Using a Cytosine-Pendant Triamine Host as the Sensory Element," *Analytical Chemistry*, 1992, 64(8):960–964.

10a. $R_1 = H; R_2 = CH_3$
10b. $R_1 = CH_3; R_2 = H$

19

20. X=Y=O
21. X=S; Y=O
22. X=S; Y=NH
23. X=O; Y=NH
24. X=Y=S a. R = H
b. R = PO$_3^{2-}$
c. R = PO$_3$PO$_3$PO$_3^{2-}$ d. R=H
e. R=PO$_3^{2-}$

RUBYRIN AND RELATED EXPANDED PORPHYRINS

This application is a continuation-in-part of U.S. Ser. No. 07/926,357, filed Aug. 4, 1992, now abandoned. The government owns rights in the present invention pursuant to NIH grant AI 28845.

BACKGROUND OF THE INVENTION

1. Field of the Invention

The present invention relates generally to macrocyclic expanded porphyrin compounds, and particularly, to the novel expanded porphyrin termed rubyrin and to a class of rubyrin analogues. Disclosed are rubyrin and rubyrin analogue compounds compositions, and methods of using protonated rubyrin compounds as anion chelators, receptors and transporters.

2. Description of the Related Art

In recent years increasing effort has been devoted to the preparation of novel "expanded porphyrins"[1], large pyrrole-containing macrocyclic analogues of the porphyrins (e.g. porphine, FIG. 1A) and a number of such systems are now known[1-17]. However, only a few fully conjugated examples have been reported that contain more than four pyrrolic subunits, namely the smaragdyrins[2,3] sapphyrins[2-6], pentaphyrins[7,8], hexaphyrins[9] and superphthalocyanines[10]. These compounds are represented in their generalized substituent-free forms as FIG. 1B–FIG. 1F).

To date, there remains relatively little documented information concerning the chemistry of the above-mentioned expanded porphyrin systems. Indeed, at present, structural information is available only for derivatives of sapphyrin (e.g. FIG. 1B)[4,5] and pentaphyrin (e.g. FIG. 1C)[8] in the all-pyrrole series. Therefore, numerous fundamental questions concerning these molecules still remain to be answered, such as those pertaining to ring size, aromaticity, and effective macrocycle stability. The synthesis and structural characterization of hexapyrrolic macrocycles would be a particular advance in this area, allowing the answers to such interrelated questions to be elucidated.

It has long been appreciated that a considerable number of ionic (e.g. phosphorylated) nucleotide analogues exhibit antiviral activity in cell-free extracts, yet are inactive in vivo due to their inability to cross lipophilic cell membranes[25,26]. For example, the anti-herpetic agent, acyclovir (FIG. 9A, structure a; 9-[(2-hydroxyethoxy)methyl]-9H-guanine), is typical in that it is able to enter the cell only in its uncharged nucleoside-like form. Upon gaining entry to the cytoplasm it is phosphorylated, first by a viral-encoded enzyme, thymidine kinase (FIG. 9A, structure b), and then by relatively nonspecific cellular enzymes to produce the active, ionic triphosphate nucleotide-like species (FIG. 9A, structure c). There it functions both as an inhibitor of the viral DNA polymerase and as a chain terminator for newly synthesized herpes simplex DNA.

Many other potential antiviral agents, including, for instance, the anti-HIV agent, Xylo-G (FIG. 9B; structure d) 9-($\beta$-D-xylofuranosyl)guanine), on the other hand, are not phosphorylated by a viral enzyme and are, therefore, largely or completely inactive[27]. If, however, the active monophosphorylated forms of these putative drugs (such as in FIG. 9B, structure e) could be transported into cells, it would be possible to fight viral infections with a large battery of otherwise inactive materials. If such specific into-cell transport were to be achieved, it would therefore greatly augment the treatment of such debilitating diseases as, for example, AIDS, herpes, hepatitis and measles. Given the fact that AIDS is currently a major national health problem of frightening proportions, and that something so nominally benign as measles still claims over 100,000 lives per year world-wide[26], treatment of these diseases would be particularly timely and worthwhile.

At present, no general set of nucleotide transport agents exists. In early work, Tabushi was able to effect adenosine nucleotide transport using a lipophilic, diazabicyclooctane-derived, quaternary amine system[28]. However, this same system failed to mediate the transport of guanosine 5'-monophosphate (GMP) or other guanosine-derived nucleotides. Since then, considerable effort has been devoted to the generalized problem of nucleic acid base ("nucleobase") recognition, and various binding systems have been reported.

Currently known nucleotide binding systems include acyclic, macrocyclic, and macrobicyclic polyaza systems[29-37]; nucleotide-binding bis-intercalands[38]; guanidinium-based receptors[39-46]; and various rationally designed H-bonding receptors[47-53]. These latter H-bonding receptors have been shown to be effective for the chelation of neutral nucleobase and/or nucleoside derived substrates but, without exception, have also all proved unsatisfactory for the important task of charged nucleotide recognition. Large macrocyclic compounds, particularly macrocyclic compounds larger than sapphyrins, which could be relatively easily protonated could prove to be useful in anion binding and transport.

Despite intensive efforts in this field, there is currently no synthetic system capable of effecting the recognition and through-membrane transport of phosphate-bearing species such as anti-viral compounds. Furthermore, there are presently no rationally designed receptors which are "tunable" for the selective complexation of a given nucleobase-derived system.

There is clearly, therefore, a major need for novel drug delivery systems to be developed. Compounds which would allow negatively-charged (anionic) structures, particularly specifically-recognized nucleotides, to be transported across naturally lipophilic cellular membranes would represent an important scientific and medical advance. The development of such anion carriers may also prove to be important in the clinical treatment of cystic fibrosis, in that such compounds would likely facilitate the out-of-cell diffusion of chloride anions.

SUMMARY OF THE INVENTION

The present invention addresses these and other shortcomings in the prior art by providing compositions for use in specific anion binding and transport. The invention concerns a class of novel expanded porphyrins, or macrocycles, termed rubyrin and analogues thereof. Rubyrin and rubyrin analogues are able to bind negatively charged substances, anions, at near-neutral pH, and have the ability to transport anionic compounds across cell membranes. The rubyrin macrocyclic compounds of this invention are particularly contemplated for use transporting antiviral nucleotide analogues into cells, and in facilitating chloride anion exit from cells. They will thus find use in the treatment of a variety of viral diseases and also cystic fibrosis.

Rubyrin and substituted derivatives thereof are red in dilute organic solution, hence the use of the trivial name "rubyrin" from the Latin rubeus, for this new class of expanded porphyrins. Rubyrin itself is a macrocycle which can be generally characterized by the presence of six pyrrolic subunits contained within a fully aromatic 26 $\pi$-electron macrocyclic framework and by UV/VIS absorption bands that are very red-shifted as compared to those of either porphyrins or sapphyrins (pentapyrrolic expanded porphyrins).

In a general and overall sense, the novel rubyrin compounds of the present invention include those with structures in accordance with the general structures of FIG. 2D-2F. In these structures, the substituents $A_1$ and $A_2$ may be nitrogen, oxygen or sulphur. In general, the substituents $R_1$, $R_2$, $R_3$, $R_4$, $R_5$ and $R_6$ and $X_1$, $X_2$, $X_3$, and $X_4$ may separately and independently be H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether or substituted amide.

In certain embodiments, any one of the substituents $R_1$–$R_6$ or $X_1$–$X_4$ may be of the formula $(CH_2)_n$—A—$(CH_2)_m$—B. In this formula, n and m are integers <10 or zero; A may be $CH_2$, O, S, NH or $NR_7$, wherein $R_7$ may again be any of the groups listed above for $R_1$–$R_6$; and B will be a chosen, or desirable, functional unit. A "chosen functional unit" is used herein to refer to any compound or substance which one may desire to conjugate to a rubyrin molecule. Compounds based upon nucleobases, such as a single nucleobase, modified nucleobase, a nucleobase-type anti-viral compound, or an oligo- or polynucleotide; or compounds based upon saccharides, such as a sugar, sugar derivative or polysaccharide, are particularly contemplated for use in conjugating to rubyrin. However, the use of other compounds in rubyrin conjugates is also envisioned. Further suitable compounds include, for example, metal chelating groups; alkylating agents; steroids and steroid derivatives; amino acids, peptides and polypeptides; further rubyrin molecules, rubyrin derivatives or polymeric rubyrins; other macrocyclic compound such as sapphyrin or texaphyrin, or polymers or derivatives thereof; or even a polymeric matrix or solid support.

Rubyrin and analogues thereof may be further characterized by the ability to undergo facile protonation at the pyrrolic nitrogens and, once protonated, by an ability to form complexes with anions. An advantageous functional characteristic of rubyrin and analogues thereof is the ability to bind anions at near-neutral pH and to transport anions across lipophilic structures such as biological membranes. Preferred compounds of the present invention therefore have the capacity to bind anions and yet the ability to retain overall supramolecular charge neutrality. In particular, the fact that rubyrins are larger than sapphyrins, the only other class of compounds known to display such behavior, makes them considerably easier to protonate and thus much more effective in the recognition and transport of anions than this other class of molecules. This then represents a significant advance embodied in the present invention.

In certain embodiments, the invention concerns a macrocyclic rubyrin compound, represented in its generalized substituent free form by FIG. 2A, a structure in turn that corresponds to the macrocyclic system 29,30,31,32,33,34hexaazaheptacyclo [24.2.1.1$^{2,5}$.1$^{7,10}$.1$^{12,15}$.1$^{16,19}$.1$^{21,24}$]tetratriaconta-1,3,5,7(31),8,10,12,14,16,18,20,22,24(34),25,27-pentadecaene.

It will be understood by those of skill in the art of organic chemistry, however, that the present invention is not limited to compounds in accordance with FIG. 2A. Indeed, also included within the context of this disclosure are analogues of FIG. 2A, namely macrocycles based upon FIG. 2B and FIG. 2C, which have the same overall connectivity and same number of non-hydrogen atoms but which differ from the structurally characterized 26 $\pi$-electron prototypes by the number of total electrons contained within the $\pi$-electron periphery. For example, 28$\pi$-electron rubyrin analogues, as described in Examples V and VI, fall within the scope of the present invention. A particular example of a compound in accordance with FIG 2B is structure 19 of FIG. 5, namely 4,8,13,18,23,27-hexaethyl-3,9,14,17,22,28-hexamethyl-29,30,31,32,33,34hexaazaheptacyclo[24.2.1.1$^{2,5}$.1$^{7,10}$.1$^{12,15}$.1$^{16,19}$.1$^{21,24}$]tetratriaconta-1,3,5,7,9,11,13,15,17,19,21,23,25,27-tetradecaene.

Rubyrin compounds in which two or more of the pyrrolic nitrogen atoms have been replaced by oxygen or sulfur are also encompassed by the present invention. In this context, the oxygen or sulfur atoms are termed "heteroatoms", and the resultant rubyrin analogues may be referred to as heteroatomic compounds. Rubyrin analogues comprising four heteroatoms are exemplified in general by the macrocycle structures 20-24 (FIG. 6), which may variously contain two or four nitrogen, oxygen or sulphur atoms. The synthesis of rubyrin analogues in which two, four, or even six, of the nitrogen atoms have been replaced by oxygen or sulfur is described in Example X. The condensation of differing oxygen- or sulphur-containing units, from any one of a variety of readily available starting materials, under the rubyrin forming conditions disclosed herein, will result in the generation of macrocycles with any desired combination of nitrogen, oxygen or sulfur, based on starting materials chosen. Macrocycles containing combinations of nitrogen with either oxygen or sulphur, or alternatively, oxygen in combination with sulphur, such as those represented by structures 87, 92, 99 and 104 in reaction schemes P through S, are therefore encompassed by the present invention.

It will also be understood that any of the above rubyrin compounds may be either singly or doubly protonated, and in certain embodiments, triply or four-fold protonated.

The rubyrin compounds of the present invention are specifically exemplified by those compounds having structures in accordance with structures 10a, 10b, 17a, 17b, 18a, 18b and 19, as set forth in FIGS. 3, 4A, FIG. 4B and FIG. 5, respectively, as well as by other structures discussed hereinbelow and/or set forth in the figures and various reaction schemes presented herein. As will be understood by those of skill in the art, the present invention also encompasses several other rubyrin analogues. For example, different combinations of bipyrroles and pyrroles may be employed, such as those set forth in FIG. 11, FIG. 12A and FIG. 12B, both in the first and second condensation steps, to yield a variety of different products. In one instance, this is exemplified herein by the generation of a rubyrin analogue in which four of the 12 possible β-pyrrolic positions are either unsubstituted or replaced by a range of functionalized alkyl groups. The generation of various other rubyrin analogues is described throughout the specification, such as in Example VII, and represented in various reaction schemes, for example, Schemes A through E. A range of compounds with a wide variety of alkyl and/or aryl substituents in the meso and/or β-pyrrolic positions thus fall within the scope of the present invention, as represented by exemplary structures 27, 35, 40 and 47.

Any macrocyclic compound with a structure in accordance with any of FIG. 2A–2C, or FIG. 6 may be prepared in which different substituents are present at the various meso and/or B-pyrrolic positions or in which furan and/or thiophene moieties replace one or more of the six pyrrolic subunits. Such substituents may separately and independently include, H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether, or substituted amide groups.

Examples of functional group manipulation in B-substituted pyrroles are shown in FIG. 11, and starting pyrroles in FIG. 12A and 12B. Methods for the preparation of such pyrroles will be apparent to those of skill in the art and are described in various references, for example, Paine (1978)[81a]; Sessler et al. (1991)[81b]; and Zard & Barton, (1985)[81c]. Functional group manipulation of the β-positions is possible after macrocycle formation, or the appropriately substituted pyrroles may be used directly, depending upon the particular pyrrole to be used. The α-positions may be carboxyl-, ester-, formyl-, alkyl-, and/or unsubstituted and may also be directly linked to other pyrroles or linked to other pyrroles via a methylene bridge.

The synthetic methodology of the present invention also provides for the synthesis of a wide variety of other rubyrin derivatives or conjugates, wherein a functionalized rubyrin macrocycle is appended to a moiety of desirable chemical function. Rubyrin may thus also be conjugated to, for example, nucleobases, nucleobase derivatives and oligo- or polynucleotides; sugars, sugar derivatives and polysaccharides; metal chelating agents; other rubyrin molecules, polyrubyrins, sapphyrin or texaphyrin, polymers and solid support matrices; amino acids, peptides and polypeptides; steroids and steroid derivatives; and alkylating agents. It is contemplated that one of skill in the art will be able to prepare various rubyrin conjugates, including those listed above, without undue experimentation given the readily-available starting materials and in light of the synthetic methodology disclosed in the present application.

In certain embodiments, rubyrin compounds are contemplated which contain the rubyrin macrocycle core for phosphate binding and also nucleobase "appendages" for specific nucleic acid recognition (FIG. 10). These are referred to as rubyrinnucleobase conjugates, which term is intended to include any conjugate formed by the covalent conjugation of any rubyrin macrocycle to any nucleobase. The rubyrin-nucleobase conjugates of the present invention may be of either the mono- or di-substituted forms, as represented by the general structure of FIG. 10. A mono-substituted rubyrin-nucleobase conjugate is a compound in which only one position, i.e., only one of the groups $R_1$–$R_6$, or even $X_1$–$X_4$, is covalently attached to a nucleobase-containing compound, whereas di-substituted conjugates have nucleobase substitutions at two independent positions. Both mono- and di-substituted conjugates may comprise one, two, or a plurality of nucleobase units, the difference being in the point of attachment and not in the number of individual units attached to the macrocycle. The synthesis of such conjugates is described in Example VIII and specific rubyrin-nucleobase conjugates are exemplified in structures 55, 59 and 63 of reaction schemes F through I.

The term "nucleobase" as used herein, refers generally to any moiety that includes within its structure a purine or pyrimidine, a nucleic acid, nucleoside, nucleotide, or any derivative of any of these, such as a "protected" nucleobase. Thus, the term nucleobase includes adenine, cytosine, guanine, thymidine, uridine, inosine, and the like, bases, nucleotides or nucleosides, as well as any base, nucleotide or nucleoside derivative based upon these or related structures.

A particular example of a useful nucleobase are the so-called antimetabolites that are based upon the purine or pyrimidine structure. These structures typically exert their biological activity as antimetabolites through competing for enzyme sites and thereby inhibiting vital metabolic pathways. However, in the context of the present invention, the inventors are employing the term "antimetabolite nucleobase" quite broadly to refer to any purine or pyrimidine-based molecule that will effect an anticellular, antiviral, antitumor, antiproliferative or antienzymatic effect, regardless of the underlying mechanism. Exemplary structures are shown in Table 1, and include the antimetabolites FU, AraC, AZT, ddI, xylo-GMP, Ara-AMP, PFA and LOMDP.

It is contemplated that rubyrin-nucleobase conjugates will have a wide variety of applications, including their use as carriers for the delivery of antiviral drugs to a particular body or even subcellular locale. In the case of antimetabolite nucleobases, it is known that many nucleobase antimetabolites can not be readily employed in therapy due to the fact that their charged nature inhibits their uptake by target cells, or otherwise inhibits or suppresses their unencumbered movement across biological membranes. Typically, this shortcoming is due to the presence of charged structures such as phosphates, phosphonates, sulfates or sulfonates on the nucleobase, which due to their charged nature prevents or inhibits their crossing of a biological membrane. It is proposed that the rubyrins of the present invention can be employed as transport agents for carrying such nucleobases across membranes, (whether the nucleobase is directly conjugated to the macrocycle or simply complexed with it). This point is elaborated in further detail in Sessler et al (1992)[24], incorporated herein by reference Generally speaking, in the context of rubyrin-nucleobase constructs designed for drug delivery it will usually be the case that one will employ only one or two nucleobase-containing substituents for each rubyrin macrocycle. Rubyrin derivatives with a single nucleobase are termed "ditopic receptors" whereas those with two nucleobases are termed "tritopic receptors". However, the invention is not limited to compounds containing one or two nucleobase units, indeed, mono- or di-substituted rubyrin-nucleobase conjugates may have any number of nucleobases or nucleobase oligomers or polymers attached. The ultimate number of such residues that are attached will, of course, depend upon the application. One may employ a rubyrin derivative with 10 or so bases attached to bind and transport complementary oligo- or poly-nucleotides. Of course, there is no limitation to the particular position(s) within the rubyrin macrocycle to which the nucleobase(s) may be attached to create a conjugate.

Further examples of rubyrin derivatives or conjugates encompassed by the present invention are rubyrin saccharide derivatives, wherein the macrocycle is appended to a saccharide-based unit, such as a sugar, sugar derivative or polysaccharide. The synthesis of rubyrin-saccharide compounds is described in Example IX and specific rubyrin saccharide conjugates are represented by structures 66, 68, 76 and 84 in reaction schemes J, K, M and O, respectively. A non-exhaustive, exemplary list of sugars which may be conjugated to rubyrin in this manner is set forth in Table 2. Of course, any sugar or modified sugar may be employed including sugars having additional phosphate, methyl or amino groups and the like. Moreover, the use of both D- and L-forms, as well as the $\alpha$ and $\beta$ forms are also contemplated. The use of sugars such as glucose, galactose, galactosamine, glucosamine and mannose is particularly contemplated. Rubyrin-saccharide conjugates are envisioned to be of use where one would like to control, or otherwise modify, the water solubility of the resultant rubyrin-based compound, for example, in exploiting its novel properties in connection with human or animal applications.

In still further embodiments, the invention concerns compositions which are composed of a rubyrin derivative in accordance with any one of the embodiments discussed above complexed to a second substance, wherein the second substance includes within its structure a negatively charged moiety. More particularly, the second substance will include a negatively charged component such as a chloride, phosphate, phosphonate, sulfate, or sulfonate moiety, of which, rubyrin-chloride ion complexes are a particular example.

In other preferred embodiments, the second substance will include a purine or pyrimidine, or an analog of either, within its structure. As mentioned above, these nucleobase structures include, for example, adenine, cytosine, guanine, thymidine, uridine and inosine; various antimetabolic or antienzymatic nucleobase compounds; and also oligo or polynucleotides such as DNA or RNA. Antimetabolic and antienzymatic compounds include those with antitumor, anticellular, antiproliferative and antiviral activity, examples of which are represented in Table 1.

In further related embodiments, the invention concerns a method for forming a complex between a rubyrin macrocycle and a negatively charged second substance, or selected agent. The method involves preparing a rubyrin or rubyrin analogue or conjugate, such as any one of the rubyrin derivatives as described above, and contacting this rubyrin or rubyrin derivative with a negatively charged substance or selected agent under conditions effective to allow the formation of a complex between the rubyrin macrocycle and the negatively charged substance.

This method is appropriate for binding, or complexing, a range of negatively charged substances or selected agents, such as for example, chloride ions and other halides, pseudohalides such as azide or cyanide anions, and anionic clusters such as ferricyanide. The complexing of phosphate-containing compounds, including, simple alkyl or aryl phosphates, nucleotides, oligo- and polynucleotides, such as DNA, RNA and anti-sense constructs, and nucleotide analogues is particularly contemplated. Even more preferable, is the complexing of antiviral compounds such as phosphonate derivatives and simple species such as the pyrophosphate derivatives PFA and COMDP; the antiviral agents of FIG. 9A, structure b; FIG. 9B, structure e; FIG. 9C; FIG. 9D; FIG. 9E; and FIG. 9F; and Table 1, and particularly, acyclovir monophosphate, Xylo-GMP, Ara-AMP. Here, as throughout this invention, a key embodiment is the high basicity of the rubyrin or pseudo rubyrin core, which allows this class of compounds and its derivatives to act as vastly improved anion chelators or carriers in comparison to expanded porphyrins such as sapphyrins or any other extant system.

Still further methodological embodiments concern methods for the cellular transport of a given substance, generally a negatively charged substance. This may be employed as a means of, for example, successfully introducing a negatively charged substance into a cell, or alternatively, as a means of facilitating the removal of a negatively charged substance from a cell. To achieve this, one would prepare a rubyrin macrocycle in accordance with the present invention, contact the macrocycle with the negatively charged substance under conditions effective to allow complex formation, and then simply contact the cell, either in vitro or in vivo, with the macrocycle-bound substance.

Any one of a variety of negatively charged substances may be delivered to a cell, including a cell within an organism, in this manner. The delivery of polynucleotides, including anti-sense constructs, and nucleotide analogues, such as antiviral compounds, is particularly envisioned. One example concerns the introduction of a rubyrin-complex composition which includes an antiviral antimetabolic or antienzymatic compound into a cell suspected of being a virally infected target cell. Another example is the introduction of an antitumor antimetabolic or antienzymatic compound into a cell suspected of being a tumor or proliferating cell.

Of course, it is contemplated that such target cells may be located within an animal or human patient, in which case an effective amount of the complex, in pharmacologically acceptable form, would be administered to the patient. Generally speaking, it is contemplated by the inventors that useful pharmaceutical compositions of the present invention will include the selected rubyrin derivative in a convenient amount that is diluted in a pharmacologically or physiologically acceptable buffer, such as, for example, phosphate buffered saline. The route of administration and ultimate amount of material that is administered to the patient or animal under such circumstances will depend upon the intended application and will be apparent to those of skill in the art in light of the examples which follow. Preferred routes of administration will typically include parenteral or topical routes.

The capacity of rubyrin and analogues thereof to effect specific into-cell transport of anti-viral compounds is contemplated to be of use against a wide variety of debilitating diseases such as AIDS, herpes, hepatitis and measles. As a mediator of DNA import, rubyrins may conceivably be employed in the treatment of any disease in which the delivery of an oligonucleotide or DNA fragment would be advantageous, such as in supplying a functioning gene, or in inhibiting an aberrant gene, for example, by employing an antisense DNA construct. As discussed above, the larger size, high basicity, and relative ease with which rubyrins may be protonated, renders them particularly effective molecules for use in anion transport.

Additionally, certain rubyrins with advantageous chloride ion transporting properties may be employed as synthetic carriers capable of facilitating out-of-cell diffusion of chloride anions, and are therefore contemplated for use as therapeutic agents for the treatment of cystic fibrosis.

BRIEF DESCRIPTION OF THE DRAWINGS

FIG. 1A, porphine; FIG. 1B, smaragdyrin; FIG. 1C, sapphyrin; FIG. 1D, pentaphyrin; FIG. 1E, hexaphyrin; FIG. 1F, superphthalocyanine. Compounds in FIG. 1B–FIG. 1F are all represented in their generalized substituent-free forms.

FIG. 2A, rubyrin (29,30,31,32,33,34-hexaazaheptacyclo[24.2.1.1$^{2,5}$.1$^{7,10}$.1$^{12,15}$.1$^{16,1}$ 9.1$^{21,24}$]tetratriaconta-1,3,5,7(31),8,10,12,14,16,18,20,22,24(34) ,25,27-pentadecaene); FIG. 2B and FIG. 2C, the same overall connectivity and same number of non-hydrogen atoms as rubyrin, but different number of total electrons contained within the y-electron periphery. FIG. 2D–FIG. 2F represent more general versions of the rubyrins of the present invention. In these structures, $A_1$ and $A_2$ may be nitrogen, oxygen or sulphur. The substituents $R_1$–$R_6$ and $X_1$–$X_4$ may be separately and independently H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether, substituted amide; or may be of the formula $(CH_2)_n$—A—$(CH_2)_m$—B. In this formula, n and m are integers <10 or zero; A may be $CH_2$, O, S, NH or $NR_7$, wherein $R_7$ may again be any of the above groups; and B will be a chosen or selected functional group. Preferred groups for B are contemplated to be nucleobases, modified nucleobases, oligonucleotides, sugars, sugar derivatives or polysaccharides; however, other suitable groups include, for example, metal chelating groups, alkylating agents, steroids, steroid derivatives, amino acids, peptides, polypeptide, rubytin, rubyrin derivative, polymeric rubytin, other macrocyclic compounds such as sapphyrins or texaphyrins, polymeric matrices or solid supports.

FIG. 9A, structure a acyclovir (9[(2-hydroxyethoxy)methyl]-9H-guanine); FIG. 9A, structure b, phosphorylated form after viral thymidine kinase action; FIG. 9A, structure c, active, ionic triphosphate nucleotide-like species; FIG. 9B, structure d, Xylo-G (9-($\beta$-D-xylofuranosyl)guanine); FIG. 9B, structure e, phosphorylated form; FIG. 9C and FIG. 9D, anti-HSV and anti-HIV phosphonate derivatives; FIG. 9E, the pyrophosphate derivative PFA; and FIG. 9F, the pyrophosphate derivative COMDP.

DETAILED DESCRIPTION OF THE PREFERRED EMBODIMENTS

Figure 1C:
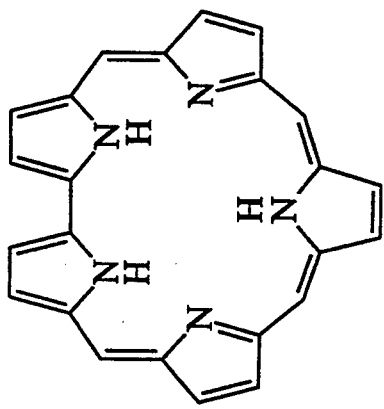
FIG. 1A–FIG. 1F. Porphyrins and expanded porphyrins (large pyrrole-containing macrocyclic porphyrin analogues).
Figure 1F:
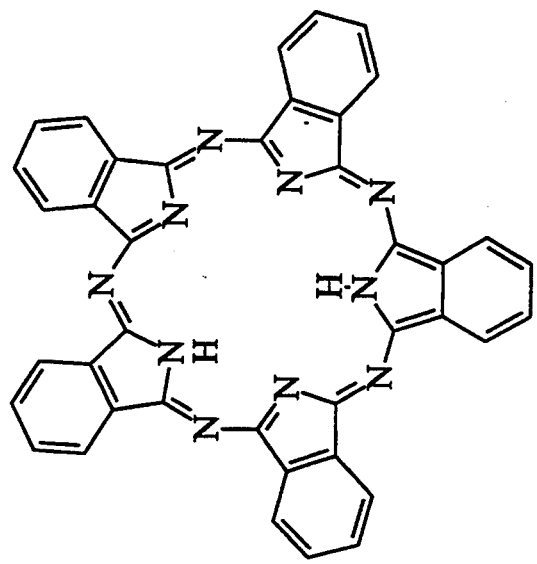
Figure 1B:
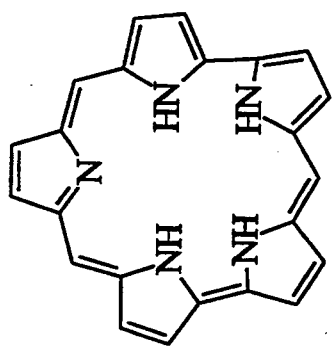
Figure 1E:
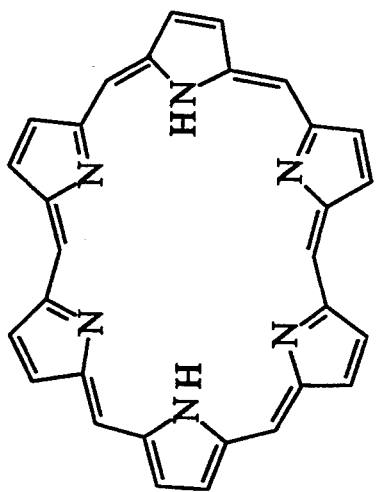
Figure 1A:
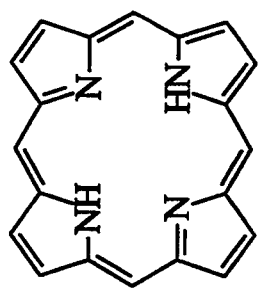
Figure 1D:
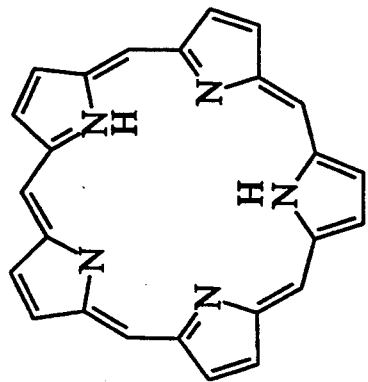

Expanded porphyrins[1] are large pyrrole-containing macrocyclic analogues of porphyrins (e.g. porphine, FIG. 1A) of which a number are known[1-17]. Prior to the present invention, only a few fully conjugated examples had been reported that contain more than four pyrrolic subunits, these are the smaragdyrins[2,3] sapphyrins[2-6], pentaphyrins[7,8] hexaphyrins[9] and superphthalocyanines[10], represented in their generalized substituent-free forms as structures FIG. 1B–FIG. 1F.

For the most part, the chemistry of the above-mentioned expanded porphyrin systems has been communicated in only the briefest fashion. In fact, at present, structural information is available only for derivatives of sapphyrin (e.g. FIG. 1B)[4,5] and pentaphyrin (e.g. FIG. 1C)[8] in the all-pyrrole series. In particular, no structurally characterized hexapyrrolic macrocycles have previously been reported. Given this paucity of information, the inventors considered that the preparation and study of new hexapyrrolic systems would be of interest. It was reasoned that such studies would generate important information with regards to ring size, aromaticity, and effective macrocycle stability.

As mentioned above, it is known that the effectiveness of various antiviral compounds, such as nucleotide analogues, is limited in vivo due to their inability to traverse lipophilic cell membranes[25,26]. In fact, this has rendered many potential antiviral agents, including, for instance, the anti-HIV agent, Xylo-G (FIG. 9B, structure d), largely or completely inactive[27]. A major aim of the present study was therefore to provide a means of transporting active monophosphorylated forms of these putative drugs (such as in FIG. 9B, structure e) into cells, which would allow a wide range of otherwise inactive compounds to be used against viral infections.

Cystic fibrosis (CF) is the most common lethal genetic disease in Caucasians, striking about one in 2,500 U.S. infants[68]. This disease, which is becoming increasingly well understood as the result of the recent identification of the responsible gene mutation, is characterized by an inability to produce functional chloride anion channel proteins (the cystic fibrosis transmembrane regulator or CFTR protein)[55-58] and by an inability to effect sufficient chloride and fluid excretion from, among others, pulmonary epithelial cells. This, in turn, leads to a thick build up of mucous deposits in the lungs and to a higher than normal susceptibility towards fatal pulmonary infections. It is these infections, often of the *Pseudomonas aeruginosa* type, that are generally the causative agents of cystic fibrosis related death.

At present, the established treatment protocols for cystic fibrosis involve treating these secondary infections with appropriate antibiotics, as well as adjusting diet and removing by physical means the deleterious build up of mucociliary secretions[59]. Unfortunately, these methods have not succeeded in prolonging the median life expectancy of cystic fibrosis patients past the age of 25[59]. Thus, considerable current effort is being devoted to developing treatments that operate by attacking the underlying cause of disease. Here, a variety of approaches have been explored. These range from attempts at gene therapy (incorporating the normal, wild-type cystic fibrosis gene into epithelia cells) to the administration of agents that restore electrolyte balance either by opening up other non-CFTR dependent chloride anion channels or by inhibiting cellular uptake of sodium cations. Unfortunately, the viability of this latter electrolyte balance restoration approach still remains limited.

In common with the problems associated with antiviral administration, the existence of a specific, in this case chloride-selective, anion carrier could be of prime clinical utility in terms of treating a major public health problem. It was the inventors aim in conducting the present study to develop a range of compounds that would allow both of these medically important anion transport problems to be addressed.

In defining these objectives, the biological importance of inter-linked phosphate and halide transport was also considered. Transport of one anionic species, achieved at the expense of the other, could confer considerable clinical advantage in the case of purely synthetic nucleotide carriers. It would allow one to achieve intracellular delivery of an antiviral agent without creating a deleterious osmotic imbalance. Generally, for CF treatment, it is contemplated that concurrent out-of-cell chloride and sodium ion transport would be the most effective trigger for subsequent fluid excretion. However, simultaneous into-cell diffusion of, e.g., phosphorylated entities could be used to overcome problems associated with out-of-cell chloride anion transport in the case of unfavorable chloride anion concentration gradients.

Despite the previous preparation of several halide-binding receptors, none of these may be used as clinical chloride anion transporters. For instance, ammonium bicycles bind chloride anions with more specificity than bromide and iodide[60], but only at low pH and with very low affinity constants. Cryptand cations were found to bind halide anions with high affinity and selectivity, and receptors with near-exclusive halide specificities have been reported[61,62]. Unfortunately, these systems suffer from a serious drawback as far as anion transport is concerned: They rely on a high net positive charge to effect the coordination of a single anion. As a result, the supramolecular anion-to-receptor complex formed upon anion binding is still highly charged and relatively insoluble in organic media. Thus, through-membrane transport is only achieved if a large, organic soluble "helper anion" is added to the halide-bearing transport medium[63].

This same problem of excess charge effects all the other known polyammonium halide anion receptors and all halide anion chelands of the polyguanidinium type and pyridinium-based cyclophane class[64]. Such considerations of charge are of lesser concern in the case of the newer metal- and metalloid-derived anion receptors[6-5-69]. In this instance, however, questions of heavy metal toxicity cloud considerations of possible clinical utility. Thus, the need for good, neutralizing chloride anion carriers remains.

Regarding nucleoside transport, in preliminary work, the present inventors employed triisopropylsilyl (TIPS) substituted (phosphate-free) nucleosides. It was found that efficient and selective through-membrane transport of non-charged nucleoside analogues could be achieved by using the complementary TIPS derivatives as carriers[70]. Not surprisingly, however, these same TIPS derivatives proved completely ineffective as transport agents for the analogous phosphate-containing nucleotide derivatives. Thus, whilst confirming the viability of a base-pairing approach to selective nucleotide recognition, this work served to highlight further the need for an organic soluble, neutralizing, phosphate binding group.

In this light, the inventors reasoned that ditopic receptors capable of recognizing both the anionic phosphate and the neutral portions of nucleotide derivatives, such as the purine or pyrimidine moieties, may be particularly advantageous in the transport of anti-viral compounds. To synthesize such compounds, the inventors realized that they had to consider the independent development of molecular recognition strategies for the complexation of two very different kinds of substrates (charged anionic and neutral nucleobase) and then the subsequent co-combination so as to provide a single receptor bearing both kinds of binding subunits. Further and significant problems to be overcome were those associated with creating a molecule which has the capacity to bind anions and yet the ability to retain overall supramolecular charge neutrality.

In initial studies using expanded porphyrins, the inventors determined sapphyrin to be ineffective as a phosphate compound transporter, but pentaphyrin to be capable of transporting GMP at pH 6. Unfortunately, not only was this process found to be slow, but also extensively inhibited by the addition of chloride anion. In addition, sapphyrin and anthraphyrin[18a,b] were found to be capable of halide anion transport, but only in those pH regimes where they remain monoprotonated. Also, in both cases the anion that was less well bound was found to be transported at the greatest rate (i.e. chloride by sapphyrin and fluoride by anthraphyrin)[18a,b].

Figure 2A:
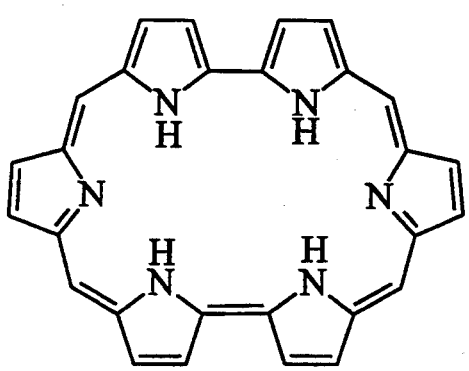
FIG. 2A–FIG. 2F. Rubyrin and rubyrin analogues.

The search for an anion-binding compound with the ability to retain overall supramolecular charge neutrality, led the inventors to synthesize and characterize a novel class of hexapyrrolic expanded porphyrins, represented by FIG. 2A, and substituted derivatives thereof. FIG. 2A corresponds to the macrocyclic system 29,30,31,32,33,34-hexaazaheptacyclo[24.2.1.1$^{2,5}$.1$^{7,10}$.1$^{12,15}$.1$^{16,19}$.1$^{21,24}$]tetratriaconta-1,3,5,7(31),8,10,12,14,16,18,20,22,24(34),25,27-pentadecaene [19]. Also contemplated by the invention are macrocyclic analogues of FIG. 2A, such as FIG. 2B and 2C, which have the same overall connectivity and same number of non-hydrogen atoms but which differ from the structurally characterized 26 n-electron prototypes by the number of total electrons contained within the π-electron periphery.

Figure 3:
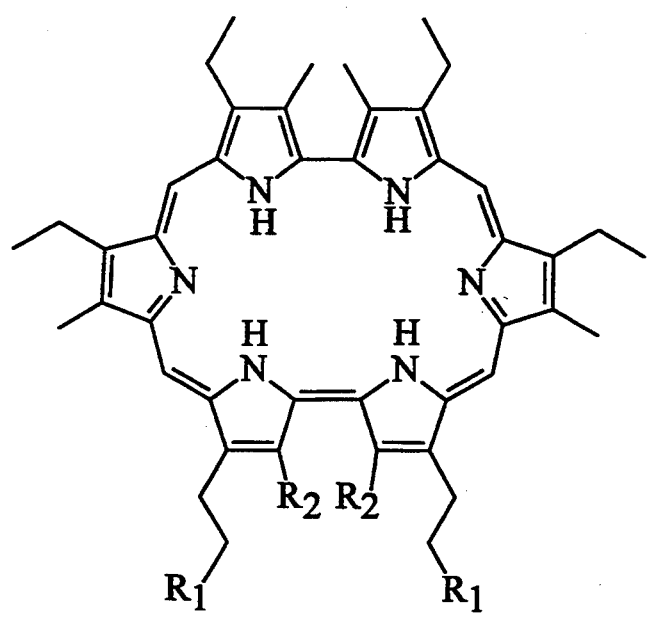
FIG. 3. Structure 10a, 4,8,13,18,23,27-hexaethyl-3,9,14,17,22,28-hexamethyl-29, 30,31,32,33,34-hexaazaheptacyclo[24.2.1.1$^{2,5}$.1$^{7,10}$.1$^{12,15}$.1$^{16,19}$.1$^{21,24}$]tetratriaconta-1,3,5,7(31),8,10,12,14,16,18,20 ,22,24(34),25,27-pentadecaene (4,8,13,18,23,27-hexaethyl-3,9,14,17,22,28-hexamethylrubyrin); structure 10b, the counterpart wherein $R_1$=$CH_3$ and $R_2$=H.

Substituted derivatives of FIG. 2A are red in dilute organic solution, and the trivial name "rubyrin" (from the Latin rubeus) has therefore been assigned to this new class of expanded porphyrins. It will be this trivial nomenclature that is used throughout the present application. Thus, for instance, 4,8,13,18,23,27-hexaethyl-3,9,14,17,22,28-hexamethyl-29,30,31,32, 33,34-hexaazaheptacyclo [24.2.1.1$^{2,5}$.1$^{7,10}$.1$^{12,15}$.1$^{16,19}$.1$^{21,24}$]tetratriaconta-1,3,5,7(31),8,10,12,14,16,18,20,22,24(34) ,25,27-pentadecaene (structure 10a, FIG. 3), is named as 4,8,13,18,23,27-hexaethyl-3,9,14,17,22,28-hexamethylrubyrin.

The rubyrin and rubyrin analogues of the present invention are characterized by the capacity to bind anions and yet the ability to retain overall supramolecular charge neutrality. A particular advantage to rubyrin molecules is their large size. This property renders rubyrins easier to protonate than other macrocycles and makes them considerably more effective at anion recognition and transport than any other classes, including the sapphyrins. The increased basicity of rubyrin relative to sapphyrin is thus of considerable importance and represents a significant advance relative to the existing art.

The synthesis of the diprotonated form of 4,8,13,18,23,27-hexaethyl-3,9,14,17,22,28-hexamethylrubyrin, structure 17, contains two key steps. The first involves the acid catalyzed condensation between the bis-α-free bipyrrole 11$^{4a}$ and the acetoxy activated pyrrole 12$^{20}$, to give the protected tetrapyrrolic derivative 13. Standard near quantitative debenzylation then gave the diacid 14, which was used directly in an acid-catalyzed [4]+[2] MacDonald-type[21] oxidative condensation with the readily available[4a] diformyl bipyrrole, 15. The second step, condensation and air oxidation, ultimately provides the diprotonated rubyrin derivative 17a. Washing either the purified ditosylate salt 17a, or the crude reaction mixture, with aqueous 10% hydrochloric acid then produced the more crystalline dihydrochloride derivative 17b. Carrying out a similar sequence starting with diformyl bipyrrole 16$^{22}$ gave in analogy salts Lea 18a and 18b in similar good yield.

Compounds 10a and 10b are synthesized from compounds 17 and 18. In both cases, careful neutralization of dichloromethane solutions, achieved by washing with aqueous sodium bicarbonate, was found to give rise to the neutral, free-base forms, corresponding to structures 10a and 10b (FIG. 3) in the case of salts 17 and 18, respectively.

Figure 11:
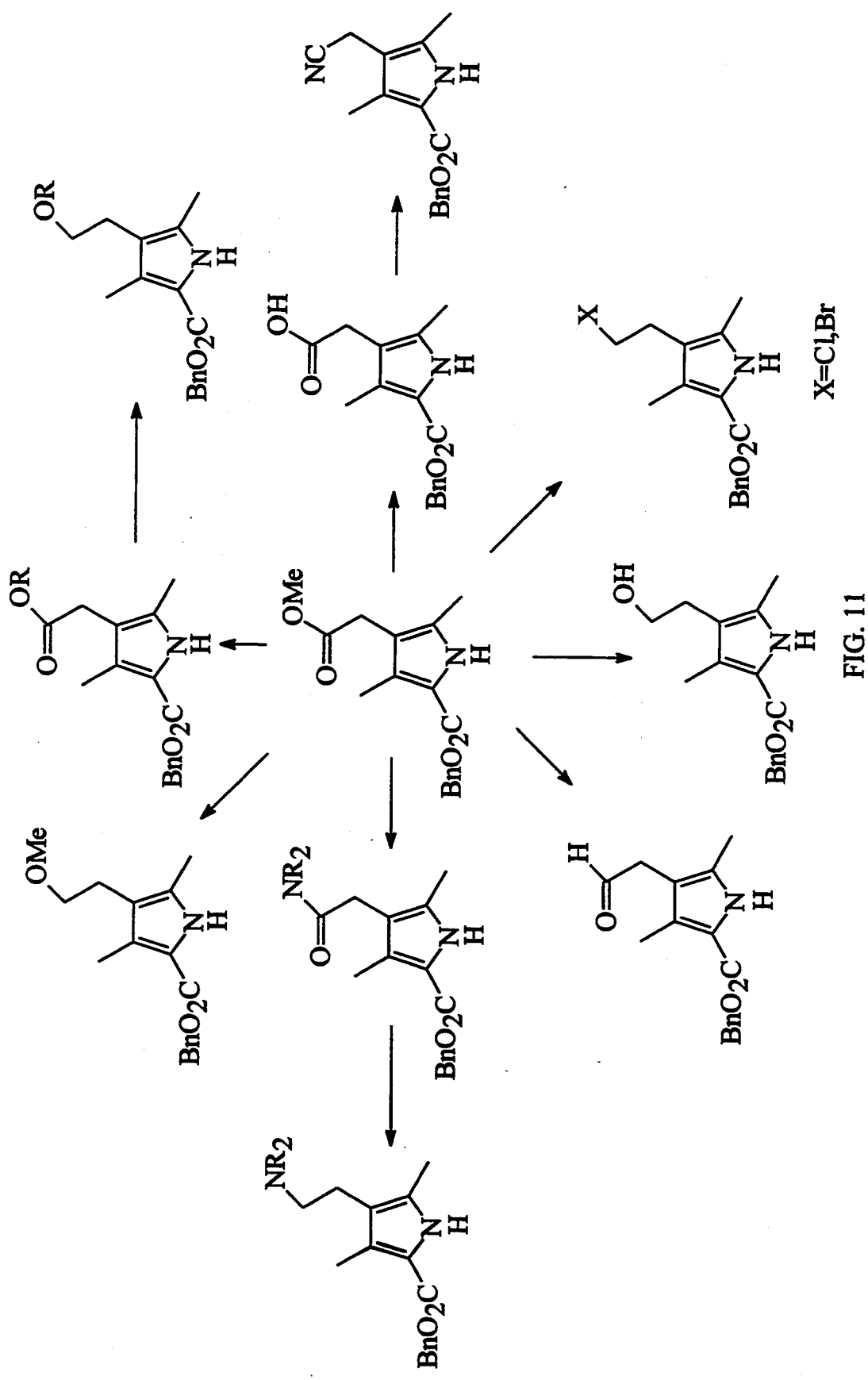
FIG. 11. Examples of functional group manipulation in β-substituted pyrroles as applied to the synthesis of rubyrins and rubyrin analogues.
Figure 12A:
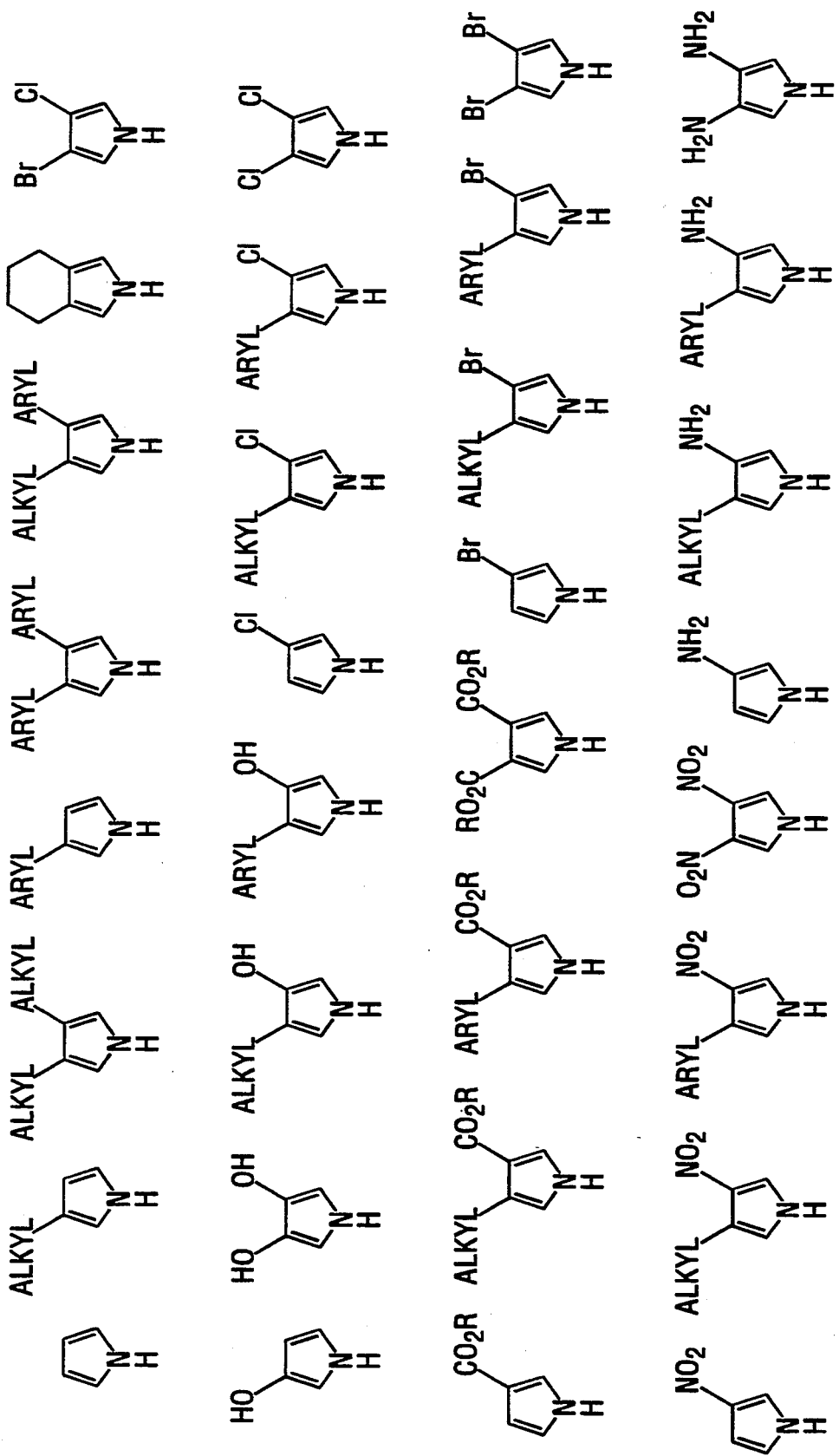
FIG. 12A and FIG. 12B. Examples of starting pyrroles for use in the synthesis of rubyrins and rubyrin analogues.
Figure 12B:
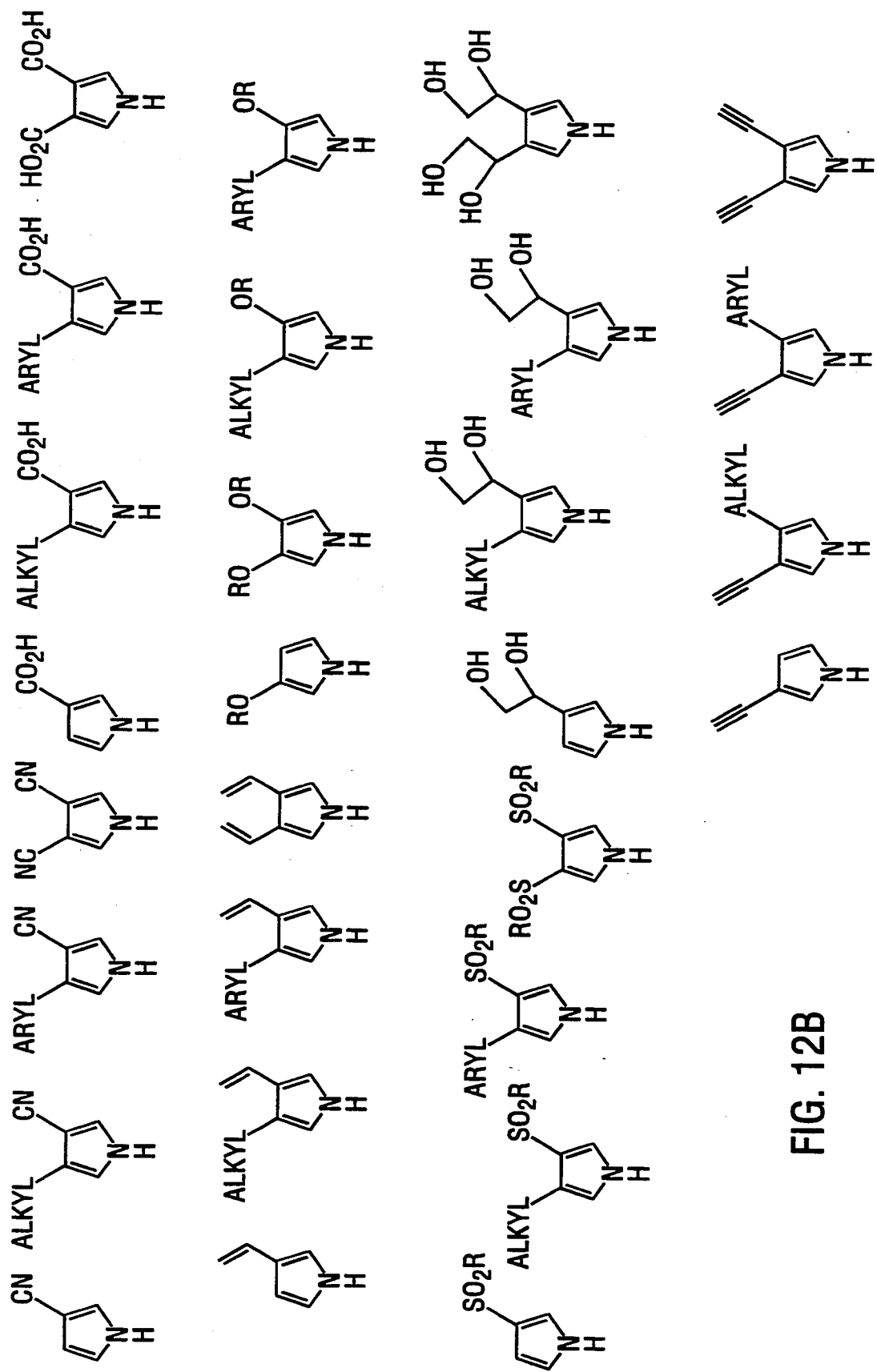

Additionally, several other rubyrin analogues are contemplated by the present invention. Different combinations of bipyrroles and pyrroles, for example see FIG. 11, 12A and 12B, may be employed both in the first and second condensation steps to yield a variety of different macrocyclic products. The generation of further rubyrin analogues is particularly described in Example VII, and represented in reaction schemes A through E. A range of compounds with a wide variety of alkyl and/or aryl substituents in the meso and/or β-pyrrolic positions, as exemplified by structures 27, 35, 40 and 47, thus fall within the scope of the present invention.

Furthermore, rubyrin analogues employing heteroatoms are also within the scope of the present invention. In particular, different combinations of oxygen and sulphur atoms, either alone, in combination with nitrogen, or in combination together, are contemplated. The synthesis of rubyrin analogues in which two, four, or even six, of the nitrogen atoms have been replaced by oxygen or sulfur is described in Example X, and compounds in accordance with those represented by structures 20–24 in FIG. 6 and structures 87, 92, 99 and 104 in reaction scheme P through reaction scheme S, are therefore encompassed by the present invention.

The inventors contemplate that rubyrin itself and the unconjugated rubyrin analogues of the present invention will be of use as drug delivery agents. It is contemplated that they will find utility in mediating the cross-membrane transport of negatively charged compounds or molecules, including halides, pseudohalides, such as azide or cyanide anions, or anionic clusters such as ferricyanide. The anion carrying properties of rubyrins make them ideal candidates for the development of synthetic carriers capable of facilitating out-of-cell diffusion of chloride anions, and hence for use as therapeutic agents for the treatment of cystic fibrosis.

Figure 9A:
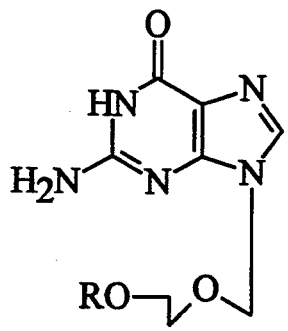
FIG. 9A–FIG. 9F. Structures of anti-viral and potentially anti-viral compounds.
Figure 9B:
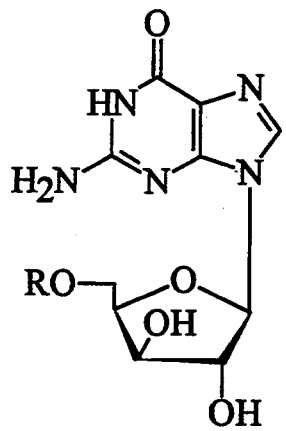
Figure 9C:
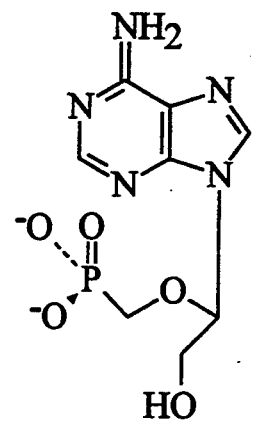
Figure 9D:
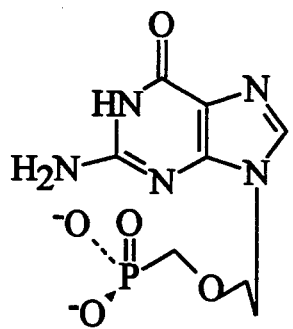
Figure 9E:
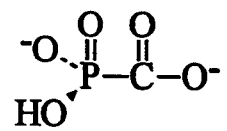
Figure 9F:
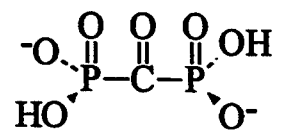

Importantly, rubyrin and analogues thereof are contemplated for transporting phosphate-containing compounds into cells. Phosphate-containing compounds which may be transported in this manner include, for example, simple alkyl or aryl phosphate, nucleotides such as AMP or GMP, oligonucleotides and DNA or RNA, including anti-sense DNA or RNA constructs, and more particularly, antiviral compounds such as those depicted in FIG. 9A, structure b; FIG. 9B, structure e; FIG. 9C; FIG. 9D; FIG. 9E; and FIG. 9F, Table 1, and equivalents thereof.

TABLE 1

| MODIFIED NUCLEOSIDE/NUCLEOTIDE ANALOGUE ANTI-METABOLITES | |
|---|---|
| AraC | Erythrohydroxynonyladenine |
| AraAMP | Floxuridine |
| Azaribine | Fluorouracil (5-FU) |
| Azathioprine | Idoxuridine |
| Azauridine | LOMPD |
| AZT | Mercaptopurine |
| Bromodeoxyuridine | PFA |
| Chlorodeoxyuridine | Thioguanine |
| Cytarabine | Trifluoromethylde-oxyuridine |
| Deoxyuridine | Xylo-GMP |
| DideoxyInosine DDI | |

Any one of a variety of antiviral agents may be delivered to a cell using rubyrin or a rubyrin analogue in accordance herewith. These agents include, for example, the anti-HSV and anti-HIV agents acyclovir monophosphate, Xylo-GMP, Ara-AMP, and/or phosphonate derivatives that also have documented anti-HSV and anti-HIV activity in vitro[28,29] (e.g. FIG. 9C and FIG. 9D), and simple species such as the pyrophosphate derivatives PFA (FIG. 9E) and COMDP (FIG. 9F) that have demonstrated anti-HIV reverse transcriptase activity in cell-free media[30].

As mentioned above, the large size, increased basicity and ease of protonation of rubyrins makes this class of macrocycles considerably more effective at the recognition and transport of anions than other classes of molecules. The capacity of rubyrin, and analogues thereof, to effect specific into-cell transport of anti-viral compounds is contemplated to be of advantageous use against a wide variety of debilitating diseases, including, for example, herpes, hepatitis, measles, and AIDS. Such diseases are of major medical and economic importance with AIDS being an international health problem and even measles claiming over 100,000 lives per year world-wide[26].

Figure 10:
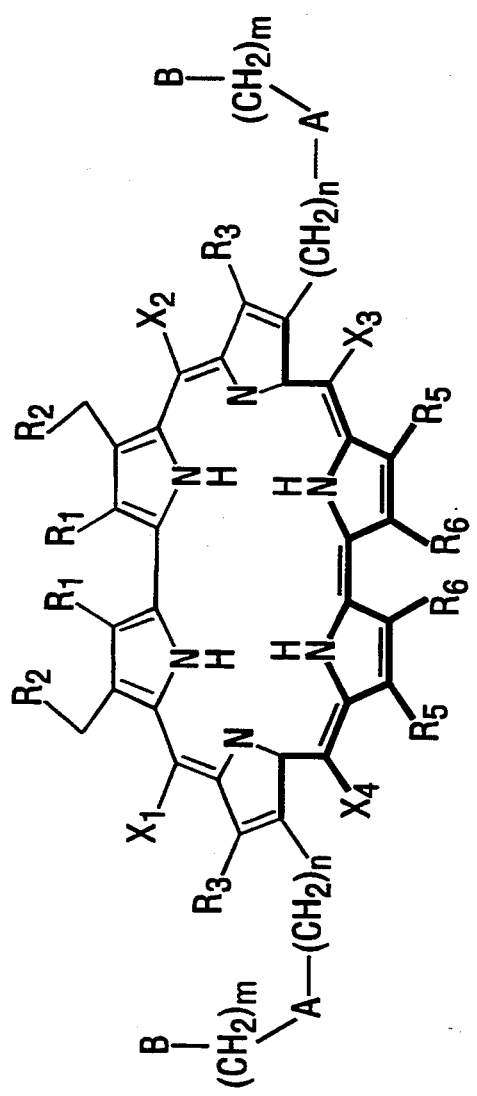
FIG. 10. Rubyrin nucleobase derivatives—B=one or more nucleobases, derivatives, analogues or protected nucleobases; STRUCTURE IV—mono-substituted; STRUCTURE V—disubstituted. Rubyrin nucleobase conjugates may be of the mono- or di-substituted forms, as represented by the general structures IV and V. Mono-substituted rubyrin-nucleobase conjugates may contain, but are not limited to, a single nucleobase unit, when they are termed ditopic rubyrin receptors. Di-substituted rubyrin-nucleobase conjugates containing two nucleobase units are termed tritopic rubyrin receptors. In structures IV and V, the groups $R_1$–$R_6$ which do not contain a nucleobase functional unit, and groups $X_1$–$X_4$, may be H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether and substituted amide. At least one of the R groups will be of the formula $(CH_2)_n$—A—$(CH_2)_m$—B, wherein A may be $CH_2$, O, S, NH or $NR_7$, and $R_7$ may be any of the groups listed above and B may be one or more nucleobases, nucleobase derivatives or protected nucleobases. Conjugation of a nucleobase to a rubyrin derivative to form a mononucleobase rubyrin conjugate may be via any of the R or X groups. Conjugation of the two separate nucleobases to a rubyrin derivative to form a dinucleobase rubyrin conjugate may also be via any two of these groups, however, it is contemplated that the creation of a symmetrical molecule will generally be preferred. The rubyrin nucleobase derivatives may include any purine or pyrimidine nucleobase, such as cytosine, guanine, thymidine, adenine, uridine or inosine. Alternatively, they may include modified versions of any of these, such as those listed in Table 1, or chemically modified nucleobases such as "protected" bases including, for example, a protecting group on the amino group of the nucleobase, such as, for example, 9-fluorenylmethylcarbonyl, benzyloxycarbonyl, 4-methoxyphenacyloxycarbonyl, t-butyloxycarbonyl, 1-adamantyloxycarbonyl, benzoyl, N-triphenylmethyl, N-di-(4-methoxyphenyl)phenylmethyl.

Furthermore, the inventors reasoned that the rubyrin compounds of the present invention may be rendered even more useful as nucleotide transporters if one or more nucleobase recognition units were to be "appended" directly onto the phosphate-chelating macrocyclic core. This would impart a further degree of nucleotide specificity to binding and transport reactions. Accordingly, rubyrin-nucleobase conjugates which have been derivatized by the addition of one or more nucleobase compounds, as represented by FIG. 10, form an important aspect of the present invention. Rubyrin derivatives with one nucleobase per rubyrin molecule are referred to as ditopic receptors, whereas those doubly-functionalized rubyrin derivatives with 2 nucleobases per molecule are termed tritopic receptors.

Rubyrin mononucleobase derivatives may include any of the naturally-occurring purine or pyrimidine nucleobases, namely, cytosine, guanine, thymidine, adenine, uridine or inosine. Equally, they may include modified versions of any of these, such as the heterocyclic components of those nucleoside/nucleotide analogues listed in Table 1. Also included within the invention are the rubyrin mononucleobase derivatives including chemically modified nucleobase such as "protected" bases. Protecting groups are used to protect reactive groups, such as amino and carboxyl groups, from inappropriate chemical reactions. Rubyrinnucleobase conjugates with protected bases include, for example, conjugates wherein one or more base has a protecting group, such as 9-fluorenylmethylcarbonyl, benzyloxycarbonyl, 4-methoxyphenacyloxycarbonyl, t-butyloxycarbonyl, 1-adamantyloxycarbonyl, benzoyl, N-triphenylmethyl or N-di-(4methoxyphenyl)phenylmethyl on the amino group of the nucleobase.

The present inventors contemplate many different chemical means by which to connect nucleobases to rubyrin macrocycles. Various spacers may be used for the connection, such as, for example, oligomethylene bridges with terminal amino, or hydroxy function, which allow formation of amide and ester bond for the connection of the rubyrin and nucleobase units. This bridge may also be modified, e.g., by the reduction of the amide bond to give the amine function. Specific examples of the synthesis of rubyrin-nucleobase conjugates are described in Example VIII and the resultant compounds are represented by structures 51, 55, 59 and 63 of reaction schemes F through I.

Rubyrin nucleobase conjugates would be useful as antiviral adjuvants, capable of binding and solubilizing nucleotides and of effecting their selective through-membrane transport at or near physiologic pH. Rubyrin nucleobase conjugates with appended oligonucleotides are also contemplated by the present invention, and would be of use in binding and transporting oligo- or polynucleotides, including antisense constructs, into cells. As a mediator of DNA import, rubyrins may conceivably be employed in the treatment of any disease in which the delivery of an oligonucleotide or DNA fragment would be advantageous, such as in supplying a functioning gene, or in inhibiting an aberrant gene, for example, by employing an antisense DNA construct.

Another class of rubyrin derivatives or conjugates contemplated by the present inventors are the rubyrin saccharide derivatives which comprise a rubyrin macrocycle conjugated to a sugar, sugar derivative or polysaccharide. The synthesis of rubyrin-saccharide compounds, as represented by structures 66, 68, 76 and 84 in reaction schemes J, K, M and O, respectively, is described in Example IX. It will be understood that any one of a variety of individual sugar units, such as those set forth in Table 2, or polymers thereof, may be conjugated to rubyrin in accordance herewith. Table 2 is intended to include modified versions of the sugar units, such as sugars having additional phosphate, methyl or amino groups and the like, and also includes D- and L-isomers and $\alpha$ and $\beta$ forms.

TABLE 2

| Examples of Sugars and Sugar Derivatives | |
|---|---|
| Ribose | Fructose |
| Arabinose | Sorbose |
| Xylose | Tagatose |
| Lyxose | Fucose |
| Allose | Methylglucoside |
| Altrose | Glucose 6-phosphate |
| Glucose | N-Acetylgalactosamine |
| Mannose | N-Acetylglucosamine |
| Gulose | Sialic Acid |
| Idose | |
| Galactose | |
| Talose | |
| Ribulose | |
| Xylulose | |
| Psicose | |

In addition to the rubyrin analogues described above and the nucleobase and saccharide conjugates, it will be appreciated that a variety of other substituents, of desirable chemical function, may be appended to a functionalized rubyrin moiety to create a rubyrin-based conjugate. The present inventors contemplate the synthesis of rubyrin conjugates including, for example: metal chelator moieties such as EDTA, EGTA, 1,10-phenanthralene, DTPA, DOTA, crown ether, azacrown, catecholate and ethylene diamine; alkylating agents such as ethylene diamine, epoxide and bromoacetamide; steroids and steroid derivatives; amino acids, peptides and polypeptides; other rubyrins, rubyrin derivatives, polymeric rubyrin, or other macrocyclic compounds such as sapphyrins, texaphyrins or derivatives thereof; and polymeric matrices or solid supports such as polymers, glasses, agarose, polyacrylamide, controlled pore glass, silica gel, polystyrene and sepharose.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

SYNTHESIS OF RUBYRIN STRUCTURES 17a and 17b

Figure 4A:
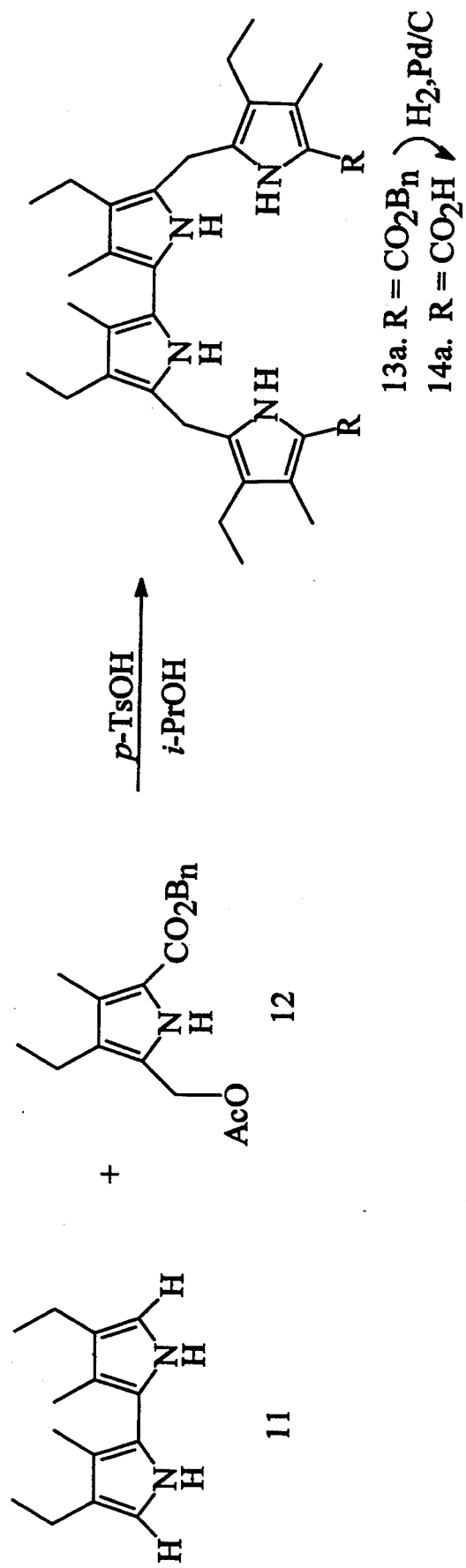
FIG. 4A and FIG. 4B. Reaction scheme for the synthesis of structure 17a and 17b, the diprotonated form of 4,8,13,18,23,27-hexaethyl-3,9,14,17,22,28-hexamethylrubyrin, also demonstrating structures 11–16; 17a, 17b, 18a and 18b.
Figure 4B:
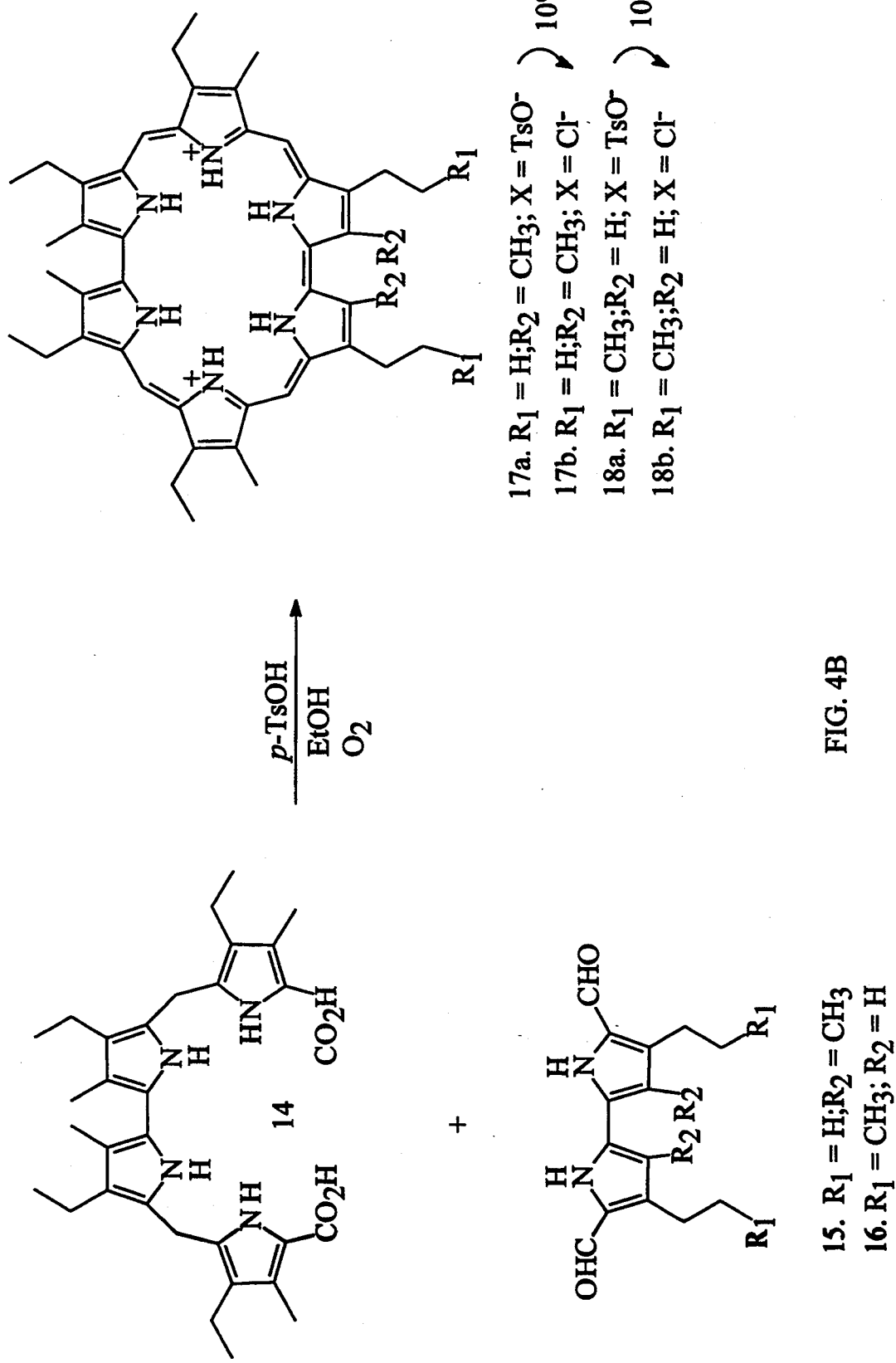

The synthesis of the diprotonated form of 4,8,13,18,23,27- hexaethyl-3,9,14,17,22,28-hexamethyl-rubyrin, structure 17, is shown in FIG. 4A and FIG. 4B. It contains two key steps. The first involves the acid catalyzed condensation between the bis-$\alpha$-free bipyrrole 11[4a] and the acetoxy activated pyrrole 12. [20] This reaction, which was carried out in analogy to earlier syntheses of symmetric tripyrranes[16d], gave the protected tetrapyrrolic derivative 13 in approximately 66% yield.

In more detail, compounds 11 (3.72 g, 17.2 mmol) and 12 (10.9 g, 34.5 mmol) were combined in a round bottom flask with absolute isopropyl alcohol (140 ml) and the resulting mixture heated at 80° C. to effect complete dissolution. p-Toluenesulfonic acid monohydrate (30 mg) was then added and the resulting green solution heated at reflux for 10 hours under nitrogen. The resulting suspension was then cooled to room temperature and placed in a refrigerator for one hour. Filtration, washing with cold ethanol, and drying in vacuo then afforded compound 13 as a fine, off-white powder (8.24 g, 66%), which could be further purified by recrystallization from $CH_2Cl_2$/MeOH. m.p.=163–166 ° C.; $^1$H NMR (300 MHz, $CDCl_3$): $\delta$=0.83 (t, 6 H, $CH_2CH_3$), 1.10 (t, 6 H, $CH_2CH_3$), 2.02 (s, 10 H, $CH_3$ and $CH_2CH_3$), 2.12 (s, 6 H, $CH_3$), 2.46 (m, 4 H, $CH_2CH_3$), 3.70 (bs, 6 H, pyrrole-$CH_2$ and $CH_2Ph$), 4.55 (bs, 2 H, $CH_2Ph$), 6.85 (m, 4 H, aromatic), 7.21 (m, 6 H, aromatic), 9.89 (bs, 2 H, NH), 10.98 (bs, 2 H, NH); $^{13}$C NMR (75.5 MHz, $CDCl_3$): $\delta$=11.20, 11.30, 15.21, 15.61, 16.86, 18.20, 22.34, 65.91, 113.97, 117.12, 120.76, 121.29, 123.36, 123.51, 126.53, 126.88, 127.64, 127.82, 133.80, 135.97, 164.48; HRMS (CI): m/z 726. 4142 (M+), calcd for $C_{46}H_{54}N_4O_4$ 726.4145 ($\pm$0.0003).

Standard near quantitative debenzylation of 13 then gave the diacid 14. This was achieved by dissolving the dibenzyl ester 13 (0.24 g, 0.33 mmol) in dry THF (100 ml) and subjecting to hydrogenation over 10% palladium-charcoal (40 mg) at 1 atm $H_2$. The catalyst was then separated by filtration, the solvent reduced in volume on a rotary evaporator, and the product precipitated by trituration with hexanes. The pale blue precipitate was collected by filtration, dried in vacuo (to yield 0.16 g (90%) of 18).

The diacid, b 14, was used directly, without delay, in the next step, the synthesis of 17a. This reaction is an acid-catalyzed [4]+[2] MacDonald-type[21] oxidative condensation with the readily available[4a] diformyl bipyrrole, 15. This condensation and the accompanying air oxidation, which taken together represent the second critical step in the overall synthetic sequence, then provide, following work-up and chromatographic purification, the diprotonated rubyrin derivative, X17a in roughly 20% yield. Washing either this purified ditosylate salt or the crude reaction mixture with aqueous 10% hydrochloric acid then produced the more crystalline dihydrochloride derivative, 17b in yields of 63% (based on 17a) and 40% (based on 14), respectively.

In more detail, to create 17a, 17b, and 19, compounds 15 (136 mg, 0.5 mmol) and 14 (273 mg, 0.5 mmol) were dissolved with warming in 1.0 L of absolute ethanol, the mixture allowed to cool to room temperature and 2.0 g of p-toluenesulfonic acid monohydrate added all at once. Oxygen was then bubbled through the stirred mixture for 18 hours. The ethanol was then removed on a rotary evaporator and the dark purple residue taken up in CHCl$_3$ and purified by column chromatography (Merck type 60 (230–400 mesh) Silica gel) using first CHCl$_3$ and then CHCl$_3$/MeOH(98/2) as the eluents. Collection of the dark red fraction and removal of the solvent gave 105 mg (20%) of 17a which could be purified further by recrystallizing from CHCl$_3$/hexanes. Collection of the violet fraction also yielded small ($\geqq$10% yield) amounts of 19.

Dissolving compound 17a in dichloromethane and washing with 10% HCl for 2 hours at room temperature then afforded, after work up, product 17b in ca. 63% yield. This same material could also be obtained in roughly 40% net yield by treating the crude condensation product (from 14 and 15) with 10% HCl prior to work up and chromatography. Single crystals of 17b were obtained by vapor diffusion recrystallization from CHCl$_3$/pentane.

For 17a: decomp. above 220° C.; $^1$H NMR (300 MHz, CDCl$_3$): $\delta = -4.14$ (s, 2 H, NH), $-3.68$ (s, 4 H, NH), 1.50 (s, 6 H, PhCH$_3$), 1.90 (d, $J_{HH}=7$ Hz, 4 H, phenyl H), 2.30 (m, 18 H, CH$_2$CH$_3$), 3.90 (s, 12 H, CH$_3$), 4.10 (m, 8 H, CH$_2$CH$_3$), 4.30 (s, 6 H, CH$_3$), 4.70 (q, 4 H, CH$_2$CH$_3$), 4.90 (d, $J_{HH}=7$ Hz, 4 H, phenyl H), 11.18 (m, 4 H, meso-H); HRMS (FAB): m/z 694.4707 (M$^+$ $-$2TsO$^-$), calcd for C$_{46}$H$_{58}$N$_6$ 694.4723 ($\pm$0.0016).

For 17b: decomp. above 230° C.; $^1$H NMR (300 MHz, CDCl$_3$); $\delta = -5.30$ (s, 2 H, NH), $-4.97$ (s, 4 H, NH), 2.09 (m, 12 H, CH$_2$CH$_3$), 2.34 (t, $J_{HH}=7$ Hz, 6 H, CH$_2$CH$_3$), 4,06 (s, 12 H, CH$_3$), 4.40 (s, 6 H, CH$_3$), 4.43 (m, 8 H, CH$_2$CH$_3$), 4.82 (q, $J_{HH}=7$ Hz, 4 H, CH$_2$CH$_3$), 11.58 (s, 2 H, meso-H) 11.60 (s, 2 H, meso-H); $^{13}$C NMR (75.5 MHz, CDCl$_3$): $\delta = 12.98$, 15.73, 17.50, 17.99, 21.05, 21.29, 92.74, 92.88, 126.47, 127.30, 129.03, 129.65, 130.73, 136.38, 139.32, 143.31; UV/VIS (CH$_2$Cl$_2$): $\lambda_{max}$ [nm]($\epsilon$)=505 (302,000), 711 (11,000), 791 (15,500), 850 (38,000); HRMS (FAB): m/z 694.4660 (M$^+$ $-$Cl$_2$), calcd for C$_{46}$H$_{58}$N$_6$ 694.4723 ($+$0.0063).

For 23: $^1$H NMR (300M Hz, CDCl$_3$): $\delta=0.98$ (m, 9 H, CH$_2$CH$_3$), 1.09 (m, 9 H, CH$_2$CH$_3$), 2.06 (m, 18 H, CH$_3$), 2.37 (m, 6 H, CH$_2$CH$_3$), 2.57 (m, 6 H, CH$_2$CH$_3$), 6.78 (m, 4 H, "meso"-H), 11.85 (s, 1 H, NH), 12.32 (s, 1 H, NH), 12.51 (s, 1 H, NH), 12.60 (s, 1 H, NH), 12.62 (s, 1 H, NH), 12.74 (s, 1 H, NH); MS (FAB): m/z 696 (M$^+$ $+$1, 4%), 695 (M$^+$, 5%), 307 (22%), 154 (100%); UV/VIS (CH$_2$Cl$_2$): $\lambda_{max}=538$ nm.

EXAMPLE II

SYNTHESIS OF RUBYRIN STRUCTURES 18a and 18b

Employing the same rubyrin synthetic methodology as described in Example I, but substituting the starting compounds for different starting materials allows a wide range of other rubyrin analogues to be prepared. For example, starting with diformyl bipyrrole 16$^{22}$ and performing the synthesis in the same manner as described above, gave in analogy salts 18a and 18b in similar good yield. From condensation of 14 (1.1 g, 2 mmol) and 16 (0.545 g, 2 mmol), 220 mg of compound 18a was obtained (16%). $^1$H NMR (300MHz,CDCl$_3$): $\delta=-5.66$ (s, 4H, NH), $-5.40$ (s, 2H, NH), 1.75 (t, $J_{HH}=7$, 6H, CH$_2$CH$_2$CH$_3$), 2.13 (t, $J_{HH}=7$, 6H, CH$_2$CH$_3$), 2.36 (t, $J_{HH}=7$, 6H, CH$_2$CH$_3$), 3.06 (m, 4H, CH$_2$CH$_2$CH$_3$), 4.24 (s, 6H, CH$_3$), 4.51 (s, 6H, CH$_3$), 4.77 (q, $J_{HH}=7$, 4H, CH$_2$CH$_3$), 5.06 (q, $J_{HH}=7$, 4H, CH$_2$CH$_3$), 11.17 (s, 2H, "meso"-H) 12.00 (s, 2H, "meso"-H), 12.29 (s, 2H, b-H); MS (FAB): m/z 694 (M$^+$ $-$2TsO$^-$); UV/VIS (CH$_2$Cl$_2$) $\delta_{max}=501$ nm.

EXAMPLE III

CHARACTERIZATION OF RUBYRIN STRUCTURES 17 and 18

Formally, rubyrin 10 and its derivatives may be considered as 26 $\pi$-electron annulenes. Thus, the diprotonated salts 17 and 18 were expected to be aromatic. The available spectroscopic data is consistent with this aromatic formulation. For instance, low-field meso-like methine signals and high-field internal NH resonances were observed in the $^1$H NMR spectra as would be expected for a large aromatic expanded porphyrin system. In the specific case of 17b in CDCl$_3$ these signals were observed at 11.58 and 11.60 ppm (in a 1:1 ratio), and at $-4.97$ and $-5.30$ ppm (in a 2:1 ratio), respectively, values which compare closely to those observed for the dihydrochloride salt of 3,8,12,13,17,22-hexaethyl-2,7,18,23-tetramethylsapphyrin [H$_2$.Sap]$^{2+}$ measured under the same experimental conditions$^{4a}$.

Figure 7:
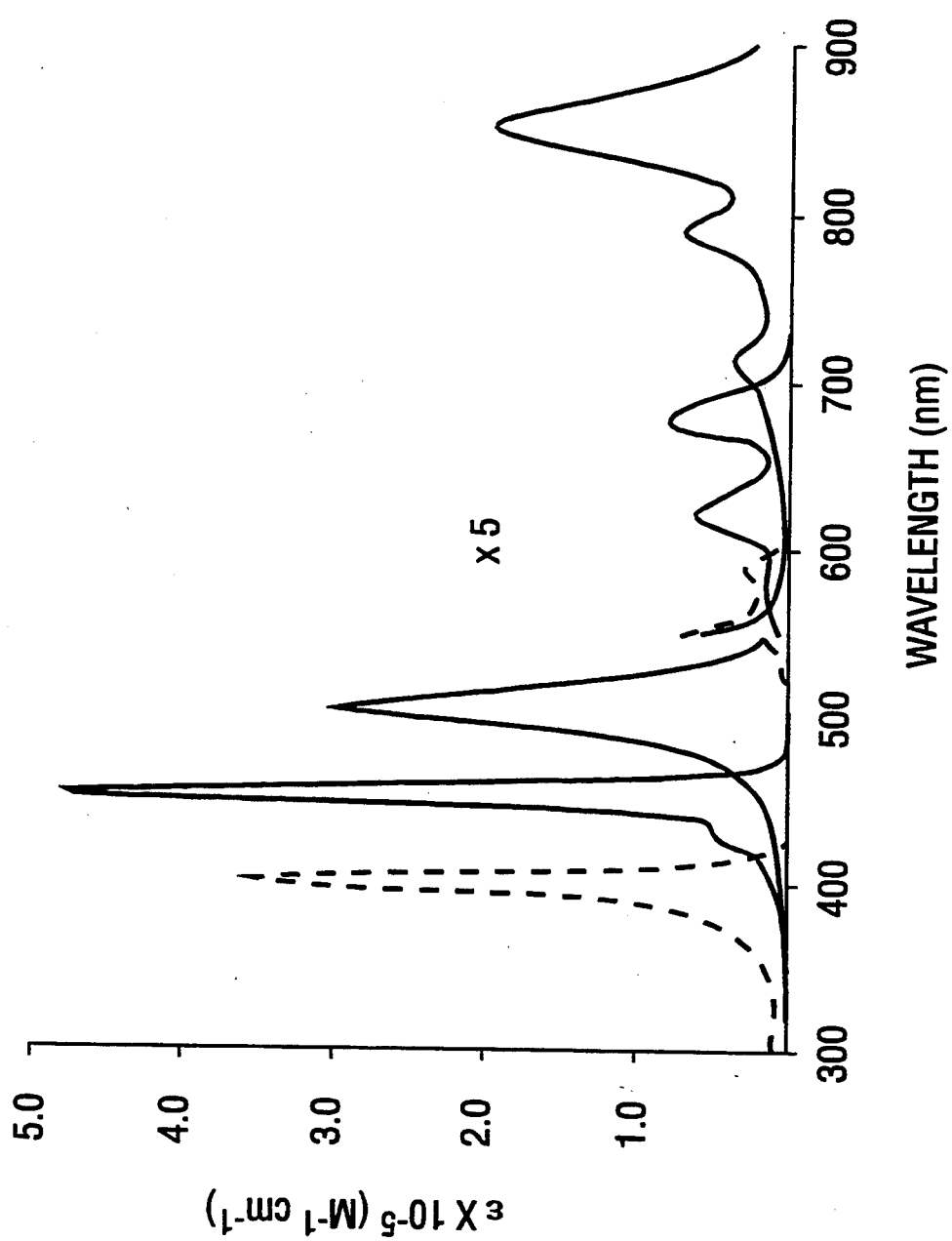
FIG. 7. The UV/VIS absorption spectra of 17b (—) and the diprotonated derivatives of 2,3,7,8,12,13,17,18-octaethylporphyrin (recorded in the presence of excess TFA) (···) and 3,8,12,13,17,22-hexaethyl-2,7,18,23-tetramethylsapphyrin (recorded as the dihydrochloride salt) (—) in dilute $CH_2Cl_2$.

Additionally, both 17 and 18 display Soret-like and Q-type transitions in their optical spectra, which, as would be expected for a large aromatic expanded porphyrin, are considerably red-shifted as compared to those of smaller porphyrin-like systems. In fact, relative to [H$_2$.Sap]$^{2+}$ and [H$_2$.OEP]$^{2+}$ (the diprotonated derivative of 2,3,7,8,12,13,17,18-octaethylporphyrin) measured under similar experimental conditions, the Soret band of 17b is shifted by ca. 50 and 100 nm, respectively (c.f. FIG. 7). In the case of the lowest energy Q-type band, the corresponding shifts are on the order of 180 and 270 nm, respectively.

Further evidence for the aromatic nature of rubyrin was obtained from the X-ray diffraction structure of 17b. The experimental details are as follows: (C$_{46}$H$_{56}$N$_6$H$_2$)$^{2+}$(Cl$^-$)$_2$(CHCl$_3$)$_2$; triclinic, P$\bar{1}$ (No. 2), Z=1 in a cell of dimensions: a=10.196(8), b=11,141(8), c=13.476(9) Å, $\alpha$=67.18(5), $\beta$=72.97(6) $\gamma$68.56(6)°, V=1293(2) Å$^3$, $\rho_{calc}$=1.29 g cm$^{-3}$ (173K), F(000)=526. Data collected at 173K on a Nicolet R3 diffractometer, graphite monochromatized Mo K$\alpha$ radiation (X=0.7107 Å) using the $\Omega$-scan technique out to 50° in 2$\Theta$; 4573 unique reflections, 2871 with F$_o^2>3\sigma$-(F$_o^2$) The structure was solved by direct methods and refined by full-matrix least-squares (SHELXTL-Plus, Nicolet XRD, Madison, Wis., USA) with anisotropic thermal parameters for the non-hydrogen atoms. Hydrogen atoms on C18, C19, C19A, C20, C21, C22, C22A and C23 were idealized (C—H 0.96 Å) while all others were taken from a AF map. All were refined isotropically. The complex lies around an inversion center at 0,1/2,1/2 resulting in the occupational disorder of the ethyl and methyl groups of the pyrrole ring containing N2. The Cl$^-$ions are H-bonded to the pyrrolic hydrogens and to the CHCl$_3$ solvate molecules. The final R=0.0529, R$_w$=0.0678, goodness of fit =2,284 for 361 parameters. The minimum and maximum peaks in the final $\Delta$F map were $-0.30$, 0.38 e$-$Å$^{-3}$, respectively.

Figure 8A:
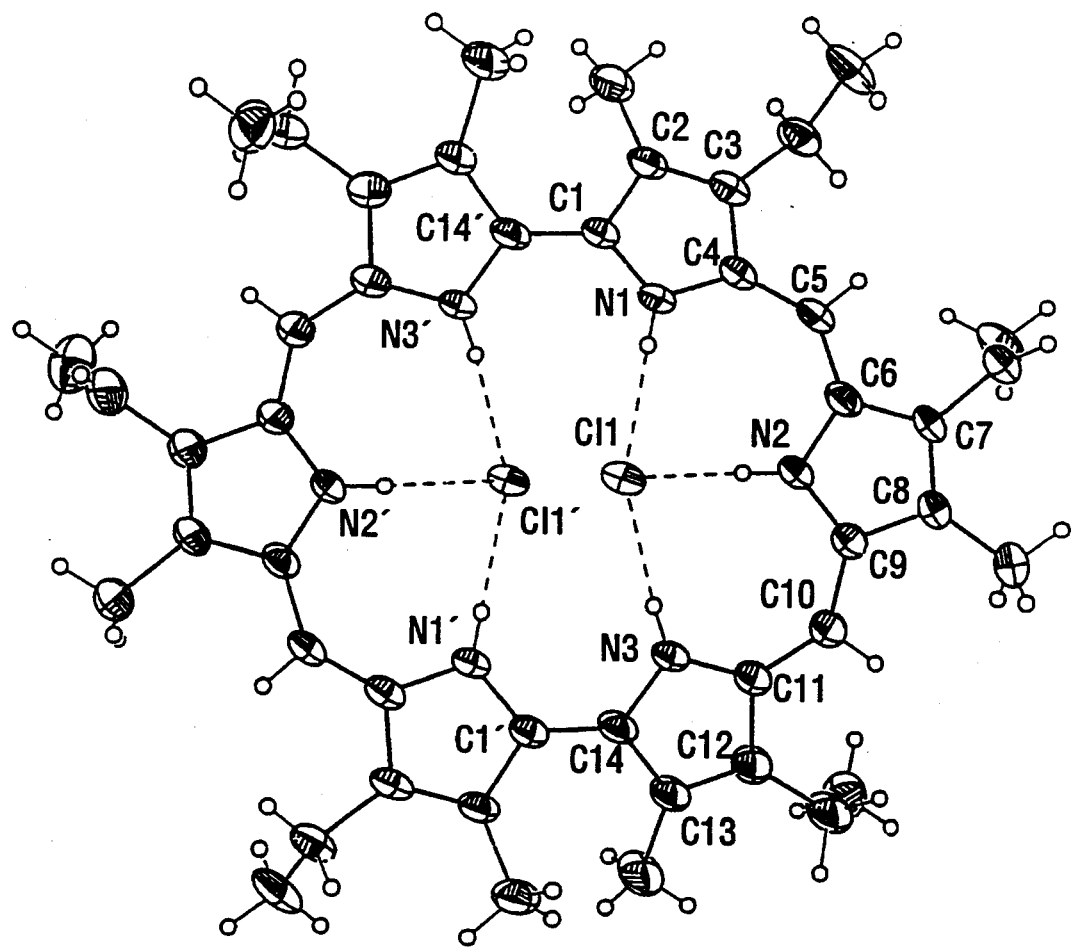
FIG. 8A and FIG. 8B . Molecular structure of 17b showing partial atom labeling scheme and the H-bonding interactions of the Cl$^-$ counterions with the macrocycle (dashed lines). Top: View perpendicular to the plane through the nitrogen atoms. Below: Side view showing the nearly planar conformation of the core macrocycle. The macrocycle lies around an inversion center. Atoms labeled with a ' are related by —x, 1 —y, 1 —z. Thermal ellipsoids are scaled to the 30% probability level. H atoms represented as spheres of arbitrary size. The disordered atoms and the chloroform molecules are not shown. Selected bond distances (Å) and angles (°): N1···C1, 1.373(5); N1···C4, 1.394(6); C1···C2, 1437(7); C2···C3, 1.362(5); C3···C4, 1.429(6 ); C4···C5, 1.381(5); C5···C6, 1.379(6); C6···C7, 1.421(5); C7···C8, 1.377(9); C8···C9, 1.449(8); N2···C6, 1.383(7); N2···C9, 1.367(5 ); N1···N2, 3.483(5); N1···N3, 5.559(5); N1···N1', 6.352(7); N1···N2', 5.836(5); N1···N3', 3.078(5); N2···N2', 7.213(7); N3···N3', 6.354(7); N1···Cl1, 3.265(4); N2···Cl1, 3.158(4); N1···C4···C 5, 130.1(4); C3···C4···C5, 123.4(4); C4···C5···C6, 137.6(5); C5···C6···C7, 122.9(5); C5···C6···N2, 129.5(4).
Figure 8B:
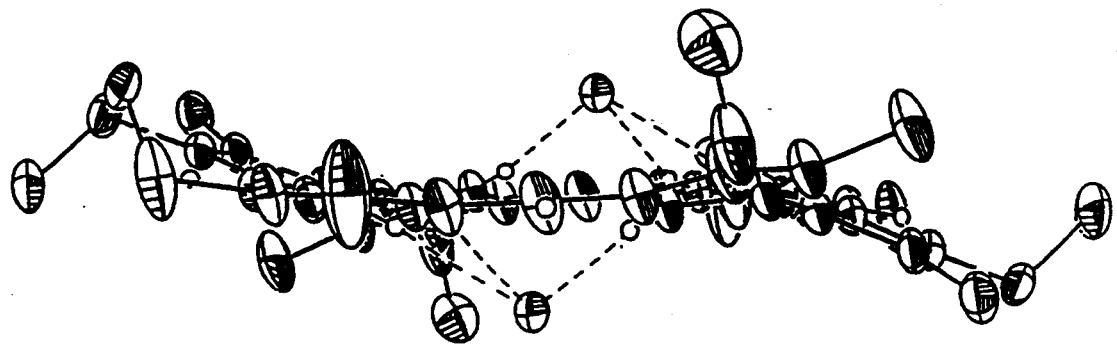

As illustrated in FIG. 8A and 8B, X-ray diffraction studies revealed structure 17 to have a near planar conformation for the core macrocycle that is only slightly waffled by virtue of interactions with the hydrogen-bound chloride counter anions (the maximum deviation (C2) of the C and N macrocycle atoms from the mean plane is 0.509(4) Å). In fact, this lack of distortion is reminiscent of that seen in the X-ray structure of $[H_2.O-EP]^{2+}$ (Ref. 23) and several recently-reported diprotonated bisvinylogous expanded porphyrins[13b,13c], suggesting that significant through-cycle $\pi$-electron conjugation pertains in 17b. Consistent with this conclusion is the finding that the average carbon-carbon and carbon-nitrogen bond distances within the formal 26 $\pi$-electron periphery (1.394 Å and 1.375 Å, respectively) are close in value to those observed in the corresponding diprotonated OEP structure (1.390 Å and 1.375 Å, respectively)[23a].

Interestingly, however, the inter-pyrrole angles about the bridging methines (137.0 and 137.6°) are considerably greater than those found in protonated porphyrins (wherein the in-core angles are roughly 127°)[23]. Thus, the expanded porphyrin 17b displays an inner core that is more open than might perhaps be expected for what may formally be considered as two directly appended "three-quarter porphyrins" linked via two sets of bipyrrole-defining bonds. Nonetheless, it is clear that from a structural point of view, compound 17b displays all that is expected of an aromatic system.

EXAMPLE IV

SYNTHESIS OF RUBYRIN STRUCTURES 10a and 10b

The synthesis of structure 10a, 4,8,13,18,23,27-hexaethyl-3,9,14,17,22,28-hexamethyl-29,30,31,32,33,34-hexaazaheptacyclo[24.2.1.1$^{2,5}$.1$^{7,10}$.1$^{12,15}$.1$^{16,19}$.1$^{21,24}$]tetratriaconta-1,3,5,7(31),8,10,12,14,16,18,20,22,24(34),25,27-pentadecaene (herein termed 4,8,13,18,23,27-hexaethyl-3,9,14,17,22,28-hexamethylrubyrin) was achieved as described below.

To synthesize compounds with structures 10a and 10b, the synthesis of compounds 17 and 18 was first conducted, as described above in Example III. In both cases, careful neutralization of dichloromethane solutions, achieved by washing with aqueous sodium bicarbonate, was found to give rise to the neutral, free-base forms, corresponding to structures 10a and 10b (FIG. 3) in the case of salts 17 and 18, respectively.

Specifically, this neutralization is carried out by dissolving salt 17 or 18 in $CH_2Cl_2$ in a one-neck round bottomed flask and adding saturated aqueous $NaHCO_3$. The two-layer mixture is then stirred via a magnetic stirring apparatus for two hours. Separating the organic layer from the aqueous layer, and washing the organic layer with de-ionized water in the same fashion described above, drying the organic layer over anhydrous sodium sulfate and removing the solvent on a rotary evaporator affords the neutral, free-base rubyrin analogue 10a or 10b.

Interestingly, the free-base form of 10b was generally found to be more stable. However, in both cases, the free-base form proved rather unstable. Thus, as described herein, full characterization was effected using the diprotonated forms, 17 and 18.

EXAMPLE V

SYNTHESIS OF RUBYRIN ANALOGUE STRUCTURE 19

In addition to those described above, several other products were obtained in the course of the above condensations. In the case of primary product 17a, an effort was made to characterize these materials and two such minor products were thus identified. The first of these was found to be a sapphyrin derivative, namely 3,7,12,18,22-pentaethyl-2,8,13,17,23-pentamethylsapphyrin.

Figure 5:
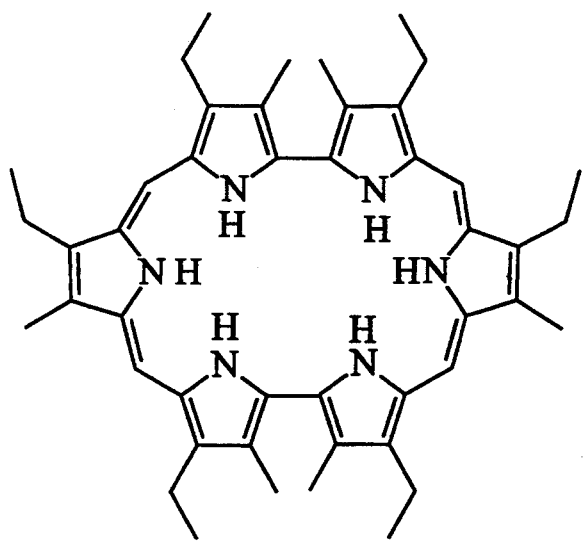
FIG. 5, the rubyrin-like system, 4,8,13,18,23,27-hexaethyl-3,9,14,17,22,28-hexamethyl-29,30,31,32, 33,34-hexaazaheptacyclo[24.2.1.1$^{2,5}$.1$^{7,10}$.1$^{12,15}$.1$^{16,19}$.1$^{21,24-}$]tetra triaconta-1,3,5,7,9,11,13,15,17,19,21,23,25,27-tetradecaene.

The second was a partially reduced, rubyrin-like system, 4,8,13,18,23,27-hexaethyl-3,9,14,17,22,28-hexamethyl-29,30,31,32, 33,34-hexaazaheptacyclo[24.2.1.1$^{2,5}$.1$^{7,10}$.1$^{12,15}$.1$^{16,19}$.1$^{21,24}$]tetra triaconta-1,3,5,7,9,11,13,15,17,19,21,23,25,27-tetradecaene (structure 19, FIG. 5). This compound (structure 19) was received as a byproduct of the reaction sequence to produce compound 17a. It has the same connectivity but is of different oxidation state. Nonetheless, this material appeared to be stable to the reaction conditions. Still, however, it could be converted to 17b in near quantitative yield by treating with DDQ in the presence of acetic acid and then washing with 10% HCl. Thus, at the present time, it is not clear whether compound 19 itself (as opposed to some other reduced rubyrin species) functions as the actual intermediate under the present condensation conditions.

Figure 2B:
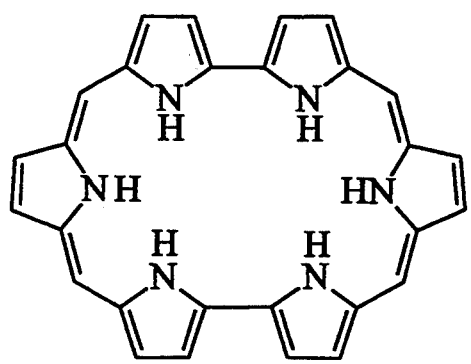

In any case, this well characterized product, compound 19, which is bright violet in color, stands as a specific embodiment of compounds of the general class represented by FIG. 2B. Its existence and isolation thus stands as evidence inter alia that compounds with the same connectivity and total non-hydrogen atom count as rubyrin, as exemplified by FIG. 2B, can be prepared according to the methods of the present invention.

EXAMPLE VI

SYNTHESIS OF RUBYRIN ANALOGUES REPRESENTED BY FIG. 2C

Figure 2C:
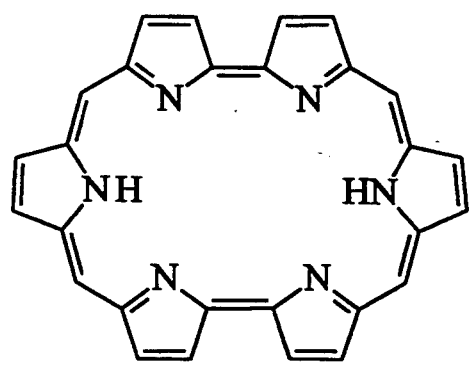
Figure 2D:
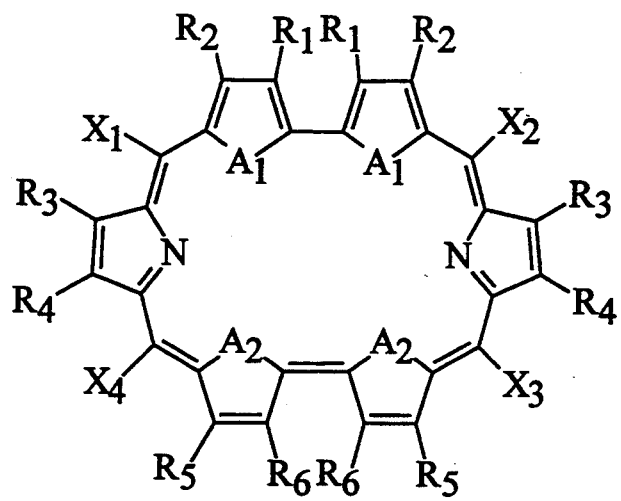
Figure 2E:
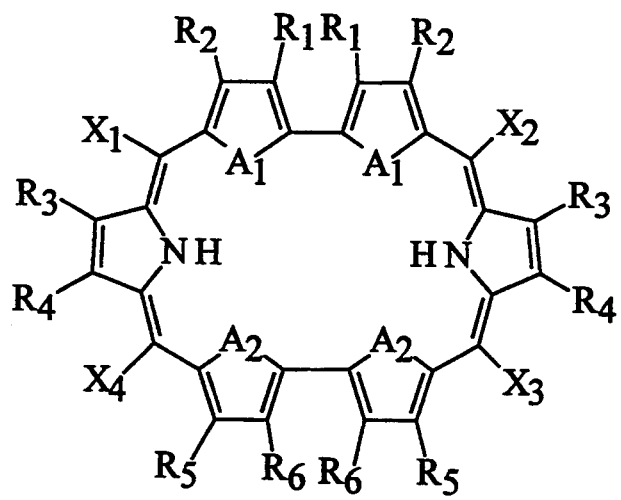
Figure 2F:
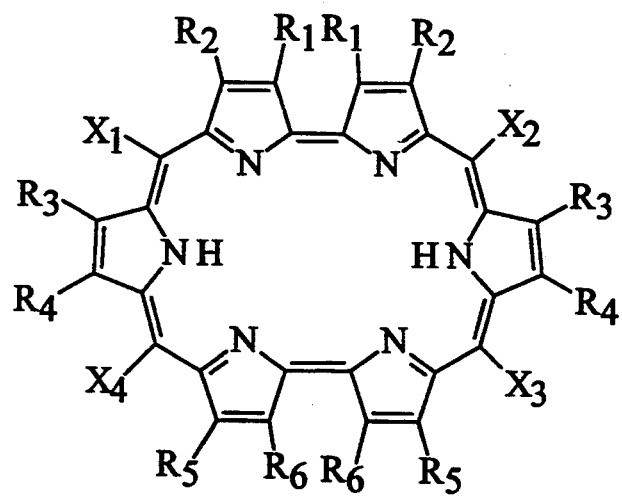

In addition to those compounds, such as 19, represented by FIG. 2B, compounds based upon FIG. 2C will also have the same connectivity and total non-hydrogen atom count as rubyrin. These compounds may also be prepared according to the synthetic methodology disclosed herein. For example, the hexamethyl hexaethyl derivative of FIG. 2C may be an as-yet uncharacterized byproduct of the reaction used to prepare 17. Alternatively, it is contemplated that this material may be obtained by controlled reduction of 17 using hydride reagents and/or controlled hydrogenation.

EXAMPLE VII

SYNTHESIS OF SUBSTITUTED RUBYRINS AND FURTHER ANALOGUES

It will also be apparent to one of skill in the art of organic chemistry that the two rubyrins presented in FIG. 4A and FIG. 4B (or their reduced congeners as represented by compounds such as 19) are not the only ones that can be obtained within the context of this synthetic methodology. For example, firstly, the inventors contemplate that the choice of bipyrroles for use in the second condensation step, as illustrated by the use of 15 and 16 (to make 17 and 18), may be varied. Secondly, it is also envisioned that different combinations of bipyrroles and pyrroles may be employed in the first condensation step to produce various analogues of 13 and 14.

A preliminary example concerns the inventors' use of 5,5'-diformyl-4,4'-dipropyl-2,2'-bipyrrole as a starting material for use in reaction sequences in accordance with the present invention. This synthetic process involved reaction with compound 12 followed by debenzylation and subsequent condensation with compound 16 to yield an analogue of compound be, 8,23-diethyl-4,13,18,27-tetrapropyl-9,22-dimethylrubyrin, in which four of the 12 possible β-pyrrolic positions are unsubstituted by alkyl groups. Satisfactory NMR and high resolution mass spectrometric data was obtained for this product.

Accordingly, it is contemplated that a variety of approaches may be employed, in accordance with the present invention, to prepare systems bearing a wide variety of alkyl and/or aryl substituents in the meso and/or β-pyrrolic positions.

For example, meso substituted compounds may be prepared to test the extent to which the presence of different groups, such as, for example, 4'-phenyl and/or 2'-phenyl donating groups can be made to augment effective nitrogen lone pair basicity and/or enhance higher pH phosphate transport capability. Extensions to systems bearing two (or more) meso substituents are also contemplated within the scope of the invention. In any event, it is important to appreciate that by adding further meso substituents one will, in all likelihood, induce substantial distortions of the macrocycle off planarity. Thus, these syntheses should provide compounds that will allow steric effects to be assessed. Naturally, it is contemplated that transport and $pK_a'$ tests will be conducted to determine the effects of the various substitutions.

In preliminary work, to date, several phenyl-bearing rubyrins have been prepared by a "direct insertion" procedure. This procedure (a specific example of which is shown in Reaction Scheme A), which is necessarily inefficient, involves the condensation of a bis-α-free bipyrrole (e.g., 25) with an α, ω-free bis(pyrrolyl)-bipyrrole (e.g., 26) in the presence of benzaldehyde or substituted benzaldehyde under rubyrin forming conditions, as described herein, to afford bisarylrubyrin This inefficiency reflects the fact that in addition to the bisarylrubyrin products, one also obtains a range of other macrocyclic and non-macrocyclic products.

Improved syntheses can be envisioned, however, in which an α-free, ω-protected bipyrrole (e.g., structure 28 in Reaction Scheme B), is co-condensed with an ε-free pyrrole (e.g., 29) in the presence of an aromatic aidehyde, as in Reaction Scheme B. The benzyl ester of the resulting pyrrolyl-bipyrrole can then be selectively cleaved under standard debenzylation conditions and decarboxylated with trifluoroacetic acid to give the α-free pyrrolyl-bipyrrole, structure 30. Acid catalyzed condensation of pyrrolyl-bipyrrole 31 with another molecule of α-free pyrrole 28 in the presence of an aromatic aldehyde yields an ethyl ester-protected diaryl, bis(pyrrolyl)-bipyrrole 32, which can be deprotected to form the α, ω-free bis(pyrrolyl)-bipyrrole 33. Acid catalyzed co-condensation of the tetrapyrrolic fragment 33 with an α, ω-free bipyrrole (e.g., 34) in the presence of an aromatic aidehyde, under rubyrin-forming conditions such as those described in Example 1, affords a rubyrin with each of its four "meso" positions substituted with aryl groups (e.g., 35, Reaction Scheme B).

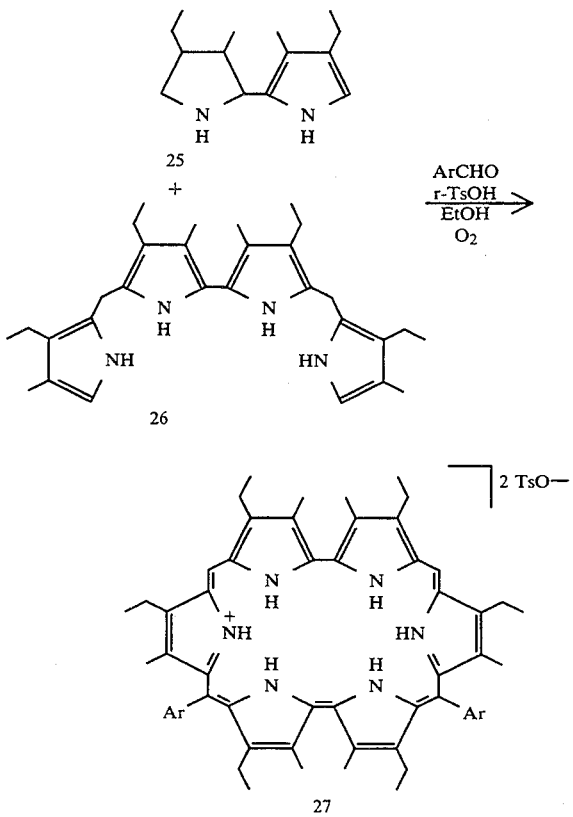

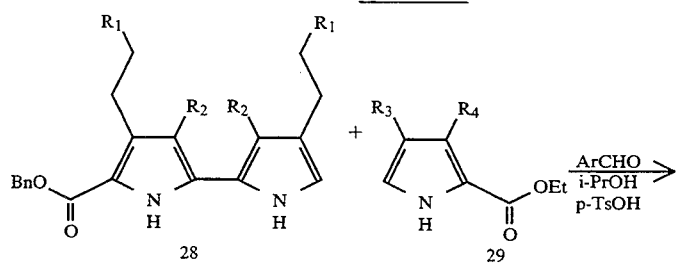

-continued
Scheme B
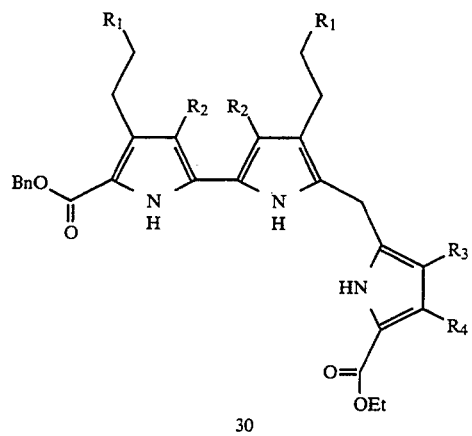
30
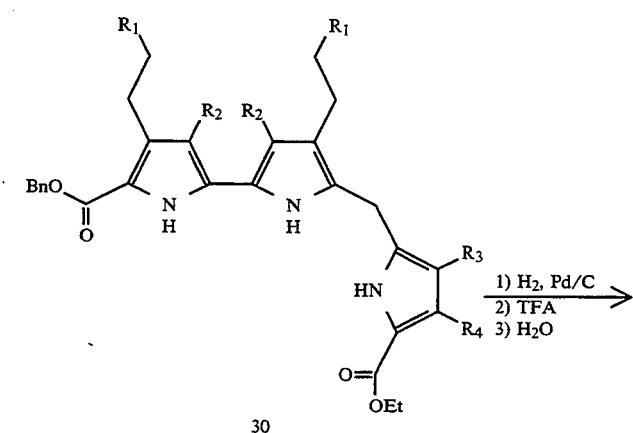
30
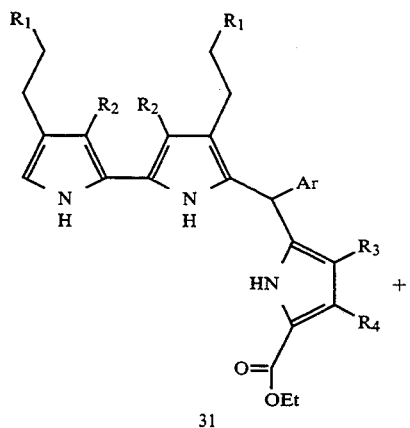
31
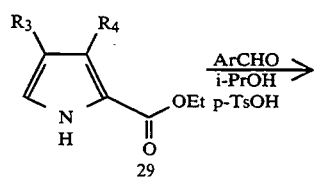
29

-continued
Scheme B
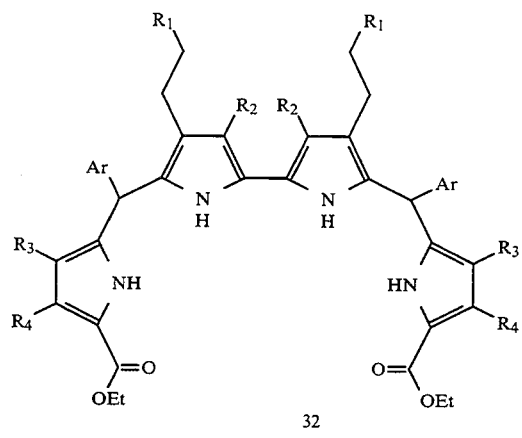
32
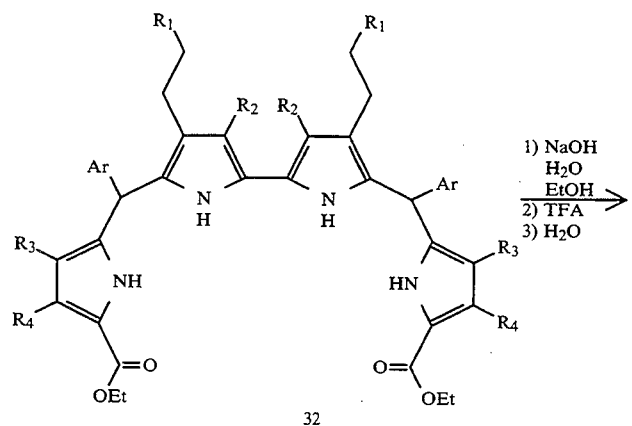
32
1) NaOH
   H₂O
   EtOH
2) TFA
3) H₂O
→
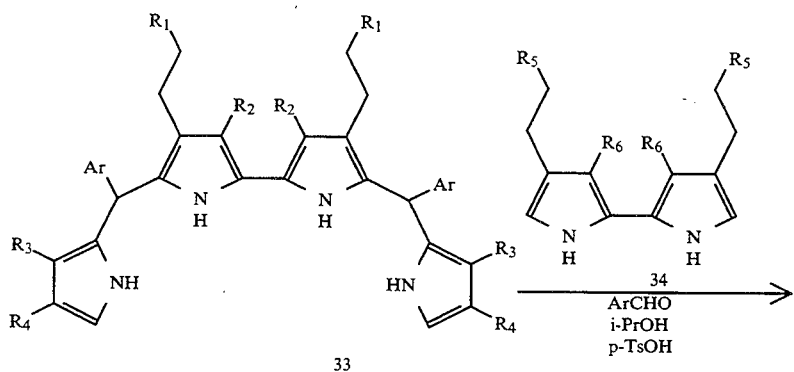
33
34
ArCHO
i-PrOH
p-TsOH
→

Scheme B

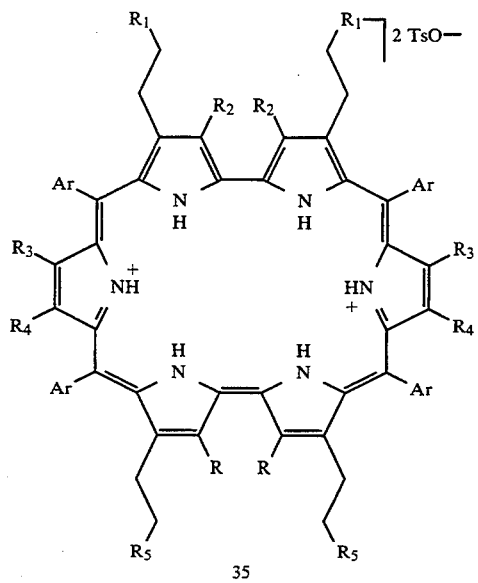

It will, of course, be understood that in syntheses such as those exemplified in Reaction Scheme B, substituents in the starting compounds, such as those groups represented by $R^1$, $R^2$, $R^3$ and $R^4$, may be varied as desired. Such groups may separately and independently include, for example, H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether, or substituted amide groups. Thus, by using the appropriately substituted starting units, a rubyrin product may be produced in which groups $R^1$–$R^6$ (as represented by structure 35) may be substituted with any of the groups listed above.

Extensions of known methods can also be straightforwardly conceived that would allow one of skill in the art, in light of the present disclosure, to prepare functionalized rubyrins bearing one or more non-alkyl substituents in the $\beta$ positions. As is true for the sapphyrins[4a,80] the easiest entry into such systems involves the preparation of carboxy alkyl substituted systems, for example, compounds bearing substituents such as —$(CH_2)_n$—$CO_2H$, and then further elaborating these to form the corresponding hydroxy alkyl, amino alkyl, thiol, sulfanato, ether, amide, ester, or formyl alkyl derivatives.

In addition to the direct conversions described above, it is important to appreciate that carboxy alkyl substituted rubyrins can also be used as the basis for obtaining other, more complex functionalized systems. For instance, as described by Král et al, 1992[77], incorporated herein by reference, for the sapphyrin series, the carboxylic acid group of the carboxy alkyl bearing rubyrins can be activated using standard reagents (such as, for example, thionyl chloride or DCC) and used to prepare either ester- or amide-linked conjugates.

Again, in analogy to the sapphyrins, said conjugates could include compounds that contain one or more nucleic acid base ("nucleobase") or sugar ("saccharide") subunits, as is described in detail in the following Examples (Examples VIII and IX). For example, in such syntheses, one may condense a protected amino alkyl nucleobase, for instance, the known material 1-(2-aminoethyl)-4-[triphenylmethyl)amino]-pyrimidin-2-one[78], with the activated rubyrin carboxylic acid and subsequently effect nucleobase deprotection. Similarly, one may employ an amino-bearing protected sugar, such as per-O-acetylated glucosamine, and subsequent deprotection. In addition, one can use such a conjugation approach to prepare complex ethers, esters, or amides where the ether, ester, or amide linkages are used to append a wide variety of polyfunctional substituted alcohol and/or amine fragments on to the rubyrin periphery.

The requisite carboxy alkyl substituted rubyrins can be prepared by several routes. Two of these bear direct analogy to the earlier work in the sapphyrin series and thus are chosen for highlight in this example. First, in analogy to the preparation of 3,12,13,22-tetraethyl-8,17-bis(carboxyethyl)-2,7,18,23-tetramethylsapphyrin[41], condensation of benzyl 5-acetoxymethyl-3-methyl-4-(methoxycarbonylethyl)-pyrrole-2-carboxylate, structure 37, with bipyrrole 36 can be used to obtain, following debenzylation, bis(5-carboxy-3-(methoxycarbonylethyl)-4-methyl-pyrrol-2-ylmethyl)-2,2'-bipyrrole 38b (Reaction Scheme C). This compound, following condensation with bipyrrole 39, under rubyrin-forming conditions such as those described in Example 1, will provide the rubyrin system 40 bearing two carboxy alkyl substituents (Reaction Scheme C). In the structures represented in scheme C, $R^1$, $R^2$, $R^4$, and $R^5$ in the starting units and the product, may separately and independently include H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether, or substituted amide groups.

Second, in retrosynthetic analogy to the more recent preparation of 3,8,17,22-tetraethyl-12-(carboxyethyl)-2,7,13,18,23-pentamethylsapphyrin[77], benzyl 3,5- dimethyl-4-(methoxycarbonylethyl)-pyrrole-2-carboxylate 41 may be converted, as shown in Reaction Scheme D, to its corresponding bipyrrole 44a (3,3'-bis(methoxycarbonylethyl)-5,5'-bis(benzyloxycarbonyl)-4,4'-dimethyl-2,2'-bipyrrole) via sulfuryl chloride oxidation to acid 42, followed by standard iodination (43), and copper bronze mediated Ullman coupling[4a, 82]. Following standard debenzylation to produce 44b and Clezy formylation with trifluoroacetic acid (TFA) and triethylorthoformate, condensation of the resulting bipyrrole 45 (3,3'-bis(methoxycarbonylethyl)-5,5'-diformyl-4,4'-dimethyl-2,2'-bipyrrole) with the tetrapyrrolic fragment 46 of Reaction Scheme E, under normal rubyrin-forming conditions such as those described in Example I, will provide a rubyrin containing at least two carboxy alkyl substituents, at positions 4 and 27, protected as their corresponding methyl esters (structure 47, Reaction Scheme E). As with other examples presented herein, $R^1$, $R^2$, and $R^3$ of structures 46 and 47, may separately and independently include H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether, or substituted amide groups.

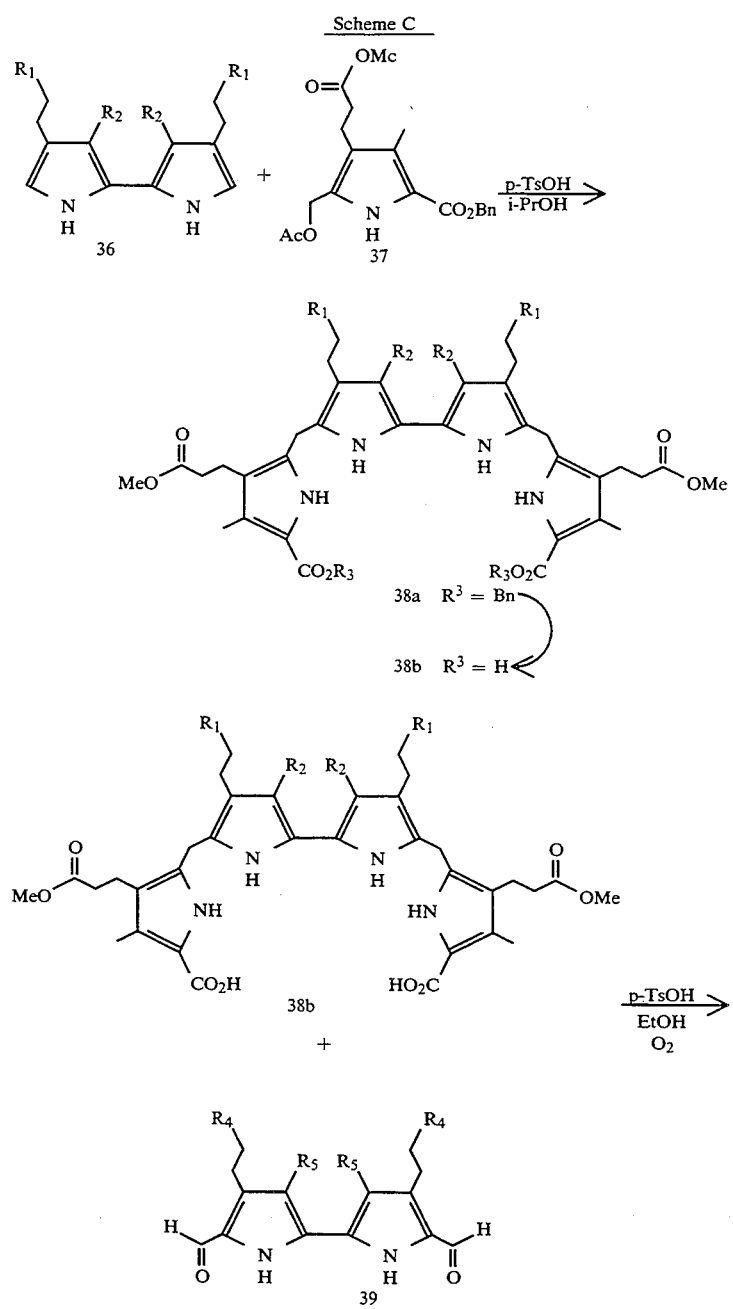

Scheme C
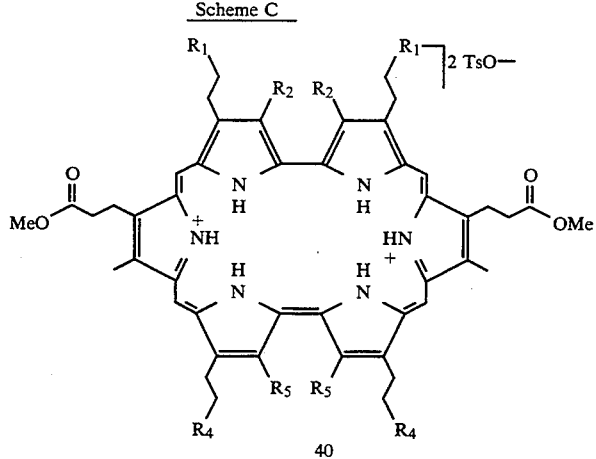
Scheme D
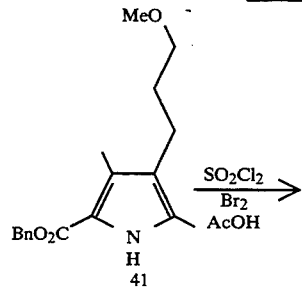
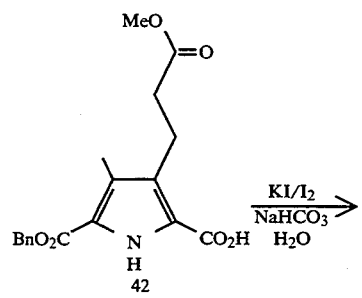
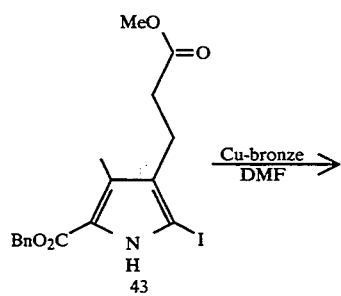
-continued
Scheme D
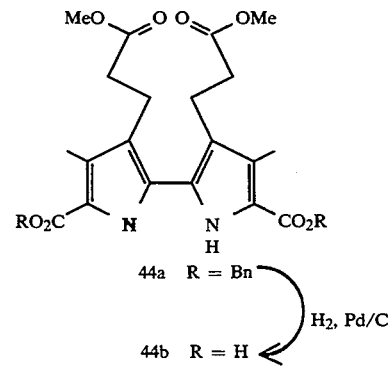
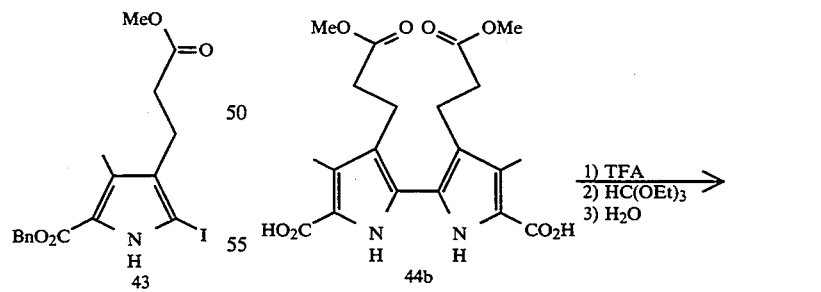
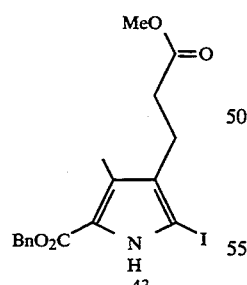
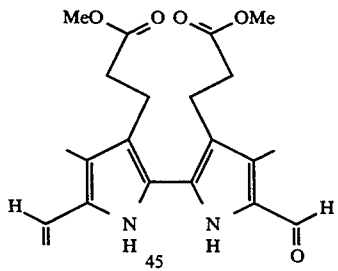

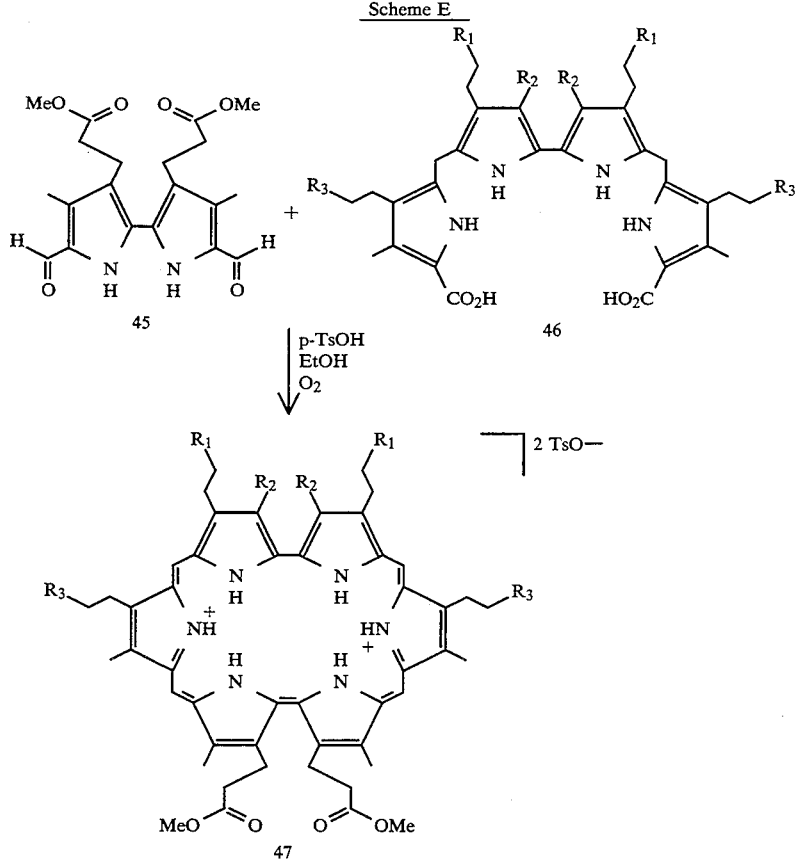

Scheme E

EXAMPLE VIII

SYNTHESIS OF RUBYRIN-NUCLEOBASE CONJUGATES

It is contemplated that suitable rubyrin-based dibasic phosphate chelators may be modified so as to obtain ditopic binding systems that display high inherent specificity for a given purine or pyrimidine derived nucleotide. This may be achieved by adding a synthetic appendage of a nucleobase moiety. For example, the known aminobutyl cytosine derivative may be employed with an acid-catalyzed detritylation procedure.

Alternatively, the mode of base attachment may be varied, for example, at the level of coupling, protecting group, precursors, and the length, nature, and orientation of any linking groups. The effects of such variations on yield, selective binding, and other properties of the resultant rubyrin-based molecule, such as, for example, effective through-membrane transport capability may then be determined and any adjustments made accordingly. For example, the nature of R groups may be changed, or 2° amides replaced by 3° ones.

In principle, based on preliminary studies which demonstrated the feasibility of achieving nucleobase "chelation" via complementary Watson-Crick type base-pairing interactions, these compounds should display base-selective transport capability. This may be specifically examined by various structural, static binding, and dynamic transport analyses. In particular, it will be determined whether the cytosine-forguanine selectivity that the inventors observed in mixed (i.e. non-covalently linked) systems[24] holds in the case of suitably designed synthetic conjugates. In addition, it will be tested whether this same base-pairing approach suffices to engender nucleobase selectivity in the case of adenine-thymine pairing.

As an extension of the above analyses, doubly functionalized systems may be synthesized for use in the selective binding of dinucleotides, some of which have interesting antiviral properties[72], as well as for the recognition and transport of mononucleotides. In the latter case, it is suggested, the possible combination of both Watson-Crick and Hoogsteen type base-pairing interactions could confer a degree of specificity not available using simpler systems. To the extent this proves true, it is possible that the doubly functionalized rubyrin system could serve as a viable antiviral adjuvant, capable not only of binding and solubilizing the phosphate portion of a nucleotide monophosphate, but also of effecting its selective through-membrane transport at or near physiologic pH.

The studies carried out in the sapphyrin series stands as an allegory of success. For instance, it was found that the attachment of a nucleobase to a sapphyrin core greatly enhanced the nucleotide recognition selectivity for transport. Thus the inventors expect that the functionalization of rubyrins, which because of their larger core size and increased basicity are inherently much better for anion recognition and phosphate anion chelation than sapphyrins, will lead to systems of tremendous superiority relative to any produced to date.

Reaction Schemes F through I represent examples of the synthesis of rubyrin nucleobase conjugates. The synthetic methodology represented in these reaction schemes may be straightforwardly adapted for the synthesis of any given rubyrin nucleobase compound by employing the desired starting materials. Groups $R^1$, $R^2$, $R^4$, and $R^5$ in Reaction Schemes F and G, and groups $R^1$, $R^2$ and $R^3$ in Reaction Schemes H and I, may separately and independently include H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether, or substituted amide groups.

The first example of the preparation of a rubyrin nucleobase conjugate is shown in Reaction Scheme F. Here, a dicarboxy alkyl bearing rubyrin, the 8,23-bis(-methoxycarbonylethyl)-rubyrin 48 can be saponified to its diacid form 49 by treatment with a 1:1 mixture of HCl and trifluoroacetic acid. DCC coupling of rubyrin diacid 49 with trityl protected aminoethyl cytosine S0 in methylene chloride at 0° C. followed by deprotection with TFA, as shown in Reaction Scheme F, affords the amide linked bis(aminoethyl)cytosine rubyrin conjugate Similarly, the amide linked bis(aminoethyl)guanosine rubyrin conjugate 55 can be prepared by DDC coupling of rubyrin diacid 53 with benzoyl-protected aminoethyl guanosie 54 in DMF at 0° C. followed by deprotection with TFA as shown in Reaction Scheme G.

In another example of a dicarboxy alkyl bearing rubyrin, the 4,27-bis(methoxycarbonylethyl)-rubyrin 56 (Reaction Scheme H) can be saponified to diacid 57 by treatment with a 1:1 mixture of HCl and trifluoroacetic acid. DCC coupling of rubyrin diacid 57 with tritylprotected aminoethyl cytosine 58 in methylene chloride at 0° C. followed by deprotection with TFA, as shown in Reaction Scheme H, affords the amide linked bis-(aminoethyl)cytosine rubyrin conjugate 59.

The amide linked bis ( aminoethyl ) guanosine rubyrin conjugate 63 of Reaction Scheme I can be prepared by DDC coupling of rubyrin diacid 61 with benzoyl-protected aminoethyl guanosine 62 in DMF at 0° C. followed by deprotection with TFA as shown in Reaction Scheme I.

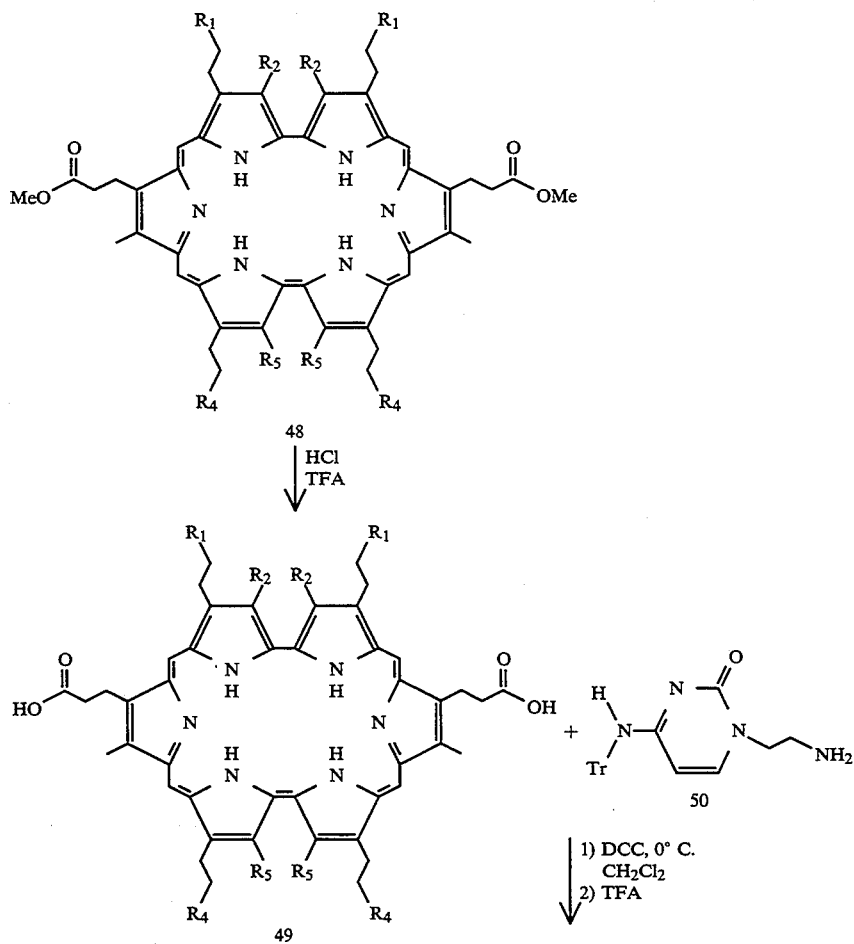

Scheme F 5,410,045
Scheme F
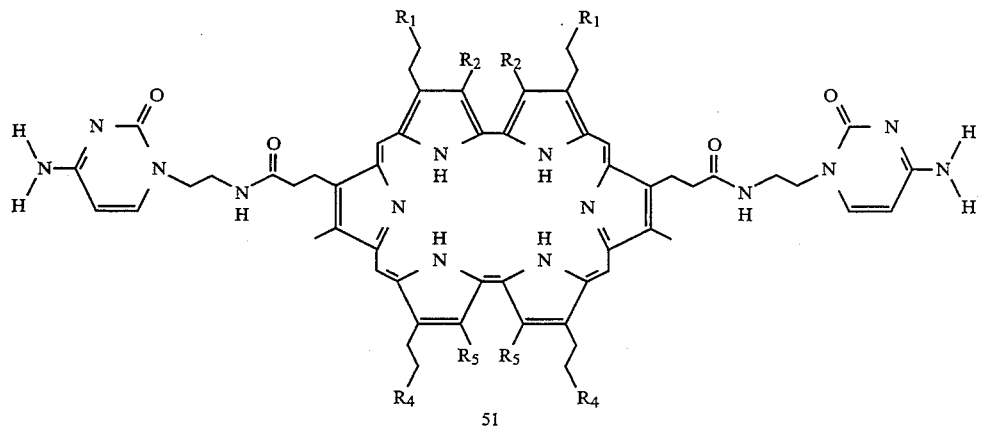
51
Scheme G
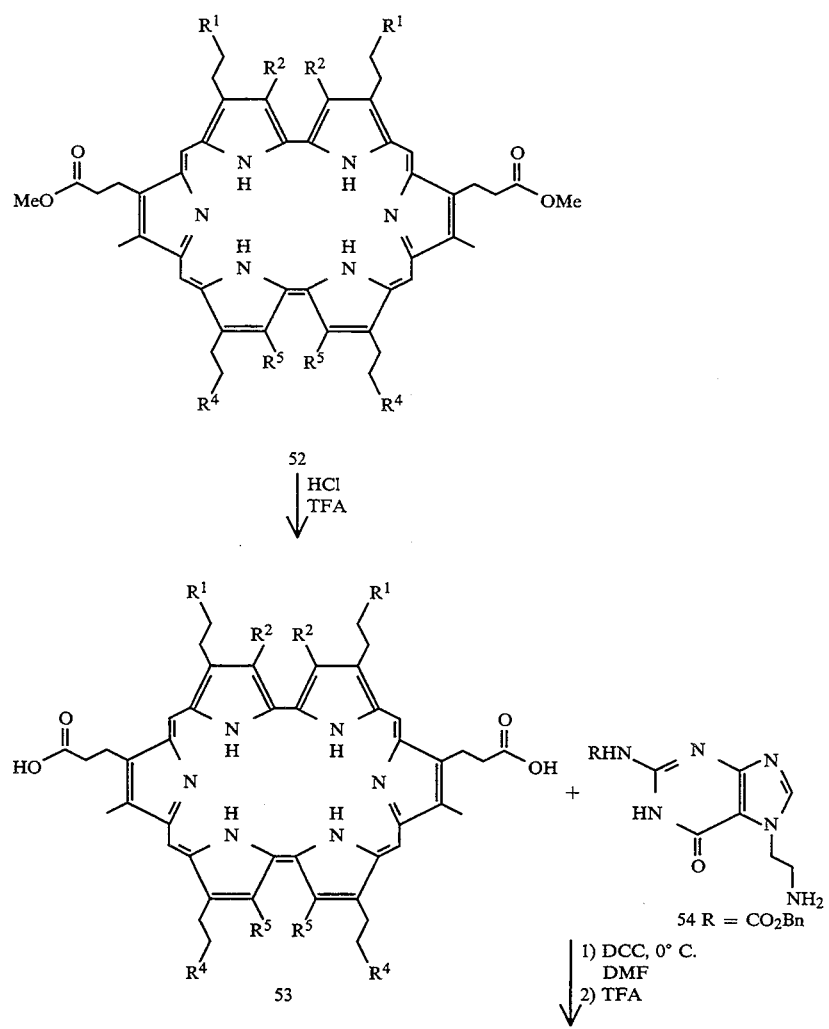

Scheme G
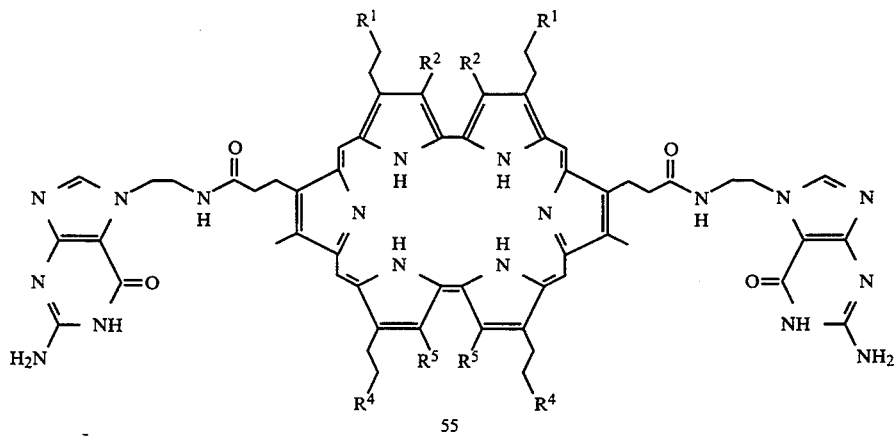
Scheme H
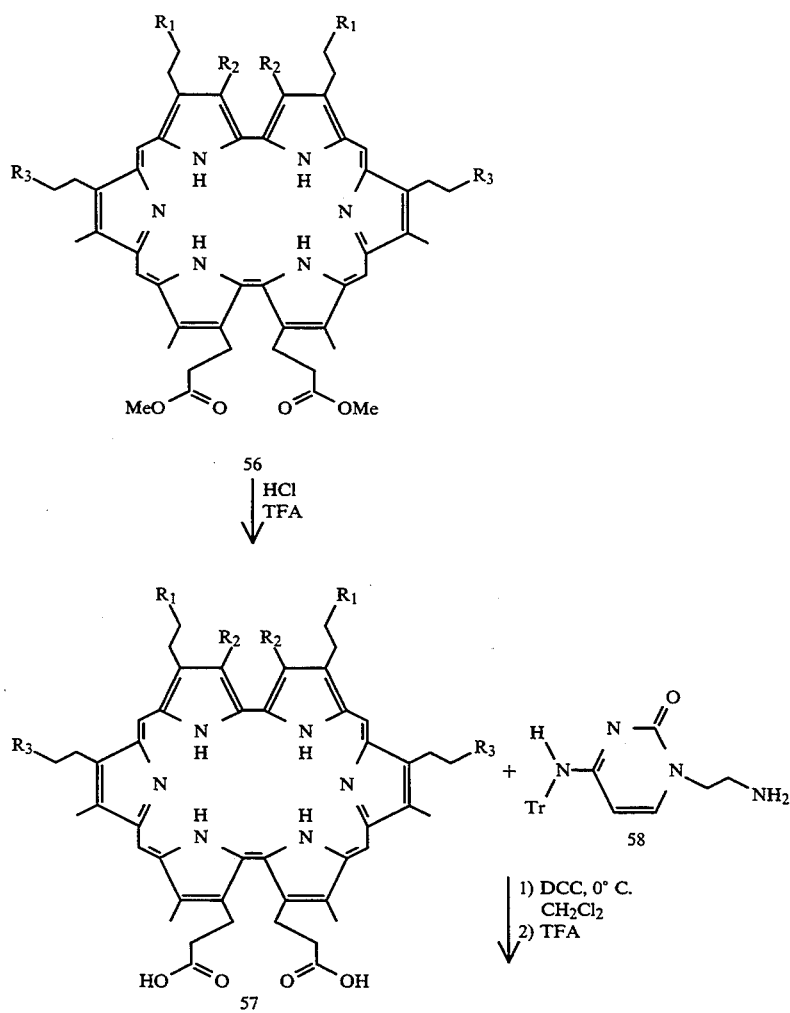

-continued
Scheme H
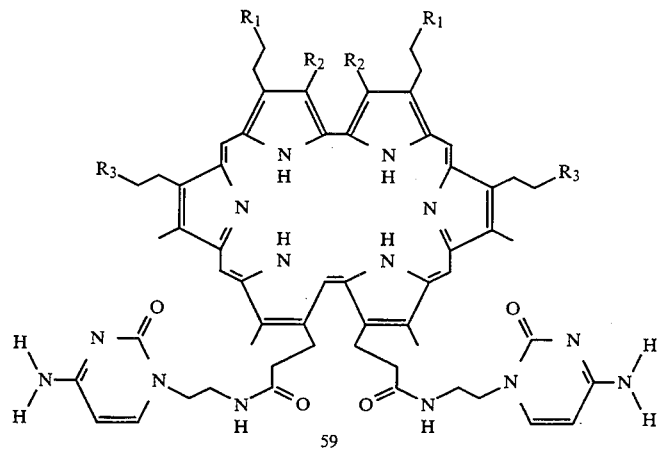
Scheme I
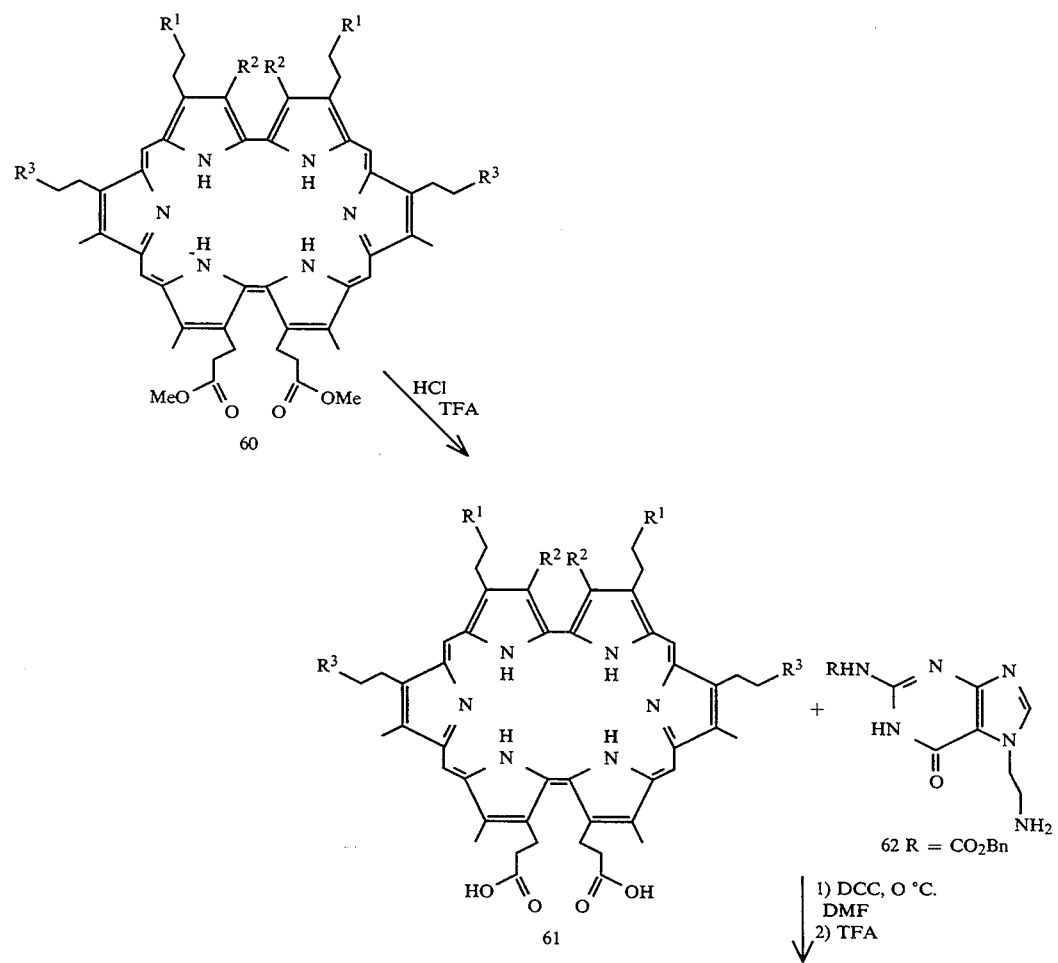

-continued

Scheme I

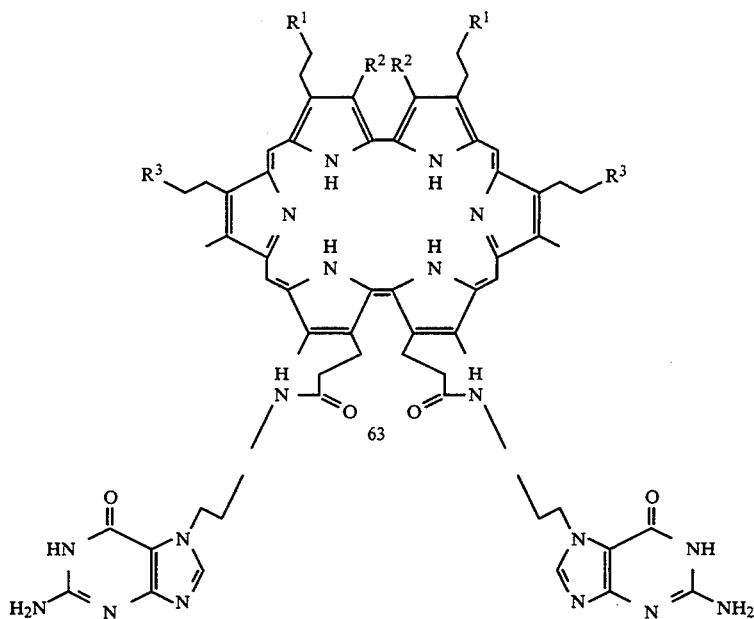

EXAMPLE IX

SYNTHESIS OF RUBYRIN-SACCHARIDE CONJUGATES

Rubyrin derivatives or conjugates including one or more saccharide units may also be prepared according to the synthetic methodology described hereinbelow. The sugar units (represented originally by structures 65 and 75) in Reaction Schemes J through O are intended to represent any individual sugar or sugar derivative, such as those set forth in Table 2, or polymers thereof, and include modified sugars, such as methyl, amino, and phosphate sugars, and D-, L-, α and β forms of said sugars.

The synthetic methodology represented in the following reaction schemes may be straightforwardly adapted for the synthesis of any rubyrin saccharide compound as desired. Groups $R^1$, $R^2$, $R^4$, and $R^5$ in Reaction Schemes J, L and M, and groups $R^1$, $R^2$ and $R^3$ in Reaction Schemes K, N and O, may separately and independently include H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether, or substituted amide groups.

For the preparation of amide-linked rubyrin saccharide conjugates, such as those represented by structure 66, diacid chloride substituted rubyrin 64 (Reaction Scheme J) may be prepared by treating its respective diacid rubyrin, formed as shown in Reaction Scheme J, with thionyl chloride. The rubyrin diacid chloride 64 thus prepared can be coupled with the acetoxy protected HBr salt of amino saccharide 65 in methylene chloride and pyridine, and deprotected with KOH in methanol as in Reaction Scheme J.

In the same fashion, the 4,17-bis(acid chloride)rubyrin 67 (Reaction Scheme K) can be prepared by treating its respective diacid rubyrin, formed as shown in Reaction Scheme H, with thionyl chloride. The amide-linked bis(saccharide) rubyrin 68b may be prepared by coupling rubyrin diacid chloride 67 with the acetoxy protected HBr salt of amino saccharide 65 in methylene chloride and pyridine, followed by deprotection with KOH in methanol as illustrated in Reaction Scheme K.

To prepare ether-linked bis(saccharide)rubyrin conjugates, the dihydroxy functionalized rubyrins, such as those represented by structure 73b in Reaction Scheme L, may be prepared. For example, reduction of the methyl esters of tetracycle 69 with borane-THF to the corresponding alcohols followed by protection with acetic anhydride provides the acetoxy-protected diol 71a. Standard debenzylation to afford 71b followed by condensation with diformyl bipyrrole 72, under rubyrin-forming conditions such as those described in Example I, provides the acetoxy-protected dihydroxy rubyrin 73a. Deprotection of the hydroxyl groups can be achieved by treatment with HCl in methanol to afford dihydroxyrubyrin 73b.

Dihydroxyrubyrins, formed as described above (Reaction Scheme L), can be coupled with acetoxy- and/or benzoyl-protected bromo-substituted saccharide units, such as structure 75 (Reaction Scheme M), in methylene chloride with silver triflate and barium carbonate. This results in the production of acetoxy and/or benzoyl-protected bis(saccharide)rubyrin conjugates such as 76a in Reaction Scheme M. Treatment of the acetoxy and-/or benzoyl protected bis(saccharide)rubyrin 76a with KOH in methanol yields the corresponding deprotected bis(saccharide)rubyrin conjugate 76b (Reaction Scheme M).

Scheme J
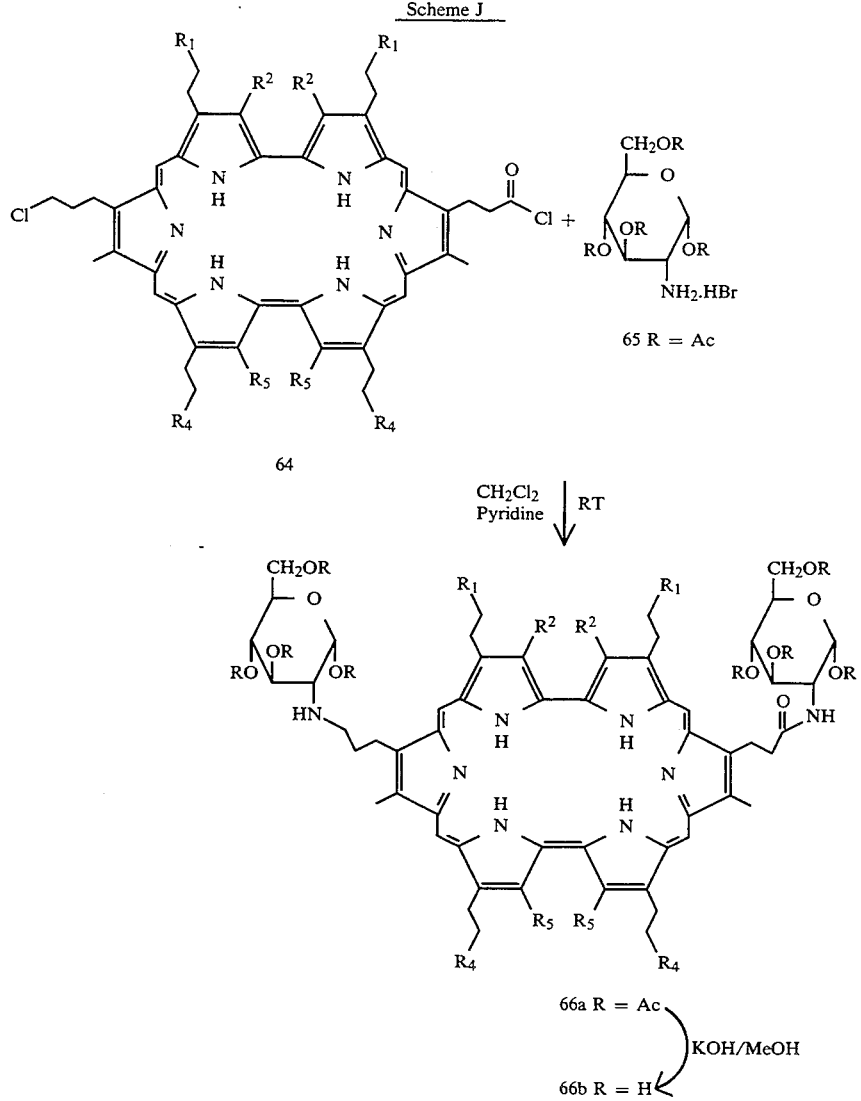
Scheme K
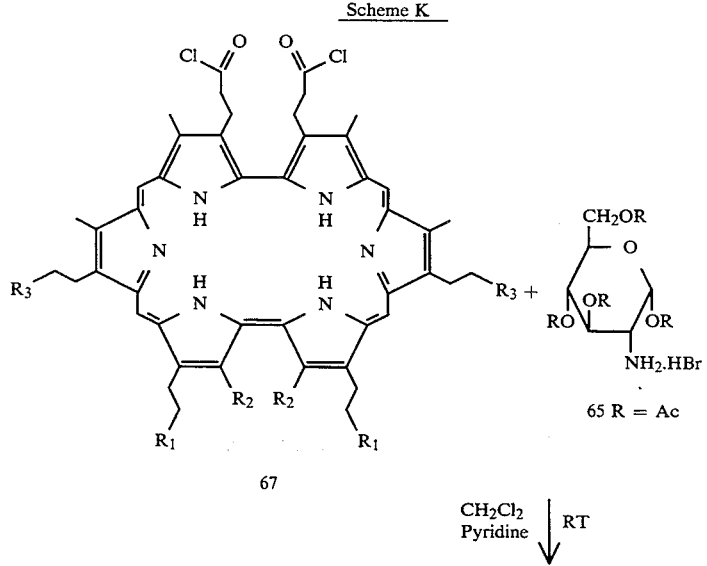

5,410,045
-continued
Scheme K
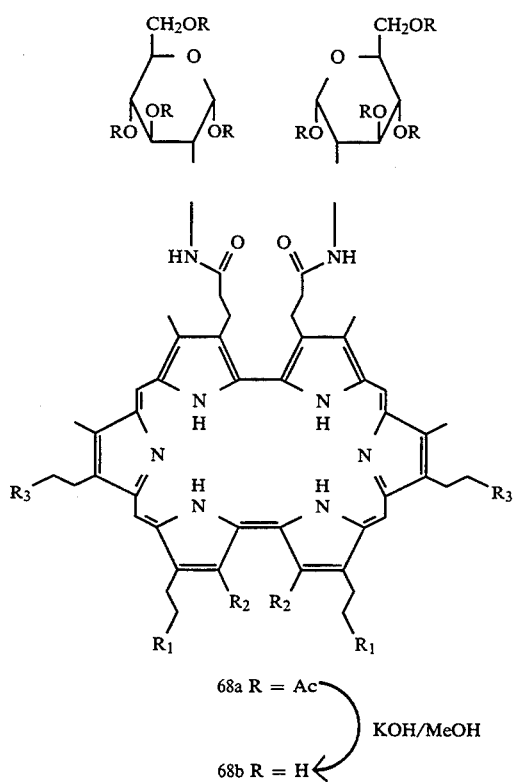
68a R = Ac  
68b R = H  } KOH/MeOH
Scheme L
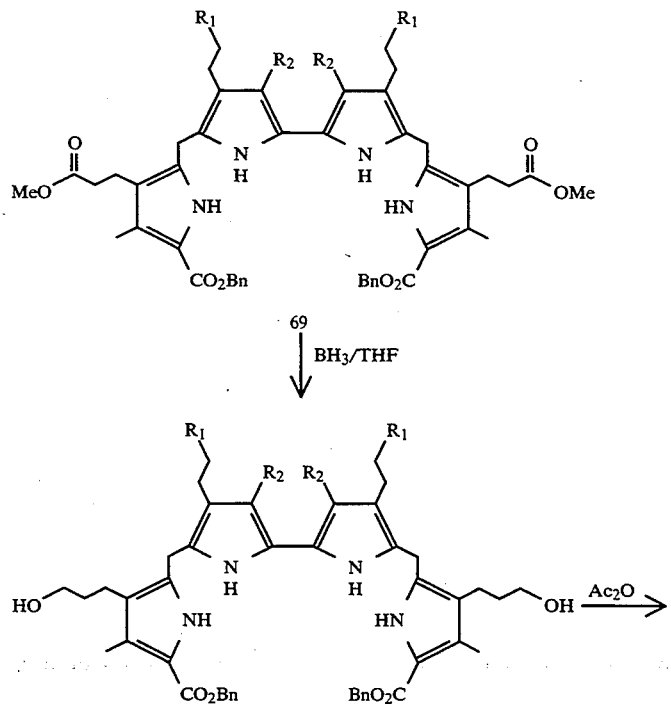

-continued
Scheme L
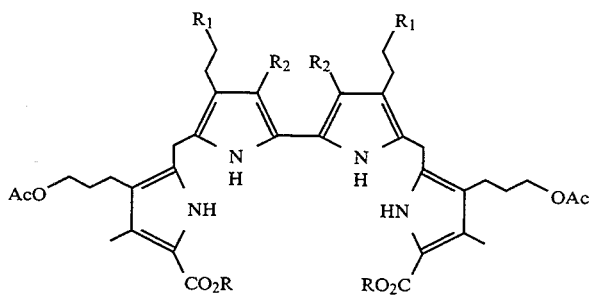
71a R = Bn
H₂, Pd/C
71b R = H
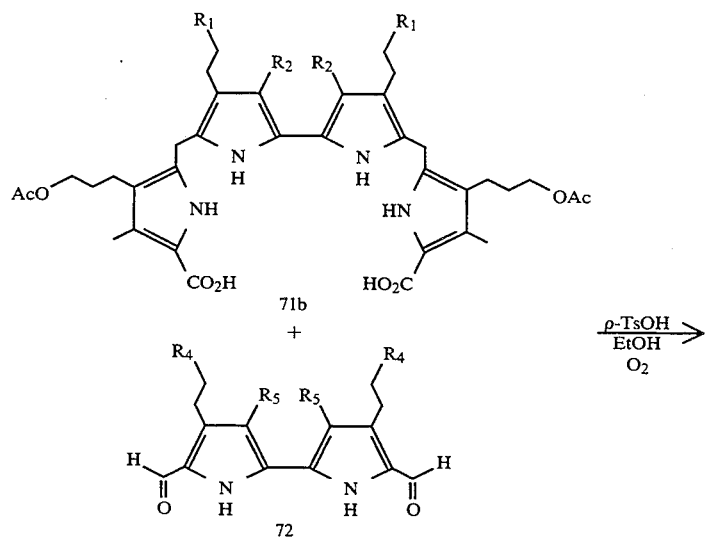
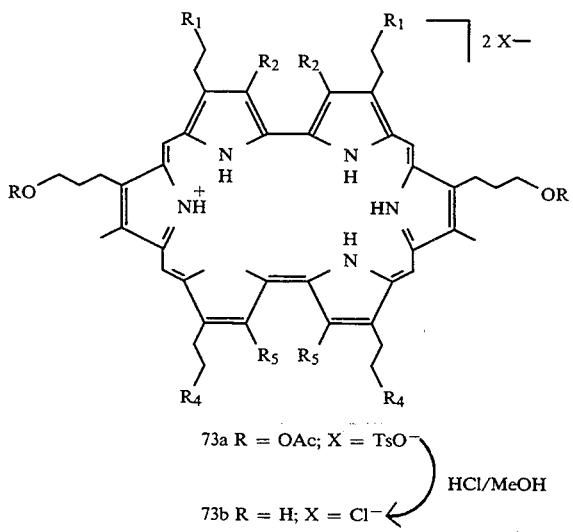
73a R = OAc; X = TsO⁻
HCl/MeOH
73b R = H; X = Cl⁻

Scheme M

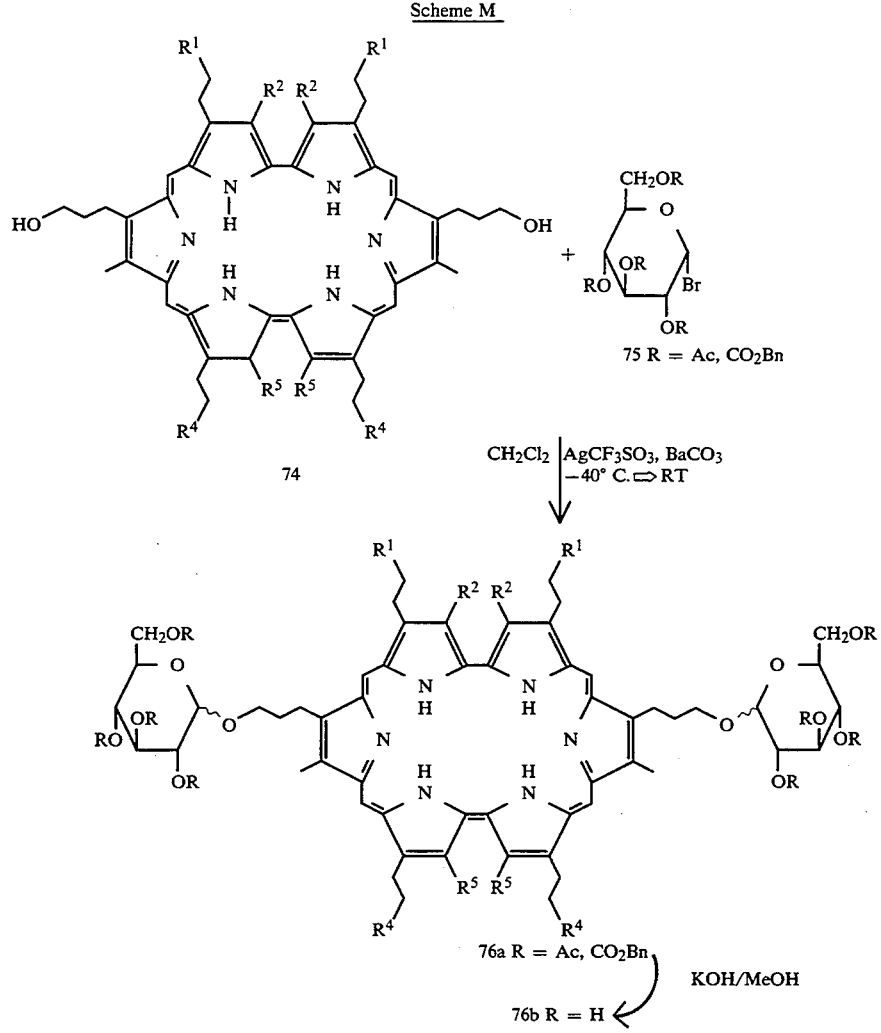

To prepare an ether linked bis(saccharide)rubyrin conjugate with the ether linkages in the 4 and 17 positions on the rubyrin periphery, the appropriate acetoxy-protected diformyl bipyrrole can be prepared as shown in Reaction Scheme N. Reduction of the methyl esters of bipyrrole 77 with borane-THF to the corresponding alcohols followed by protection with acetic anhydride provides the acetoxy-protected diol 79a. Standard debenzylation, to afford diacid 79b, followed by Clezy formylation with TFA and triethylorthoformate yields the acetoxy-protected bipyrrole 80. Condensation of bipyrrole 80 with diacid 81, under rubyrin-forming conditions, provides the acetoxy-protected dihydroxy rubyrin 82a. Deprotection of the hydroxyl groups can be achieved by treatment with HCl in methanol to afford dihydroxyrubyrin 82b.

The dihydroxyrubyrin thus formed can be coupled with acetoxy- and/or benzoyl-protected bromo-substituted saccharide units, such as structure 75 (Reaction Scheme O), in methylene chloride with silver triflate and barium carbonate to afford the acetoxy- and/or benzoyl-protected bis(saccharide)rubyrin conjugate 84a, as shown in Reaction Scheme O. Treatment of the acetoxy and/or benzoyl protected bis(saccharide)rubyrin 84a with KOH in methanol yields the corresponding deprotected bis(saccharide)rubyrin conjugate 84b (Reaction Scheme O).

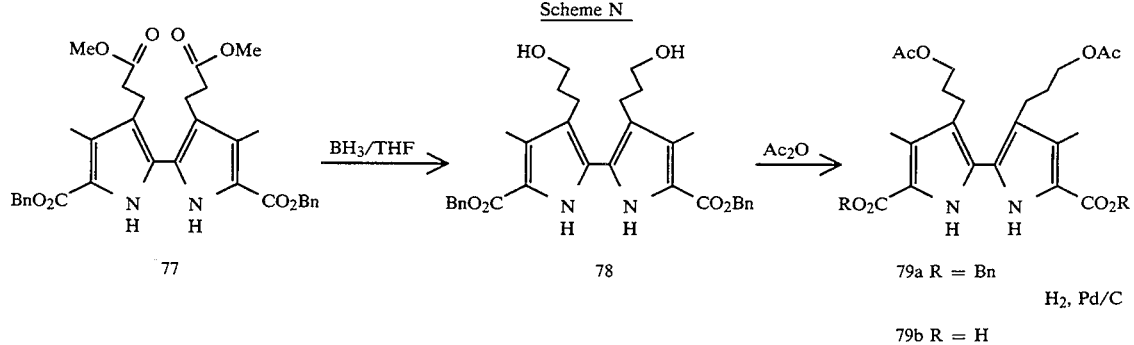
Scheme N
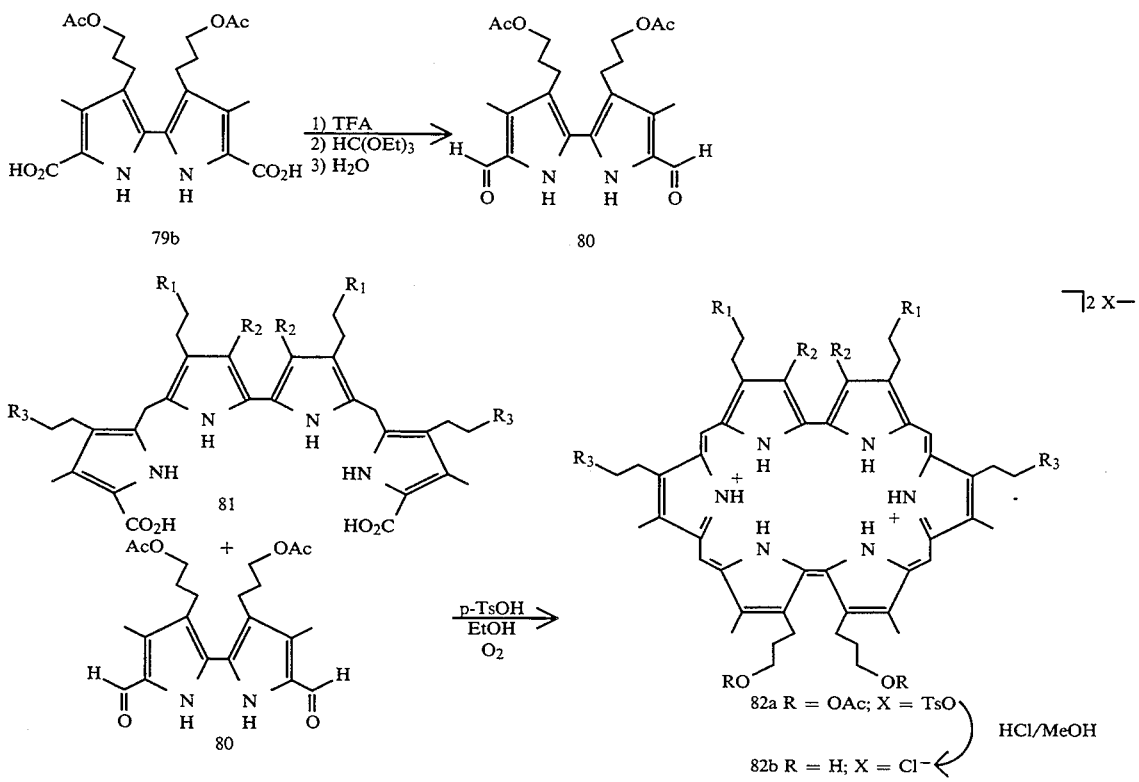
Scheme O
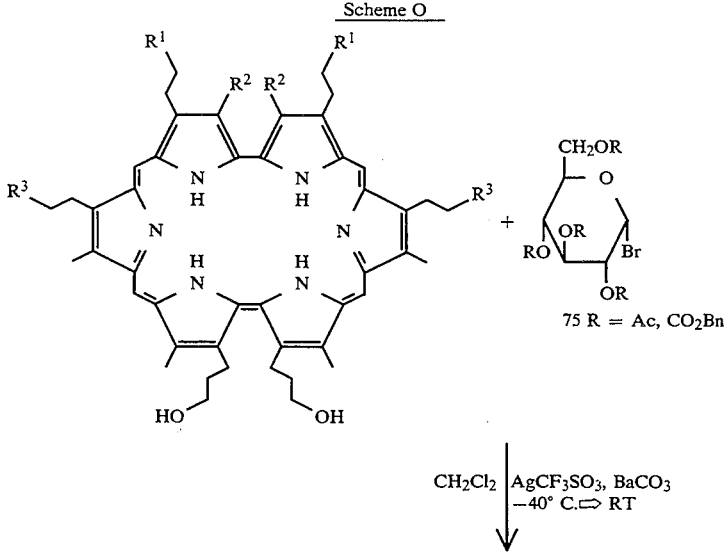

Scheme O

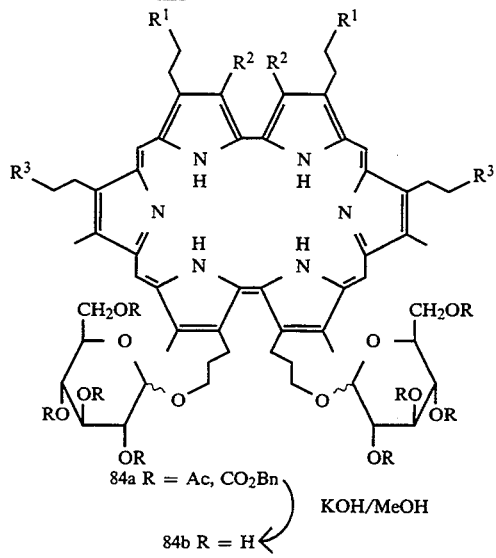

84a R = Ac, CO₂Bn
84b R = H
) KOH/MeOH

EXAMPLE X
SYNTHESIS OF RUBYRIN ANALOGUES EMPLOYING HETEROATOMS

In addition to the above rather direct extensions, the skilled artisan will appreciate that either bifuran and/or bithiophene subunits can be used in place of bipyrroles 11, 15, or 16 (FIG. 4A and FIG. 4B). Using a subunit substitution, which will be known to those of skill in the art in light of the present disclosure, will enable the preparation of heteroatom rubyrin-type compounds. These include, for example, those depicted by generalized structures 20-24 in FIG. 6, and structures 87, 92, 99 and 104 of Reaction Schemes P through S, respectively.

Figure 6:
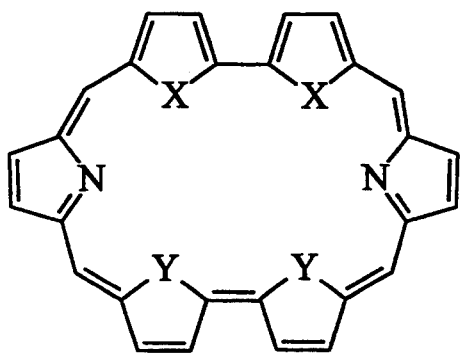
FIG. 6. Structures 20–24, rubyrin analogues employing heteroatoms, i.e., variously including nitrogen, oxygen and sulphur atoms. In that these structures are generally based upon FIG. 2D–FIG. 2F, it will be understood that they may also include any of the substituents listed above for $R_1$–$R_6$ and $X_1$–$X_4$, namely, H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether and substituted amide.

In light of the present disclosure and the recent work in the sapphyrin area, for example, Sessler et al, 1992[79], incorporated herein by reference, one of skill in the art would be able to prepare compounds of the general type shown in FIG. 6, and further exemplified in Reaction Scheme P through Reaction Scheme S. In particular, it is important to appreciate that 5,5'-diformyl-2,2'-bifuran and 5,5'-diformyl-2,2'-bithiophene are now readily available materials[79,80]. Simple condensation of these materials, in a normal rubyrin-forming manner, with a tetrapyrrolic fragment such as compound 14 of FIG. 4B would be expected, therefore, to produce rubyrin analogues of general class 22 and 23, in which two of the normal six pyrrolic nitrogens are replaced by sulfur or oxygen, respectively.

Reaction Schemes P through S represent examples of the synthesis of rubyrin analogues employing heteroatoms. The starting materials for use in the syntheses represented in these reaction schemes, and hence the resultant products, may include various substituents, such as, for example, H, alkyl, aryl, amino, hydroxyl, alkoxy, carboxy, carboxamide, ester, amide, sulfonato, hydroxy substituted alkyl, alkoxyl substituted alkyl, carboxy substituted alkyl, amino substituted alkyl, sulfonato substituted alkyl, ester substituted alkyl, amide substituted alkyl, substituted aryl, substituted alkyl, substituted ester, substituted ether, or substituted amide groups.

A synthetic scheme depicting the synthesis of such a rubyrin in which two of the normal six nitrogen heteroatoms are replaced by oxygen or sulfur is shown in Reaction Scheme P. The diacid tetrapyrrolic fragment 85 can be condensed with the readily available diformyl bifuran or diformyl bithiophene 86 under rubyrin-forming conditions, such as those described in Example I, to afford rubyrin analogue 87, where X can be either O or S.

Rubyrin analogues in which two different pyrrolic nitrogens have been replaced by the heteroatoms oxygen or sulphur may also be prepared, for example, as shown in Reaction Scheme Q. Condensation of bipyrrole 88 with the acetoxy-activated furan or thiophene 89 to produce the tetracycle 90, followed by condensation with bipyrrole 91, under rubyrin forming conditions such as those described in Example I, produces the 28π-electron rubyrin analogue 92, where X can be either oxygen or sulfur.

Reduction of bifuran or bithiophene fragments to the corresponding 5,5'-bisacetoxymethyl derivatives will provide precursors that, in analogy to the recent work in the heterosapphyrin area (Sessler et al, 1992[79] incorporated herein by reference), will allow, following condensation with benzyl 3-ethyl-4-methyl-pyrrole-2-carboxylate and subsequent hydrogenolysis (to remove the benzyl groups), the preparation of analogues of 14 in which the central tetraalkyl bipyrrole is replaced by either a bifuran or bithiophene moiety. Said analogues, following condensation with the appropriate diformyl-substituted bifuran or bithiophene, will allow, in turn, the preparation of rubyrin analogues of generalized structure 20, 21, and 24, with the exact class of compound prepared depending on whether a bifuran (or bithiophene) containing tetracycle is condensed with a bifuran or bithiophene bicycle, as would be appreciated by one of skill in the art.

A synthetic scheme depicting the synthesis of a rubyrin analogue with four of the nitrogen heteroatoms replaced by four oxygen or four sulfur atoms, or a combination of two oxygen and two sulphur atoms, is shown in Reaction Scheme R. The readily available compound 93, where X can be either O or S, can be reduced to the diol 94 by treatment with lithium aluminum hydride and subsequently acetoxy-protected with acetic anhydride to provide compound 95. Acid catalyzed condensation of bifuran or bithiophene 95 with benzyl 3-ethyl-4-methyl-pyrrole-2-carboxylate in isopropanol provides the tetracycle 97a. Standard hydrogenolysis of 97a with H₂ and Pd/C affords diacid 97b, which can be condensed with the bicyclic fragment 98 (where Y=O or Y=S), under rubyrin forming conditions, to produce rubyrin analogue 99, where X and Y can separately and independently be oxygen or sulfur.

Rubyrin analogues in which all six of the nitrogen atoms have been replaced by oxygen or sulfur heteroatoms may also be synthesized, for example, as shown in Reaction Scheme S. Condensation of the readily available bifuran or bithiphene 100 with the readily available acetoxy-activated furan or thiophene 101 affords the tetracycle 102. Condensing molecule 102 with a diformyl bifuran or diformyl bithiophene 103, under rubyrin forming conditions such as those described in Example I, will give the 28π-electron macrocycle 104 where X, Y, and Z may be any combination of oxygen or sulfur, based on starting materials chosen.

-continued
Scheme Q

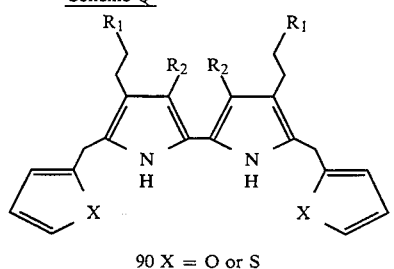

90 X = O or S

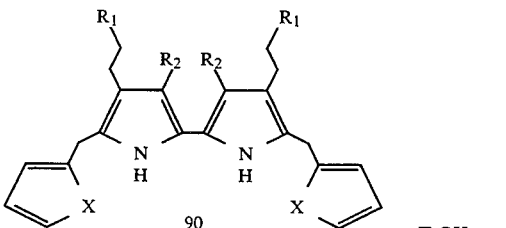

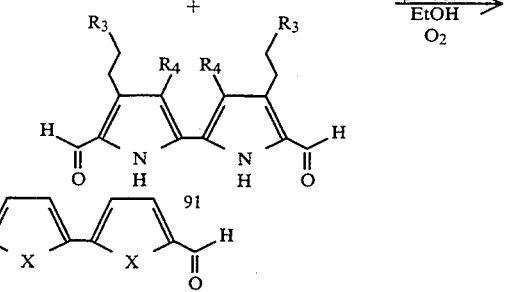

86 X = O or S

Scheme P

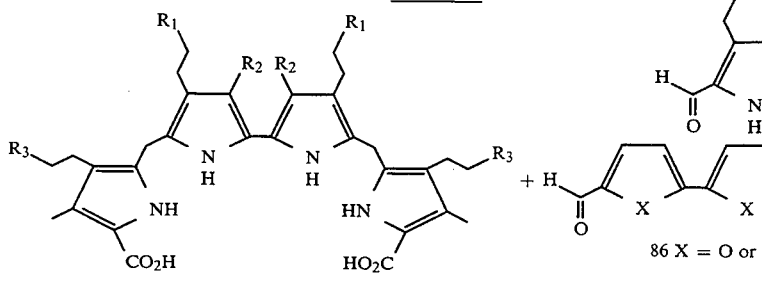

85

$$\xrightarrow[\text{O}_2]{\substack{\text{p-TsOH}\\\text{EtOH}}}$$

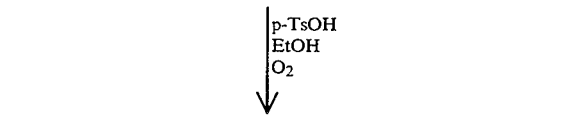

]2 TsO—

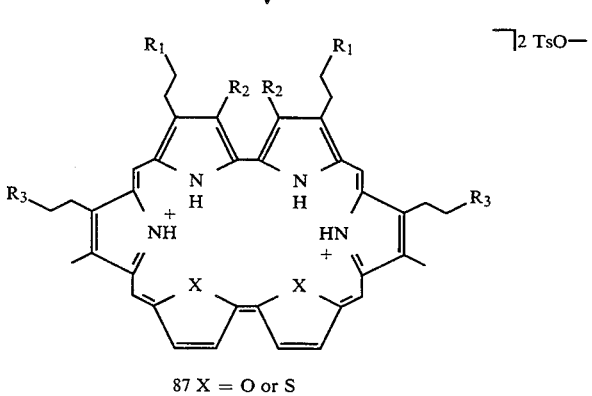

87 X = O or S

Scheme Q

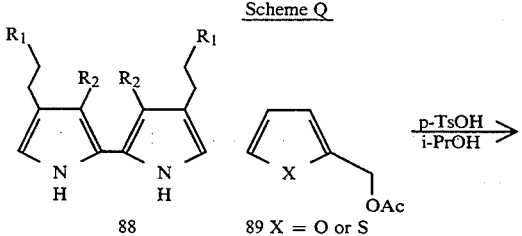

88    89 X = O or S $$\xrightarrow[\text{i-PrOH}]{\text{p-TsOH}}$$

60

65

5,410,045
-continued
Scheme Q
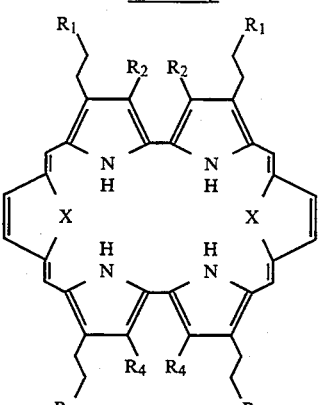
92 X = O or S
Scheme R
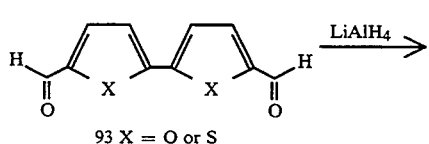
93 X = O or S
94 X = O or S
95 X = O or S
95 X = O or S
+
96
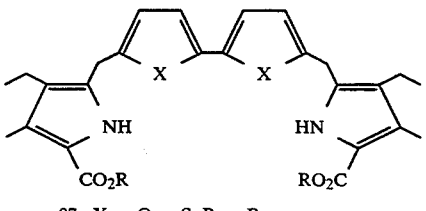
97a X = O or S; R = Bn
97b X = O or S; R = H  $\Big\uparrow$ H₂, Pd/C
-continued
Scheme R
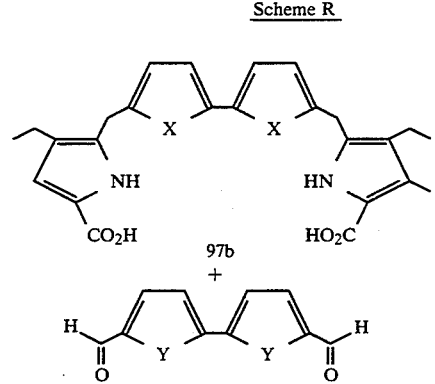
97b
+
98 X = O or S
$\xrightarrow{\text{p-TsOH} \atop \text{EtOH} \atop O_2}$
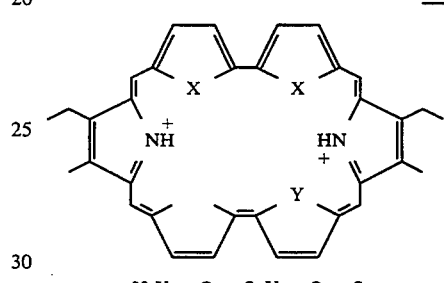
99 X = O or S; Y = O or S
Scheme S
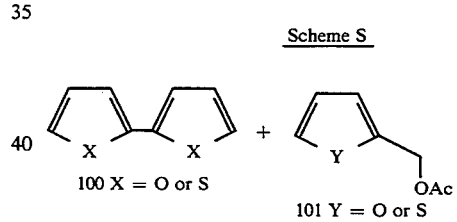
100 X = O or S    101 Y = O or S
$\xrightarrow{\text{p-TsOH} \atop \text{i-PrOH}}$
102 X, Y = O or S
102
103 Z = O or S
$\xrightarrow{\text{p-TsOH} \atop \text{EtOH} \atop O_2}$ -continued
Scheme S

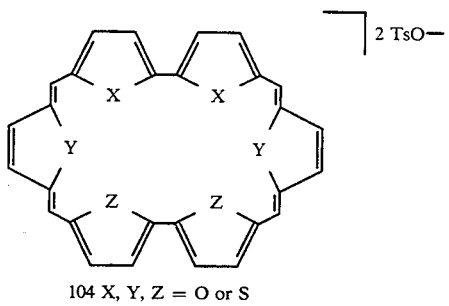

104 X, Y, Z = O or S

With such heteroatomic compounds, one may determine how changes in size, shape, and macrocycle denticity (the number of "coordinating" NH groups) affect monophosphate binding, and also define the basic structural parameters associated with efficient through-membrane transport of GMP-like species. Developing this theme will allow a determination of how these same changes in core structure are reflected in terms of an ability (or lack thereof) to bind and transport other ·phosphorylated species, including such important species as cyclic nucleotide monophosphates (e.g. c-AMP), diphosphates (e.g. GDP), and triphosphates (e.g. ATP). Also, the extent to which these systems, and/or their monoprotonated derivatives, can act as receptors/carriers for various halides, including, of course, chloride anion may be investigated.

Furthermore, it is again contemplated that some or all of the β-pyrrolic positions in these systems may be substituted with alkyl or functionalized alkyl substituents. Thus, a wide variety of structures are conceived within the context of the basic synthetic methodology presented in FIG. 4A and FIG. 4B.

EXAMPLE XI

RUBYRIN AND RUBYRIN ANALOGUE AS CHELATING RECEPTORS

To date, labile bis-zinc derivatives of 10a and 10b have been made. However, it is envisioned that the diprotonated rubyrin systems will act as effective receptors for a variety of anions, as is true for sapphyrin when protonated[4,6], and possibly other cationic expanded porphyrins[12-14]. For instance, preliminary spectroscopic studies with system 10a indicate that diprotonated rubyrin can bind both fluoride and phosphate anions in a strong and non-labile manner.

Furthermore, the monoprotonated form of rubyrin 10a has been shown to act as an effective carrier for the through-membrane transport of guanosine-5′-monophosphate in Pressman type model system. In light of these results, protonated rubyrins are proposed to be of use in a variety of molecular recognition applications, that are not within the purview of normal tetrapyrrolic porphyrin chemistry.

Once a range of rubyrin analogues have been generated, for example, as described herein in the foregoing detailed examples, the thermodynamics and kinetics of anion binding under a range of conditions and with an array of different anions may be determined. The structure and function of the most promising rubyrin compounds may then be optimized such that they bind either phosphate-bearing nucleotides, or chloride ions, with high affinity and selectivity at neutral pH.

As a complement to structural studies, quantitative analyses may also be conducted. For example, the relevant $pK_a'$ values for various rubyrins may be determined by employing the methods previously used to determine the $pK_a'$ values for sapphyrin and anthraphyrin[16h,6a]. One should beware of possible "artifacts" arising from anion chelation, which can be avoided by using non-chelating buffers and solvents. Such initial studies should be followed by ones in which the various $pK_a'$ values are recorded in different solvents and in the presence of different anions such as hydrosulfate, bicarbonate, azide, cyanide, fluoride, bromide, and iodide, that are of biological relevance. Other qualitative tests (e.g. UV/vis, FABMS) may also be used to reconfirm that rubyrins do not form complexes under physiological conditions with $Na^+$, $K^+$, $Ca^{2+}$, or other biocations. The reason for these latter studies is that such cation complex formation could preclude efficient anion binding and transport.

Once $pK_a'$ values are recorded, a second set of quantitative analyses may be performed to determine the actual affinity constants for each and every relevant receptor-to-anionic interaction. Thus, for instance, $K_s$ for $[H_6Rub^{2+}\cdot GMP^{2-}]$ formation in a variety of solvent systems may be measured in a similar manner to that for the hydrohalide salts of sapphyrin and anthraphyrin-[16h]. Standard methods as quantitative UV/vis titrations and concentration dependent NMR chemical shift analyses may be used, along with more sophisticated techniques such as those involving static and time-resolved fluorescence. The inventors have determined that the latter methods offer considerable advantages and are particularly useful for measuring high affinity constants (i.e. those in the $K_s \geq 10^6$ $M^{-1}$ range). These fluorescence-based methods require highly colored materials with good singlet state emission characteristics, but these criteria are clearly met by the rubyrins.

Quantitative kinetic studies may also be carried out and used to determine whether the rate limiting step in GMP (or chloride) transport involves initial receptor-anion complex formation, through-membrane carrier-complex diffusion, product release, and/or rate of carrier back-diffusion. On- and off-rates for complex formation may be measured, for example, by dynamic NMR, UV/vis, or time-resolved fluorescence, in, e.g., simple water-saturated dichloromethane solutions. More precise analyses of receptor-mediated transport may also be made, again with a mind to determining what are the dynamics of complexation and decomplexation. The U-tube model system may be employed, and when appropriate, more sophisticated membrane analogues such as mixed phosphatidylcholine-cholesterol liposomes can be used[18a].

For the latter studies, it may prove most convenient to prepare nucleotide or halide encapsulating liposomes and then determine the kinetics of anion extrusion as a function of carrier concentration and/or external solution pH. Here again, either UV/vis or time-resolved fluorescence analyses may be used. Here, it might prove necessary to add a specific fluorophore, such as 6-methoxy-N-(3-sulphopropyl)quinolinium (a halide selective reagent) to the outside phase so as to be able to detect small quantities of the anionic "escapees".

EXAMPLE XII

RUBYRIN AND ANALOGUES AS CELLULAR ANION TRANSPORTERS

In preliminary transport screening studies, using a $H_2O$—$CH_2Cl_2$-$H_2O$ Pressman-type[6,70,74] U-tube model system, rubyrin was found to be capable of effecting through-membrane transport of GMP and other nucleotides at near-neutral pH (i.e. in the pH 6.0 to 6.5 regime). In contrast, sapphyrin was completely ineffective, and pentaphyrin mediated only very slow GMP transport, which was further, and unfortunately, subject to inhibition by chloride anions. Thus, it is clear that for any conceivable phosphate chelation or recognition applications the rubyrins will emerge as being vastly superior to either the pentaphrins or sapphyrins.

The effective transport by rubyrin, a larger, more basic system, may derive from lower in-core $NH^+$—to—$NH^+$ repulsions. In any event, these properties make rubyrin an ideal candidate for use in the delivery of phosphorylated compounds such as antivirals. The ability of rubyrin to effect nucleotide transport in a manner that is free of any chloride (or other halide) anion inhibition (even though this same material binds chloride anion quite effectively at very low pH and in the solid state) is particularly important.

Furthermore, the inventors determined that transport effected by this latter rubyrin carrier could be made somewhat nucleobase selective by adding the appropriate complementary TIPS derivative to the organic membrane phase. For example, in the presence of C-Tips (triisopropylsilyl-protected cytidine), the rate of rubyrin-mediated GMP transport was observed to be substantially enhanced. Results from such exploratory studies thus support not only the suggestion that it should be possible to effect base-specific phosphate (or phosphonate) entity transport under physiological conditions, but also the contention that by synthetic "selection" or "fine tuning" it should be possible to design rubyrin anion receptors that are selective for either phosphate-derived antivirals, or chloride anion, or both.

In further studies, those kinetic and thermodynamic factors that militate both for and against rapid, selective transport of phosphorylated nucleotides and nucleotide analogues can be precisely determined. Both the use of simple U-tube and more elaborate liposomal test systems is contemplated.

EXAMPLE XIII

USE OF RUBYRIN AND ANALOGUES AS THERAPEUTIC AGENTS

Rubyrin compounds of the present invention are contemplated to be of use as anion transporters in various embodiments relating to human treatment. They are particularly contemplated for use as delivery agents for antiviral compounds and may thus be employed to combat a variety of diseases including AIDS, herpes, hepatitis and measles. Rubyrin compounds optimized for chloride transport are also contemplated for use in the treatment of cystic fibrosis.

In developing the rubyrin compounds of the present invention for therapeutic use as anti-viral transporters, in vitro tests will first be conducted. These will follow protocols similar to those used earlier to screen the photodynamic antiviral activity of sapphyrin and several other expanded porphyrins[18b]. In brief, a monolayer of Vero cells will be infected with HSV-1, coated with an overlay culture medium, and then exposed to various relative and absolute concentrations of both putative carrier and known active antiviral. Then, following incubation at 37° C., adjuvant efficacy will be determined by counting the number of plaque forming units (PFU) obtained in the presence and absence of a given carrier.

Following such in vitro tests, the activity of promising rubyrin receptors will be followed-up, for example, in anti-HIV screens, and then in in vivo animal studies. These studies will be conducted according to the standard practice for such animal trials, the execution of which will be known to those of skill in the art.

During the animal trial stage, the rubyrin compounds, whether used in antiviral delivery, or for chloride transport in cystic fibrosis treatment, may be modified further if required. They might, for instance, be modified to overcome poor water solubility or susceptibility to in vivo degradation. Alternatively, if such problems occur, the rubyrins could be enveloped within a bio-compatible liposome (made, e.g. from Cremophor)[73] and then administered intravenously. Such an approach has previously resulted in good in vivo murine adenocarcinoma photodynamic tumor killing with a water-insoluble texaphyrin-type expanded porphyrin[74]. The "Trojan Horse" method[75] could also be employed to deliver the rubyrin antiviral carrier in vivo to the desired locus of biological activity. Here, the idea would be to use non-infectious viral membrane material to produce liposomes and then use these in turn as transport vehicles to get the putative carrier to the site of cellular infectivity.

Naturally, toxicity studies will also be carried out at this stage. The methods for determining both acute and chronic toxicity will be known to those of skill in the art. Available evidence indicates that rubyrins, like sapphyrins, will be relatively nontoxic. Toxicity can be investigated in relation to solubility, net charge at physiologic pH, and changes in appended S-pyrrolic and/or meso substituents.

Furthermore, the phosphate-binding rubyrin compounds of the present invention may act as receptors and transporters for other biologically important molecules with negative charges, particularly, polynucleic acids such as DNA, RNA and oligonucleotides. Another dimension to the invention, therefore, concerns the possibility of using rubyrins in the transport of DNA molecules, such as antisense DNA constructs, into cells for use in so-called gene therapy programs.

Normal cellular uptake of negatively-charged DNA is known to be limited. Current in vitro methods rely on severe cellular modifications which often cause excessive cell damage[76] and as a result, are not viable in vivo. The "coating" of nucleic acid phosphate groups with rubyrins, thus rendering them suitable for diffusional uptake in vivo, is therefore very attractive and even has implications for chromosomal gene therapy.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

1. Sessler, J. L., A. K. Burrell, Top. Curr. Chem. 161 1991 177–273.
2. Broadhurst, M. J., R. Grigg, A. W. Johnson, J. Chem. Soc., Perkin Trans. 1 1972, 2111–2116.
1. Bauer, V. J., D. L. J. Clive, D. Dolphin, J. B. Paine, III, F. L. Harris, M. M. King, J. Loder, S. -W. C. Wang, R. B. Woodward, J. Am. Chem. Soc. 105 1983 6429–6436.
4. (a) Sessler, J. L., M. J. Cyr, V. Lynch, E. McGhee, J. A. Ibers, J. Am. Chem. Soc. 112 1990 2810–2813. (b) Shionoya, M., H. Furuta, V. Lynch, A. Harriman, J. L. Sessler, J. Am. Chem. Soc. 114 1992, 5714–5722.
5 (a) Burrell, A. K., J. L. Sessler, M. J. Cyr, E. McGhee, J. A. Ibers, Angew. Chem. 103 1991 83–85; Angew. Chem. Int. Ed. Engl. 30 (1991) 91–93. (b) Sessler, J. L., M. J. Cyr, A. K. Burrell, Synlett. 1991 127–133.
6. (a) Sessler, J. L., D. Ford, M. J. Cyr, H. Furuta, J. Chem. Soc., Chem. Commun. 1991, 1733–1735. (b) Furuta, H., M. J. Cyr, J. L. Sessler, J. Am. Chem. Soc. 113 1991 6677–6678.
7. Rexhausen, H., A. Gossauer, J. Chem. Soc., Chem. Commun. 1983, 275.
8. Burrell, A. K., G. Hemmi, V. Lynch, J. L. Sessler, J. Am. Chem. Soc. 113 1991 4690–4692.
9. Gossauer, A., Bull. Soc. Chim. Belg. 92 1983 793–795.
10. (a) Day, V. W., T. J. Marks, W. A. Wachter, J. Am. Chem. Soc. 97 1975 4519–4527; (b) Marks, T. J., D. R. Stojakovic, ibid. 100 1978 1695–1705; (c) Cuellar, E. A., T. J. Marks Inorg. Chem. 20 1981 766–3770.
11. (a) Berger, R. A., E. LeGoff, Tetrahedron Lett. 1978, 4225–4228; (b) LeGoff, E., O. G. Weaver, J. Org. Chem. 52 1987 710–711.
12. (a) Gosmann, M., B. Franck, Angew. Chem. 98 1986 1107–1108; Angew. Chem. Int. Ed. Engl. 25 1986 1100–1101; (b) Knübel, G., B. Franck, ibid. 100 1988 1203–1211 and 27 1988 1170–1172.
13. (a) Gosmann, M., A. Vogt, B. Franck, Liebigs Ann. Chem. 1990, 163–168; (b) Konig, H., C. Eickemeier, M. Möller, U. Rodewald, B. Franck, Angew. Chem. 102 1990 1437–1439; Angew. Chem. Int Ed. Engl. 29 1990 1393–1395.
14. (a) Jux, N., P. Koch, H. Schmickler, J. Lex, E. Vogel, Angew. Chem. 102 1990 1429–1431; Angew. Chem. Int. Ed. Engl. 29 1990 1385–1387; (b) Vogel, E., N. Jux, E. Rodriguez-Val, J. Lex, H. Schmicker, ibid. 102 1990 1431–1434 and 29 1990 1387–1390.
15. (a) Sessler, J. L., T. Murai, V. Lynch, M. Cyr, J. Am. Chem. Soc. 110 1988 5586–5588; (b) Sessler, J. L., T. Murai, G. Hemmi, Inorg. Chem. 28 1989 3390–3393. (c) Maiya, B. G., T. E. Mallouk, G. Hemmi, J. L. Sessler, Inorg. Chem. 29 1990, 3738–3745.
16. (a) Acholla, F. V., K. B. Mertes, Tetrahedron Lett. 1984, 3269–3270; (b) Acholla, F. V., F. Takusagawa, K. B. Mertes, J. Am. Chem. Soc. 107 1985 6902–6908; (c) Adams, H., N. A. Bailey, D. A. Fenton, S. Moss, C. 0. Rodriguez de Barbarin, J. Chem. Soc. Dalton Trans. 1986, 693–699; (d) Sessler, J. L., V. Lynch, M. R. Johnson, J. Org. Chem. 52 (1987), 4394–4397. (e) Fenton, D. E., R. Moody, ibid. 1987, 2199–220; (f) Schumacher, K.-H., B. L. Franck, Angew. Chem. 101 1989 1292–1294; Angew. Chem. Int. Ed. Engl. 28 1989 1243–1245. (g) Sessler, J. L., T. D. Mody, V. Lynch, Inorg. Chem. 31 1992 529–531. (h) Sessler, J. L., T. D. Mody, D. Ford, V. Lynch, Angew. Chem. 104 1992 461–464; Angew. Chem., Int. Ed. Engl. 31 1992 452–455.
17. Johnson, M. R., D.C. Miller, K. Bush, J. J. Becker, J. A. Ibers J. Org. Chem. 57 1992, in press.
18. (a) J. L. Sessler, M. Cyr, B. G. Maiya, M. L. Judy, J. T. Newman, H.Skiles, R. Boriack, J. L. Matthews, T. C. Chanh, Proc. SPIE Int. Opt. Eng. 1203 (Photodynamic Therapy: Mechanisms II) 1990 233–245; (b) M. L. Judy, J. L. Matthews, J. T. Newman, H. Skiles, R. Boriack, M. Cyr, B. G. Maiya, J. L. Sessler, Photochem. Photobiol. 53 1991 101–107; (c) J. L. Sessler, G. Hemmi, B. G. Maiya, A. Harriman, M. L. Judy, R. Boriak, J. L. Matthews, B. Ehrenberg, Z. Malik, Y. Nitzan, A. Rück, Proc. SPIE Int. Opt. Eng. 1991, 1426, 318–328; (d) F.-Y. Shiau, P. A. Liddell, G. H. Vicente, N. V. Ramana, K. Ramachandran, S.-J. Lee, R. K. Pandey, T. J. Dougherty, K. M. Smith, Proc. SPIE Int. Opt. Eng. IS 6 1989 71–86; (e) B. Franck, G. Fulling, M. Gosmann, G. Knubel, H. Mertes, D. Schroder, Proc. SPIE Int. Soc. Opt. Eng. Ser. 5, 997 1988 107–112; (f) S. Beckmann, T. Wessel, B. Franck, W. Hönle, H. Borrmann, H.-G. von Schnering, ibid. 102 1990 1439–1441 and 29 1990 1395–1397; (g) S. Beckmann, T. Wessel, B. Franck, W. Hönle, H. Borrmann, H.-G. von Schnering, ibid. 102 1990 1439–1441 and 29 1990 1395–1397.
19. Sessler, J. L., T. Morishima, V. Lynch, Angew. Chem. 103 1991 1018–1021; Angew. Chem., Int. Ed. Engl. 30 1991 977–980.
20. Johnson, A. W., I. T. Kay, E. Markham, P. Price, K. B. Shaw, J. Chem. Soc. 1959 3416–3424.
21. Arsenault, G. P., E. Bullock, S. F. MacDonald, J. Am. Chem. Soc. 82 1960 4384–4389.
22. Vogel, E., M. Balci, K. Pramod, P. Koch, J. Lex, O. Ermer, Angew. Chem. 99 1987 909; Angew. Chem., Int. Ed. Engl. 26 1987 928.
23. (a) Cetinkaya, E., A. W. Johnson, M. F. Lappert, G. M. MacLaughlin, K. W. Muir, J. Chem. Soc. Dalton Trans 1 1974 1236–1243; (b) Stone, A., E. B. Fleischer, J. Am. Chem. Soc. 90 1968 2735–2748.
24. Sessler, J. L., H. Furuta, V. Kral, Supramol. Chem., 1992, "In Press."
25. Robins, R. K. Chemical and Engineering News January 1986, 28–40.
26. "Approaches to Antiviral Agents," Harden, M. R., Ed.; VCH Publishers: Deerfield Beach, Florida, 1985.
27. Holy, A. In "Approaches to Antiviral Agents," Harden, M. R., Ed.; VCH Publishers: Deerfield Beach, Florida, 1985. pp. 101–134.
28. (a) Tabushi, I.; Kobuke, Y.; Imuta, J. J. Am. Chem. Soc. 1980, 102, 1744–1745. (b) Tabushi, I.; Kobuke, Y.; Imuta, J. J. Am. Chem. Soc. 1981, 103, 6152–6157.
29. (a) Mertes, M.P.; Mertes, K. B. Acc. Chem. Res. 1990, 23, 413–418. (b) Hosseini, M. W.; Lehn, J.-M. J. Chem. Soc., Chem. Commun. 1991, 451–453. (c) Hosseini, M. W.; Lehn, J.-M.; Jones, K. C.; Plute, K. E.; Mertes, K. B.; Mertes, M. P. J. Am. Chem. Soc. 1989, 111, 6330–6335. (d) Lehn, J.-M. Angew. Chem. Int. Ed. Engl. 1988, 27, 89–112, and references therein.

30. (a) Hosseini, M. W.; Blacker, A. J.; Lehn, J.-M. J. Chem. Soc., Chem. Commun. 1988, 596–598. (b) Idem. J. Am. Chem. Soc. 1990, 112, 3896–3904.
31. (a) Dietrich, B.; Hosseini, M. W.; Lehn, J.-M.; Sessions, R. B. J. Am. Chem. Soc. 1981, 103, 1282–1283. (b) Dietrich, B.; Guilhem, J.; Lehn, J.-M.; Pascard, C.; Sonveaux, E. Helv. Chim. Acta 1984, 67, 91–104.
32. Kimura, E.; Kuramoto, Y.; Koike, T.; Fujioka, H.; Kodama, M. J. Org. Chem. 1990, 55, 42–46.
33. Kimura, E. Top. Curr. Chem. 1985, 128, 113–141, and references therein.
34. Umezawa, Y.; Kataoka, M.; Takami, W.; Kimura, E.; Koike, T.; Nada, H. Anal. Chem. 1988, 60, 2392–2396.
35. (a) Schmidtchen, F. P. Chem. Ber. 1981, 114, 597–607. (b) Schmidtchen, F. P. Top. Curr. Chem. 1986, 132, 101–133, and references therein.
36. (a) Marecek, J. F.; Fischer, P. A.; Burrows, C. J. Tetrahedron Lett. 1988, 29, 6231–6234. (b) Marecek, J. F.; Burrows, C. J. Tetrahedron Lett. 1986, 27, 5943–5946.
37. (a) Nakai, C.; Glinsmann, W. Biochemistry, 1977, 25, 5636–5640. (b) Woo, N.H.; Seeman, N. C.; Rich, A. Biopolymers, 1979, 18, 539–552. (c) Wilson, H. R.; Williams, R. J. P. J. Chem. Soc., Faraday Trans. 1 1987, 83, 1885–1892.
38. Claude, S.; Lehn, J.-M; Schmidt, F.; Vigneron, J.-P. J. Chem. Soc., Chem. Commun. 1991, 1182–1185.
39. (a) Dietrich, B.; Fyles, T. M.; Lehn, J.-M.; Pease, L. G.; Fyles, D. L. J. Chem. Soc., Chem. Commun. 1978, 934–936. (b) Dietrich, B.; Fyles, D. L.; Fyles, T. M.; Lehn, J.-M. Helv. Chim. Acta 1979, 62, 2763–2787.
40. Schmidtchen, F. P. Tetrahedron Lett. 1989, 30, 4493–4496.
41. Galán, A.; Pueyo, E.; Salmerón, A.; de Mendoza, J. Tetrahedron Lett. 1991, 32, 1827–1830.
42. Galán, A.; de Mendoza, J.; Toiron, C.; Bruix, M.; Delongchamps, G.; Rebek, J., Jr. J. Am. Chem. Soc. 1991, 113, 9424–9425.
43. Dixon, R. P.; Geib, S. J.; Hamilton, A.D. J. Am. Chem. Soc. 992, 114, 365–366.
44. Ariga, K.; Anslyn, E. V. J. Org. Chem., 1992 in press.
45. Sasaki, D. Y.; Kurihara, K.; Kunitake, T. J. Am. Chem. Soc. 1991, 113, 9685–9686; Kurihara, K.; Ohto, K.; Honda, Y.; Kunitake, T. J. Am. Chem. Soc. 1991, 113, 5077–5079.
46. Salehi, A.; Mei, H.-Y.; Bruice, T. C. Tetrahedron Lett. 1991, 32, 3453–3456.
47. Muehldorf, A. V.; Van Engen, D.; Warner, J. C.; Hamilton, A. D. J. Am Chem. Soc. 1988, 110, 6561–6562.
48. Adrian, J. C.; Wilcox, C. S. J. Am. Chem. Soc. 1989, 111, 8055–8057.
49. Benzing, T.; Tjivikua, T.; Wolfe, J.; Rebek, J., Jr. Science, 1988, 242, 266–268.
50. Seel, C.; Vögtle, F. Angew. Chem. Int. Ed. Engl. 1991, 30, 442–444.
51. Goodman, M. S.; Rose, S. D. J. Am. Chem. Soc. 1991, 113, 9380–9382.
52. Lindsey, J. S.; Kearney, P. C.; Duff, R. J.; Tjivikua, T.; Rebek, J., Jr. J. Am. Chem. Soc. 1988, 110, 6575–6577.
53. Ogoshi, H.; Hatekeyama, H.; Kotani, J.; Kawashima, A.; Kuroda, Y. J. Am. Chem. Soc. 1991, 113, 8181–8183.
54. Weiss, R. Science News 1991, 139, 132.
55. Quinton, P. M. FASEB 1990, 4, 2709–2717.
56. (a) Welsh, M. J.; Smith, A. E.; Gregory, R. J.; Rich, D. P.; Anderson, M.P. Science 1991, 251, 679–682. (b) Riordan, J. R. ; Bear, C. E. ; Rommens, J. M.; Tsui, L.; Reyes, E. F.; Ackerley, C. A.; Sun, S.; Naismith, A. L.; Jensen, T. T.; Hanrahan, J. W.; Kartner, N. Cell 1991, 64, 681–691.
57. (a) Welsh, M. J.; Smith, A. E.; Manavalan, P.; Anderson, M. P.; Gregory, R. J.; Rich, D. P. Science 1991, 253, 205–207. (b) Welsh, M. J.; Smith, A. E.; Mulligan, R. C.; Souza, D. W.; Paul, S.; Thompson, S.; Gregory, R. J.; Anderson, M.P. Science 1991, 253, 202–205.
58. (a) Cheng, S. H.; Rich, D. P.; Marshall, J.; Gregory, R. J.; Welsh, M. J.; Smith, A. E. Cell 1991, 66, 1027–1036. (b) Anderson, M.P.; Barger, H. A.; Rich, D. P.; Gregory, R. J.; Smith, A. E.; Welsh, M. J. Cell 1991, 67, 775–784.
59. Davis, P. B. N. Engl. J. Med. 1991, 325, 575–577.
60. Park, C. H.; Simmons, H. E. J. Am. Chem. Soc. 1968, 90, 2431–2432.
61. (a) Graf, E.; Lehn, J.-M. J. Am. Chem. Soc. 1976, 98, 6403–6405. (b) Kintzinger, J.-P.; Lehn, J.-M.; Kauffmann, E.; Dye, J. L.; Popov, A. I. J. Am. Chem. Soc. 1983, 105, 7549–7553. (c) Hosseini, M. W.; Kintzinger, J.-P.; Lehn, J.-M.; Zahidi, A. Helv. Chim. Acta, 1989, 72, 1078–1083.
62. Dietrich, B.; Lehn, J.-M.; Guilhem, J.; Pascard, C. Tetrahedron Lett. 1989, 30, 4125–4128.
63. Dietrich, B.; Fyles, T. M.; Hosseini, M. W.; Lehn, J.-M.; Kaye, K. C. J. Chem. Soc., Chem. Commun. 1988, 691–692.
64. Cramer, R. E.; Fermin, V.; Kuwabara, E.; Kirkup, R.; Selman, M.; Aoki, K.; Adeyemo, A.; Yamazaki, H. J. Am. Chem. Soc. 1991, 113, 7033–7034.
65. Beauchamp, A. L.; Olievier, M. J.; Wuest, J. D.; Zacharie, B. J. Am. Chem. Soc. 1986, 108, 73–77.
66. Blanda, M. T.; Newcomb, M. Tetrahedron Lett. 1989, 27, 3501–3504.
67. Jung, M. E.; Xia, H. Tetrahedron Lett. 1988, 29, 297–300.
68. Katz, H. E. J. Am. Chem. Soc. 1986, 108, 7640–7645.
69. (a) Yang, X.; Knobler, C. B.; Hawthorne, M. F. Angew. Chem. Intl. Ed. Engl. 1991, 30, 1507–1508. (b) Yang, X.; Knobler, C. B.; Hawthorne, M. F. J. Am. Chem. Soc. 1992, 114, 380–382.
70. Furuta, H.; Furuta, K.; Sessler, J. L. J. Am. Chem. Soc. 1991, 113, 4706–4707.
71. Cram, D. J. Science 1988, 240, 760–767, and references therein.
72. Hahn, E. F.; Busso, M.; Mian, A.M.; Resnick, L. in Nucleotide Analogues as Antiviral Agents, Martin, J. C., Ed.; American Chemical Society: Washington, D.C., 1989.
73. Langer, R. Science 1990, 249, 1527–1533.
74. Sessler, J. L. et al. U.S. Pat. No. 4,935,498, and continuation-in-part, filed Jan. 20, 1992.
75. Blumenthal, R.; Loyter, A. Tibtech 1991, 9, 41–45.
76. Sambrook, J.; Fritsch, E. F.; Maniatis, T., Eds.; "Molecular Cloning"; Cold Spring Harbor Laboratory Press, 1989.
77. Král, V.; Sessler, J. L.; Furuta, H. J. Am. Chem. Soc., 1992 114, 8704–8705
78. Sessler, J. L.; Magda, D. J.; Furuta, H. J. Org. Chem. 1992 57, 818–826
79. Sessler, J. L., Cyr, M; Burrell, A.K. Tetrahedron, 1992, 44, 9661–9672.

80. Itahara, T.; Hashimoto, M.; Yumisashi, H. Synthesis, 1984, 255–256.

81. (a) Paine, John B., III in The Porphyrins, V.1, Pt. A. David Dolphin, Ed., 1978, pp. 101–234 (and references therein). (b) Sessler, J. L., Mozaffari, A., Johnson, M. Org. Syn., 1991, 70, 68–78. (c) Zard, S.Z., Barton, D., H. R., J. Chem. Soc., Chem. Commun., 1985, 1098–1100.

What is claimed is:

1. A macrocycle with one of the following structures:

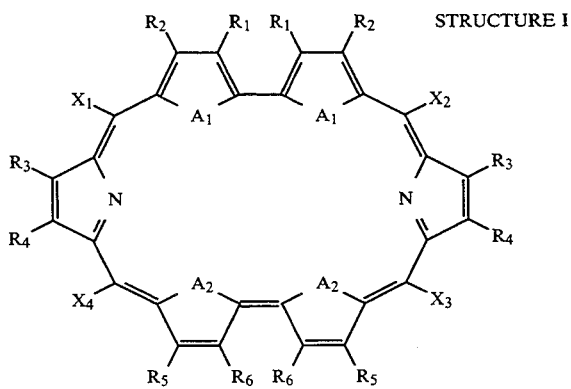

STRUCTURE I

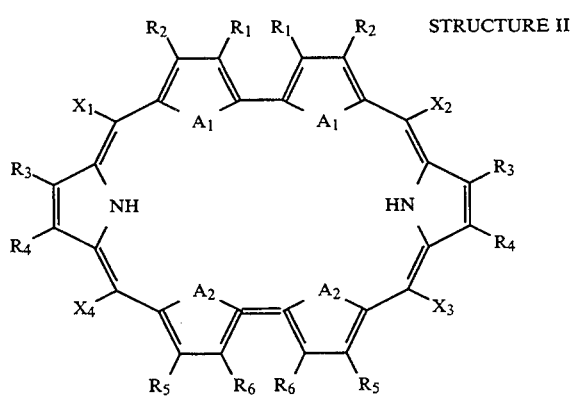

STRUCTURE II

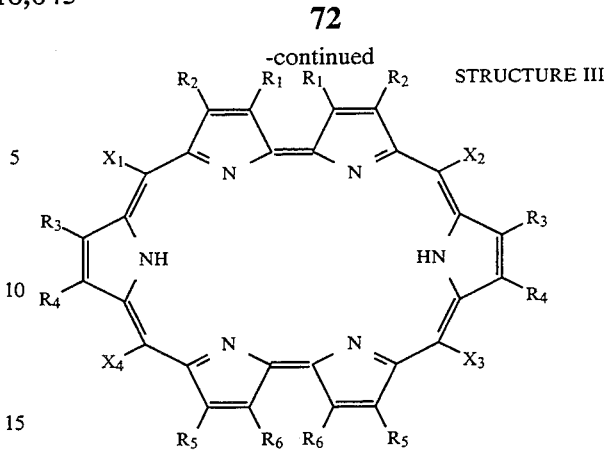

STRUCTURE III wherein:
$A_1$ and $A_2$ are nitrogen, oxygen or sulphur; and the substituents $R_1$, $R_2$, $R_3$, $R_4$, $R_5$, and $R_6$ and $X_1$, $X_2$, $X_3$, and $X_4$ are H, alkyl, aryl, amino, hydroxyl, alkoxy, carboxy, carboxamide, ester, amide, sulfonato, hydroxy substituted alkyl, alkoxyl substituted alkyl, carboxy substituted alkyl, ester substituted alkyl, amide substituted alkyl, amino substituted aryl, ester substituted aryl, ether substituted aryl, alkoxy substituted aryl, carboxy substituted aryl, amide substituted aryl, thio substituted ester, phospho substituted ester, amino substituted ester, or are of the formula $(CH_2)_n—A—(CH_2)_m—B$, wherein A is $CH_2$, O, S, NH, or $NR_7$, wherein $R_7$ is any of the groups listed above, n and m are integers $<10$ or zero, and B "is $H,CH_3,O,S,NH_2$ or $NR_7$."

2. The macrocycle of claim 1, wherein the macrocycle is either singly or doubly protonated.

3. The macrocycle of claim 2, wherein the macrocycle has a structure in accordance with structure I.

4. The macrocycle of claim 2, wherein the macrocycle has a structure in accordance with structure II.

5. The macrocycle of claim 2, wherein the macrocycle has a structure in accordance with structure III.

6. The macrocycle of claim 5, wherein the macrocycle is either singly, doubly, triply, or four-fold protonated.

7. The macrocycle of claim 1, wherein $A_1$ and $A_2$ are nitrogen.

8. The macrocycle of claim 1, wherein $A_1$ and $A_2$ are oxygen.

9. The macrocycle of claim 1, wherein $A_1$ and $A_2$ are sulphur.

10. The macrocycle of claim 1, wherein either $A_1$ or $A_2$ is nitrogen and the other is oxygen.

11. The macrocycle of claim 1, wherein either $A_1$ or $A_2$ is nitrogen and the other is sulphur.

12. The macrocycle of claim 1, wherein either $A_1$ or $A_2$ is oxygen and the other is sulphur.

13. The macrocycle of claim 1, further defined as having structure 10a of FIG. 3.

14. The macrocycle of claim 1, further defined as having structure 10b of FIG. 3.

15. The macrocycle of claim 1, further defined as having structure 17a of FIG. 4B.

16. The macrocycle of claim 1, further defined as having structure 17b of FIG. 4B.

17. The macrocycle of claim 1, further defined as having structure 18a of FIG. 4B.

18. The macrocycle of claim 1, further defined as having structure 18b of FIG. 4B.

19. The macrocycle of claim 1, further defined as having structure 19 of FIG. 5.

* * * * *

UNITED STATES PATENT AND TRADEMARK OFFICE
CERTIFICATE OF CORRECTION

PATENT NO.    :    5,410,045

DATED         :    April 25, 1995

INVENTOR(S)   :    Sessler *et al.*

It is certified that error appears in the above-identified patent and that said Letters Patent is hereby corrected as shown below:

On the title page, item number 75, line 2, delete "Yokohama" and insert --Kanagama--, therefor.

In claim 1, column 71, line 62, delete the horizontal line that depicts a double bond.

In claim 1, column 72, line 32, delete the quotation mark.

In claim 1, column 72, line 33, delete the quotation mark.

Signed and Sealed this

Third Day of October, 1995

*Attest:*

BRUCE LEHMAN

*Attesting Officer*          *Commissioner of Patents and Trademarks*